(12) United States Patent
Gray et al.

(10) Patent No.: US 6,958,226 B1
(45) Date of Patent: Oct. 25, 2005

(54) PACKAGING CELLS COMPRISING CODON-OPTIMIZED *GAGPOL* SEQUENCES AND LACKING LENTIVIRAL ACCESSORY PROTEINS

(75) Inventors: John T. Gray, Memphis, TN (US); Jeng-Shin Lee, Lincoln, MA (US); Richard C. Mulligan, Cambridge, MA (US)

(73) Assignee: The Children's Medical Center Corp., Boston, MA (US)

( * ) Notice: Subject to any disclaimer, the term of this patent is extended or adjusted under 35 U.S.C. 154(b) by 0 days.

(21) Appl. No.: 09/393,795

(22) Filed: Sep. 10, 1999

Related U.S. Application Data

(60) Provisional application No. 60/100,063, filed on Sep. 12, 1998, and provisional application No. 60/100,022, filed on Sep. 11, 1998.

(51) Int. Cl.$^7$ .................. C12N 15/64; C12N 15/00; C12N 15/09; C12N 15/86; C07H 21/04
(52) U.S. Cl. ............... 435/91.4; 435/320.1; 435/235.1; 435/456; 435/465; 424/93.1; 424/93.2; 424/93.21; 424/93.6
(58) Field of Search .................. 435/320.1, 465, 435/456, 325, 235.1, 91.4; 424/93.1, 93.2, 93.21, 93.6; 536/23.1

(56) References Cited

FOREIGN PATENT DOCUMENTS

| WO | WO 94/19478 | 9/1994 |
|---|---|---|
| WO | WO 94/29438 | 12/1994 |
| WO | WO 97/22709 | 6/1997 |
| WO | WO 97/27310 | 7/1997 |
| WO | WO 98/12207 | 3/1998 |
| WO | WO 98/17815 | 4/1998 |
| WO | WO 98/17816 | 4/1998 |
| WO | WO 00/31280 | 6/2000 |

OTHER PUBLICATIONS

Kotsopoulou, et al. Journal of Virology, May 2000, vol. 74, No. 10, pp. 4839–4952.*
Paul Luciw, Fundamental Virology, 3rd Ed., Fields, Knipe and Howley editors–in–chief, Lippencott–Raven, Philadelphia–New York, 1996, Chapter 27, p. 850.*
Srinivasakumar, N. et al., "The Effect of Viral Regulatory Protein Expression on Gene Delivery by Human Immuno-deficiency Virus Type 1 Vectors Produced in Stable packaging Cell Lines," *Journal of Virology*, 71(8) :5841–5848 (1997).
Haselhorst, D. et al., "Stable Packaging Cell Lines and HIV–1 Based Retroviral Vector Systems," *Gene Therapy*, 1 (Suppl. 2) :S14 (Nov. 18, 1994).
St. Louis, D. et al., "Construction and Characterization of HIV–1 Retroviral Vectors and Replication–Defective HIV–1 Packaging Cell Lines," *International Conference on AIDS and the STD World Congress*, p. 244 (Jun. 1, 1993).

Carroll, R. et al., "A Human Immunodeficiency Virus Type 1 (HIV–1)—Based Retroviral Vector System Utilizing Stable HIV–1 Packaging Cell Lines," *J. of Virology*, 68 (9) : 6047–6051 (Sep. 1, 1994).
Holler, T.P. et al., "HIV1 Integrase Expressed in *Escherichia coli* from a Synthetic Gene," *Gene*, 136 : 323–328 (Dec. 22, 1993).
André, S. et al., "Increased Immune Response Elicited by DNA Vaccination with a Synthetic GP120 Sequence with Optimized Codon Usage," *J. of Virology*, 72 (2) : 1497–1503 (Feb. 1, 1998).
Naldini, L. et al., "In Vivo Gene Delivery and Stable Transduction of Nondividing Cells by a Lentiviral Vector," *Science*, 272:263–267 (Apr. 12, 1996).
Soneoka, Y. et al., "A transient three–plasmid expression system for the production of high titer retroviral vectors," *Nucleic Acids Research*, 23 (4):628–633 (1995).
Kim, V.N. et al., "Minimal Requirement for a Lentivirus Vector Based on Human Immunodeficiency Virus type 1," *J. of Virology*, 72 (1):811–816 (Jan. 1998).
Srinivasakumar, N. et al., "The Effect of Viral Regulatory Protein Expression on Gene Delivery by Human Immunde-ficiency Virus Type 1 Vectors Produced in Stable Packaging Cell Lines," *J. of Virology*, 71(8):5841–5848 (Aug. 1997).
Haas, J. et al., "Codon usage limitation in the expression of HIV–1 envelope glycoprotein," *Current Biology*, 6(3):315–324 (1996).
Schwartz, S. et al., "Mutational Inactivation of an Inhibitory Sequence in Human Immunodeficiency Virus Type 1 Results in Rev–Independent *gag* Expression," *J. Virology*, 66(12):7176–7182 (Dec. 1992).
Markowitz, D. et al., "A Safe Packaging Line for Gene Transfer: Separating Viral Genes on Two Different Plasmids," *J. of Virology*, 62:1120–1124 (Apr. 1988).
Dougherty, J.P. et al., "New Retrovirus Helper Cells with Almost No Nucletide Sequence Homology to Retrovirus Vectors," *J. of Virology*, 63(7):3209–3212 (Jul. 1989).
Miller, A.D and Buttimore, C., "Redesign of Retrovirus Packaging Cell Lines to Avoid Recombination Leading to Helper Virus Production," *Molecular and Cellular Biology*, 6(8):2895–2902 (Aug. 1986).
Mann, R. et al., "Construction of a Retrovirus Packaging Mutant and Its Use to Produce Helper–Free Defective Retrovirus," *Cell*, 33:153–159 (May 1983).

(Continued)

*Primary Examiner*—Gerry Leffers
(74) *Attorney, Agent, or Firm*—Hamilton, Brooks, Smith & Reynolds, P.C.

(57) ABSTRACT

Novel packaging cell lines useful for generating viral accessory protein independent HIV-derived retroviral vector particles, methods of constructing such packaging cell lines and methods of using the viral accessory protein independent HIV-derived retroviral vector particles are disclosed.

22 Claims, 29 Drawing Sheets

OTHER PUBLICATIONS

Cone, R.D. and Mulligan, R.C., "High-efficiency gene transfer into mammalian cells: Generation of helper-free recombinant with broad mammalian host range," *Proc. Natl. Acad. Sci. USA*, 81:6349–6353 (Oct. 1984).

Danos, O. and Mulligan, R.C., "Safe and efficient generation of recombinant retroviruses with amphotropic and ecotropic host ranges," *Proc. Natl. Acad. Sci. USA*, 85:6460–6464 (Sep. 1988).

Markowitz, D.G. et al., "Safe and Efficient Ecotropic and Amphotropic Packaging Lines for Use in Gene Transfer Experiments," *Trans. Assoc. Am. Physicians,* 101:212–218 (1988).

Fleischman, R.A., "Southwestern Internal Medicine Conference: Human Gene Therapy," *The American Journal of the Medical Sciences,* 301(5):353–363 (May 1991).

Parveen, Z., et al., "Spleen Necrosis Virus–Deprived C–type Retroviral Vectors for Gene Transfer to Quicscent Cells," *Nature Biotechnology* 18:623–629 (2000).

* cited by examiner

Codon Usage Frequencies

| Amino Acid | pNL4-3 gagpol | mam | Amino Acid | pNL4-3 gagpol | mam | Amino Acid | pNL4-3 gagpol | mam |
|---|---|---|---|---|---|---|---|---|
| gca Ala(A) | 58 | 13 | gga Gly(G) | 55 | 14 | cca Pro(P) | 53 | 16 |
| gcc Ala(A) | 23 | 53 | ggc Gly(G) | 12 | 50 | ccc Pro(P) | 17 | 48 |
| gcg Ala(A) | 5 | 17 | ggg Gly(G) | 27 | 24 | ccg Pro(P) | 2 | 17 |
| gcu Ala(A) | 14 | 17 | ggu Gly(G) | 6 | 12 | ccu Pro(P) | 27 | 19 |
| aga Arg(R) | 63 | 10 | cac His(H) | 24 | 79 | agc Ser(S) | 29 | 34 |
| agg Arg(R) | 30 | 18 | cau His(H) | 76 | 21 | agu Ser(S) | 26 | 10 |
| cga Arg(R) | 4 | 6 | | | | uca Ser(S) | 26 | 5 |
| cgc Arg(R) | 0 | 37 | aua Ile(I) | 57 | 5 | ucc Ser(S) | 7 | 28 |
| cgg Arg(R) | 3 | 21 | auc Ile(I) | 17 | 77 | ucg Ser(S) | 4 | 9 |
| cgu Arg(R) | 0 | 7 | auu Ile(I) | 26 | 18 | ucu Ser(S) | 6 | 13 |
| aac Asn(N) | 27 | 78 | cua Leu(L) | 15 | 3 | aca Thr(T) | 52 | 14 |
| aau Asn(N) | 73 | 22 | cuc Leu(L) | 10 | 26 | acc Thr(T) | 18 | 57 |
| gac Asp(D) | 40 | 75 | cug Leu(L) | 11 | 58 | acg Thr(T) | 1 | 15 |
| gau Asp(D) | 60 | 25 | cuu Leu(L) | 11 | 5 | acu Thr(T) | 29 | 14 |
| ugc Cys(C) | 14 | 68 | uua Leu(L) | 40 | 2 | ugg Trp(W) | 100 | 100 |
| ugu Cys(C) | 26 | 32 | uug Leu(L) | 13 | 6 | | | |
| caa Gln(Q) | 56 | 12 | aaa Lys(K) | 69 | 18 | uac Tyr(Y) | 26 | 74 |
| cag Gln(Q) | 44 | 88 | aag Lys(K) | 31 | 82 | uau Tyr(Y) | 74 | 26 |
| gaa Glu(E) | 70 | 25 | aug Met(M) | 100 | 100 | gua Val(V) | 58 | 5 |
| gag Glu(E) | 30 | 75 | | | | guc Val(V) | 13 | 25 |
| | | | uuc Phe(F) | 40 | 80 | gug Val(V) | 16 | 64 |
| | | | uuu Phe(F) | 60 | 20 | guu Val(V) | 14 | 7 |

Fig. 2

Rev

- Regulates HIV gene expression by promoting cytoplasmic levels of unspliced and singly spliced mRNAs

- Postulated to affect splicing, stability, transport, and translation

Fig. 4

Codon Optimization of HIV *gagpol*

- Remove A-rich instability elements

- Improve translational efficiency

- Reduce risk of recombination with transfer vector

Fig. 5

Inactivation of Inhibitory Sequences in *gag*

Schwartz, S., et al.

```
336
     atg ggt gcg aga gcg tca gta tta agc ggg gga gaa tta gat cga tgg gaa aaa att cgg
396
                                                              M1
     tta agg c Alignment Report of Codon optimization (gag).MEG, using Clustal method with PAM250 residue weight table.

```
                                810
                                 |
792     M    G    A    R    A    S    V    L    S    G    G    E    L    D    K    NL4-3 genbank.SEQ
792     ATG  GGT  GCG  AGA  GCG  TCG  GTA  TTA  AGC  GGG  GGA  GAA  TTA  GAT  AAA
1319    M    G    A    R    A    S    V    L    S    G    G    E    L    D    K    pHDMHgpm2.seq
1319    ATG  GGC  GCC  CGC  GCC  TCC  GTG  CTG  TCC  GGC  GGC  GAG  CTG  GAC  AAG 840                                    870
               |                                      |
837     W    E    K    I    R    L    R    P    G    G    K    K    Q    Y    K    NL4-3 genbank.SEQ
837     TGG  GAA  AAA  ATT  CGG  TTA  AGG  CCA  GGG  GGA  AAG  AAA  CAA  TAT  AAA
1364    W    E    K    I    R    L    R    P    G    G    K    K    Q    Y    K    pHDMHgpm2.seq
1364    TGG  GAG  AAG  ATC  CGC  CTG  CGC  CCC  GGC  GGC  AAG  AAG  CAG  TAC  AAG 900
                                 |
882     L    K    H    I    V    W    A    S    R    E    L    E    R    F    A    NL4-3 genbank.SEQ
882     CTA  AAA  CAT  ATA  GTA  TGG  GCA  AGC  AGG  GAG  CTA  GAA  CGA  TTC  GCA
1409    L    K    H    I    V    W    A    S    R    E    L    E    R    F    A    pHDMHgpm2.seq
1409    CTG  AAG  CAC  ATC  GTG  TGG  GCC  TCC  CGC  GAG  CTG  GAG  CGC  TTC  GCC 930                                    960
               |                                      |
927     V    N    P    G    L    L    E    T    S    E    G    C    R    Q    I    NL4-3 genbank.SEQ
927     GTT  AAT  CCT  GGC  CTT  TTA  GAG  ACA  TCA  GAA  GGC  TGT  AGA  CAA  ATA
1454    V    N    P    G    L    L    E    T    S    E    G    C    R    Q    I    pHDMHgpm2.seq
1454    GTG  AAC  CCC  GGC  CTG  CTG  GAG  ACC  TCC  GAG  GGC  TGC  CGC  CAG  ATC 990
                                 |
972     L    G    Q    L    Q    P    S    L    Q    T    G    S    E    E    L    NL4-3 genbank.SEQ
972     CTG  GGA  CAG  CTA  CAA  CCA  TCC  CTT  CAG  ACA  GGA  TCA  GAA  GAA  CTT
1499    L    G    Q    L    Q    P    S    L    Q    T    G    S    E    E    L    pHDMHgpm2.seq
1499    CTG  GGC  CAG  CTG  CAG  CCC  TCC  CTG  CAA  ACC  GGC  TCC  GAG  GAG  CTG 1020                                   1050
               |                                      |
1017    R    S    L    Y    N    T    I    A    V    L    Y    C    V    H    Q    NL4-3 genbank.SEQ
1017    AGA  TCA  TTA  TAT  AAT  ACA  ATA  GCA  GTC  CTC  TAT  TGT  GTG  CAT  CAA
1544    R    S    L    Y    N    T    I    A    V    L    Y    C    V    H    Q    pHDMHgpm2.seq
1544    CGC  TCC  CTG  TAC  AAC  ACC  ATC  GCC  GTG  CTG  TAC  TGC  GTG  CAC  CAG 1080
                                 |
1062    R    I    D    V    K    D    T    K    E    A    L    D    K    I    E    NL4-3 genbank.SEQ
1062    AGG  ATA  GAT  GTA  AAA  GAC  ACC  AAG  GAA  GCC  TTA  GAT  AAG  ATA  GAG
1589    R    I    D    V    K    D    T    K    E    A    L    D    K    I    E    pHDMHgpm2.seq
1589    CGC  ATC  GAC  GTG  AAG  GAC  ACC  AAG  GAG  GCC  CTG  GAC  AAG  ATC  GAG 1110                                   1140
               |                                      |
1107    E    E    Q    N    K    S    K    K    K    A    Q    Q    A    A    A    NL4-3 genbank.SEQ
1107    GAA  GAG  CAA  AAC  AAA  AGT  AAG  AAA  AAG  GCA  CAG  CAA  GCA  GCA  GCT
1634    E    E    Q    N    K    S    K    K    K    A    Q    Q    A    A    A    pHDMHgpm2.seq
1634    GAG  GAG  CAG  AAC  AAG  TCC  AAG  AAG  AAG  GCC  CAG  CAG  GCC  GCC  GCC
```

FIG. 8A

Alignment Report of Codon optimization (gag).MEG, using Clustal method with PAM250 residue weight table.

```
                                1170
1152   D   T   G   N   N   S   Q   V   S   Q   N   Y   P   I   V    NL4-3 genbank.SEQ
1152  GAC ACA GGA AAC AAC AGC CAG GTC AGC CAA AAT TAC CCT ATA GTG
1679   D   T   G   N   N   S   Q   V   S   Q   N   Y   P   I   V    pHDMHgpm2.seq
1679  GAC ACC GGC AAC AAC TCC CAG GTG TCC CAG AAC TAC CCC ATC GTG 1200                            1230
1197   Q   N   L   Q   G   Q   M   V   H   Q   A   I   S   P   R    NL4-3 genbank.SEQ
1197  CAG AAC CTC CAG GGG CAA ATG GTA CAT CAG GCC ATA TCA CCT AGA
1724   Q   N   L   Q   G   Q   M   V   H   Q   A   I   S   P   R    pHDMHgpm2.seq
1724  CAG AAC CTG CAG GGC CAG ATG GTG CAC CAG GCC ATC TCC CCC CGC 1260
1242   T   L   N   A   W   V   K   V   V   E   E   K   A   F   S    NL4-3 genbank.SEQ
1242  ACT TTA AAT GCA TGG GTA AAA GTA GTA GAA GAG AAG GCT TTC AGC
1769   T   L   N   A   W   V   K   V   V   E   E   K   A   F   S    pHDMHgpm2.seq
1769  ACC CTG AAC GCC TGG GTG AAG GTG GTG GAG GAG AAG GCC TTC TCC 1290                            1320
1287   P   E   V   I   P   M   F   S   A   L   S   E   G   A   T    NL4-3 genbank.SEQ
1287  CCA GAA GTA ATA CCC ATG TTT TCA GCA TTA TCA GAA GGA GCC ACC
1814   P   E   V   I   P   M   F   S   A   L   S   E   G   A   T    pHDMHgpm2.seq
1814  CCC GAA GTC ATC CCC ATG TTC TCC GCC CTG TCC GAG GGC GCC ACC 1350
1332   P   Q   D   L   N   T   M   L   N   T   V   G   G   H   Q    NL4-3 genbank.SEQ
1332  CCA CAA GAT TTA AAT ACC ATG CTA AAC ACA GTG GGG GGA CAT CAA
1859   P   Q   D   L   N   T   M   L   N   T   V   G   G   H   Q    pHDMHgpm2.seq
1859  CCC CAG GAC CTG AAC ACC ATG CTG AAC ACC GTG GGC GGC CAC CAG 1380                            1410
1377   A   A   M   Q   M   L   K   E   T   I   N   E   E   A   A    NL4-3 genbank.SEQ
1377  GCA GCC ATG CAA ATG TTA AAA GAG ACC ATC AAT GAG GAA GCT GCA
1904   A   A   M   Q   M   L   K   E   T   I   N   E   E   A   A    pHDMHgpm2.seq
1904  GCC GCC ATG CAG ATG CTG AAG GAG ACC ATC AAC GAG GAG GCC GCC 1440
1422   E   W   D   R   L   H   P   V   H   A   G   P   I   A   P    NL4-3 genbank.SEQ
1422  GAA TGG GAT AGA TTG CAT CCA GTG CAT GCA GGG CCT ATT GCA CCA
1949   E   W   D   R   L   H   P   V   H   A   G   P   I   A   P    pHDMHgpm2.seq
1949  GAG TGG GAC CGC CTG CAC CCC GTG CAC GCC GGC CCC ATC GCC CCC 1470                            1500
1467   G   Q   M   R   E   P   R   G   S   D   I   A   G   T   T    NL4-3 genbank.SEQ
1467  GGC CAG ATG AGA GAA CCA AGG GGA AGT GAC ATA GCA GGA ACT ACT
1994   G   Q   M   R   E   P   R   G   S   D   I   A   G   T   T    pHDMHgpm2.seq
1994  GGC CAG ATG CGC GAG CCC CGC GGC TCC GAC ATC GCC GGC ACC ACC
```

Fig. 8B

Alignment Report of Codon optimization (gag).MEG, using Clustal method with PAM250 residue weight table.

```
             1530
1512  S   T   L   Q   E   Q   I   G   W   M   T   H   N   P   P    NL4-3 genbank.SEQ
1512 AGT ACC CTT CAG GAA CAA ATA GGA TGG ATG ACA CAT AAT CCA CCT
2039  S   T   L   Q   E   Q   I   G   W   M   T   H   N   P   P    pHDMHgpm2.seq
2039 TCC ACC CTG CAA GAG CAG ATC GGC TGG ATG ACC CAC AAC CCC CCC 1560                              1590
1557  I   P   V   G   E   I   Y   K   R   W   I   I   L   G   L    NL4-3 genbank.SEQ
1557 ATC CCA GTA GGA GAA ATC TAT AAA AGA TGG ATA ATC CTG GGA TTA
2084  I   P   V   G   E   I   Y   K   R   W   I   I   L   G   L    pHDMHgpm2.seq
2084 ATC CCC GTG GGC GAG ATC TAC AAG CGC TGG ATC ATC CTG GGC CTG 1620
1602  N   K   I   V   R   M   Y   S   P   T   S   I   L   D   I    NL4-3 genbank.SEQ
1602 AAT AAA ATA GTA AGA ATG TAT AGC CCT ACC AGC ATT CTG GAC ATA
2129  N   K   I   V   R   M   Y   S   P   T   S   I   L   D   I    pHDMHgpm2.seq
2129 AAC AAG ATC GTG CGC ATG TAC TCC CCC ACC TCC ATC CTG GAC ATC 1650                              1680
1647  R   Q   G   P   K   E   P   F   R   D   Y   V   D   R   F    NL4-3 genbank.SEQ
1647 AGA CAA GGA CCA AAG GAA CCC TTT AGA GAC TAT GTA GAC CGA TTC
2174  R   Q   G   P   K   E   P   F   R   D   Y   V   D   R   F    pHDMHgpm2.seq
2174 CGC CAG GGC CCC AAG GAG CCC TTC CGC GAC TAC GTG GAC CGC TTC 1710
1692  Y   K   T   L   R   A   E   Q   A   S   Q   E   V   K   N    NL4-3 genbank.SEQ
1692 TAT AAA ACT CTA AGA GCC GAG CAA GCT TCA CAA GAG GTA AAA AAT
2219  Y   K   T   L   R   A   E   Q   A   S   Q   E   V   K   N    pHDMHgpm2.seq
2219 TAC AAG ACC CTG CGC GCC GAG CAG GCC TCC CAG GAG GTA AAG AAC 1740                              1770
1737  W   M   T   E   T   L   L   V   Q   N   A   N   P   D   C    NL4-3 genbank.SEQ
1737 TGG ATG ACA GAA ACC TTG TTG GTC CAA AAT GCG AAC CCA GAT TGT
2264  W   M   T   E   T   L   L   V   Q   N   A   N   P   D   C    pHDMHgpm2.seq
2264 TGG ATG ACC GAG ACC CTG CTG GTG CAG AAC GCC AAC CCC GAC TGC 1800
1782  K   T   I   L   K   A   L   G   P   G   A   T   L   E   E    NL4-3 genbank.SEQ
1782 AAG ACT ATT TTA AAA GCA TTG GGA CCA GGA GCG ACA CTA GAA GAA
2309  K   T   I   L   K   A   L   G   P   G   A   T   L   E   E    pHDMHgpm2.seq
2309 AAG ACC ATC CTG AAG GCC CTG GGC CCC GGC GCC ACC CTG GAG GAG 1830                              1860
1827  M   M   T   A   C   Q   G   V   G   G   P   G   H   K   A    NL4-3 genbank.SEQ
1827 ATG ATG ACA GCA TGT CAG GGA GTG GGG GGA CCC GGC CAT AAA GCA
2354  M   M   T   A   C   Q   G   V   G   G   P   G   H   K   A    pHDMHgpm2.seq
2354 ATG ATG ACC GCC TGC CAG GGC GTG GGC GGC CCC GGC CAC AAG GCC
```

Fig. 8C

Alignment Report of Codon optimization (gag).MEG, using Clustal method with PAM250 residue weight table.

```
                             1890
     ┌─────────────────────────┴──────────────────────────┐
1872   R   V   L   A   E   A   M   S   Q   V   T   N   P   A   T    NL4-3 genbank.SEQ
1872  AGA GTT TTG GCT GAA GCA ATG AGC CAA GTA ACA AAT CCA GCT ACC
2399   R   V   L   A   E   A   M   S   Q   V   T   N   P   A   T    pHDMHgpm2.seq
2399  CGC GTG CTG GCC GAG GCC ATG TCC CAA GTC ACC AAC CCC GCC ACC 1920                              1950
     ┌───────┴──────────────────────────┬──────┴──────────┐
1917   I   M   I   Q   K   G   N   F   R   N   Q   R   K   T   V    NL4-3 genbank.SEQ
1917  ATA ATG ATA CAG AAA GGC AAT TTT AGG AAC CAA AGA AAG ACT GTT
2444   I   M   I   Q   K   G   N   F   R   N   Q   R   K   T   V    pHDMHgpm2.seq
2444  ATC ATG ATC CAG AAG GGC AAC TTC CGC AAC CAG CGC AAG ACC GTG 1980
     ┌──────────────────────┴──────────────────────────────┐
1962   K   C   F   N   C   G   K   E   G   H   I   A   K   N   C    NL4-3 genbank.SEQ
1962  AAG TGT TTC AAT TGT GGC AAA GAA GGG CAC ATA GCC AAA AAT TGC
2489   K   C   F   N   C   G   K   E   G   H   I   A   K   N   C    pHDMHgpm2.seq
2489  AAG TGC TTC AAC TGC GGC AAG GAG GGC CAC ATC GCC AAG AAC TGC 2010                              2040
     ┌───────┴──────────────────────────┬──────┴──────────┐
2007   R   A   P   R   K   K   G   C   W   K   C   G   K   E   G    NL4-3 genbank.SEQ
2007  AGG GCC CCT AGG AAA AAG GGC TGT TGG AAA TGT GGA AAG GAA GGA
2534   R   A   P   R   K   K   G   C   W   K   C   G   K   E   G    pHDMHgpm2.seq
2534  CGC GCC CCC CGC AAG AAG GGC TGC TGG AAG TGC GGC AAG GAG GGC 2070
     ┌──────────────────────┴──────────────────────────────┐
2052   H   Q   M   K   D   C   T   E   R   Q   A   N   F   L   G    NL4-3 genbank.SEQ
2052  CAC CAA ATG AAA GAT TGT ACT GAG AGA CAG GCT AAT TTT TTA GGG
2579   H   Q   M   K   D   C   T   E   R   Q   A   N   F   L   G    pHDMHgpm2.seq
2579  CAC CAG ATG AAA GAT TGT ACT GAG AGA CAG GCT AAT TTT TTA GGG 2100                              2130
     ┌───────┴──────────────────────────┬──────┴──────────┐
2097   K   I   W   P   S   H   K   G   R   P   G   N   F   L   Q    NL4-3 genbank.SEQ
2097  AAG ATC TGG CCT TCC CAC AAG GGA AGG CCA GGG AAT TTT CTT CAG
2624   K   I   W   P   S   H   K   G   R   P   G   N   F   L   Q    pHDMHgpm2.seq
2624  AAG ATC TGG CCT TCC CAC AAG GGA AGG CCA GGG AAT TTT CTT CAG 2160
     ┌──────────────────────┴──────────────────────────────┐
2142   S   R   P   E   P   T   A   P   P   E   E   S   F   R   F    NL4-3 genbank.SEQ
2142  AGC AGA CCA GAG CCA ACA GCC CCA CCA GAA GAG AGC TTC AGG TTT
2669   S   R   P   E   P   T   A   P   P   E   E   S   F   R   F    pHDMHgpm2.seq
2669  AGC AGA CCA GAG CCA ACA GCC CCA CCA GAA GAG AGC TTC AGG TTT 2190                              2220
     ┌───────┴──────────────────────────┬──────┴──────────┐
2187   G   E   E   T   T   T   P   S   Q   K   Q   E   P   I   D    NL4-3 genbank.SEQ
2187  GGG GAA GAG ACA ACA ACT CCC TCT CAG AAG CAG GAG CCG ATA GAC
2714   G   E   E   T   T   T   P   S   Q   K   Q   E   P   I   D    pHDMHgpm2.seq
2714  GGG GAA GAG ACA ACA ACT CCC TCT CAG AAG CAG GAG CCG ATA GAC
```

Fig. 8D

Alignment Report of Codon optimization (gag).MEG, using Clustal method with PAM250 residue weight table.

```
                    2250
2232   K   E   L   Y   P   L   A   S   L   R   S   L   F   G   S    NL4-3 genbank.SEQ
2232  AAG GAA CTG TAT CCT TTA GCT TCC CTC AGA TCA CTC TTT GGC AGC
2759   K   E   L   Y   P   L   A   S   L   R   S   L   F   G   S    pHDMHgpm2.seq
2759  AAG GAA CTG TAT CCT TTA GCT TCC CTC AGA TCA CTC TTT GGC AGC 2280
2277   D   P   S   S   Q                                             NL4-3 genbank.SEQ
2277  GAC CCC TCG TCA CAA TAA
2804   D   P   S   S   Q                                             pHDMHgpm2.seq
2804  GAC CCC TCG TCA CAA TAA
```

Fig. 8E

Alignment Report of Codon Optimization (pol).MEG, using Clustal method with PAM250 residue weight table.

```
          2090                               2120
2087  F   F   R   E   D   L   A   F   P   Q   G   K   A   R   E    NL4-3 genbank.SEQ
2087  TTT TTT AGG GAA GAT CTG GCC TTC CCA CAA GGG AAG GCC AGG GAA
2085  F   F   R   E   D   L   A   F   P   Q   G   K   A   R   E    pNL4-3.seq
2085  TTT TTT AGG GAA GAT CTG GCC TTC CCA CAA GGG AAG GCC AGG GAA
2612  F   F   R   E   D   L   A   F   P   Q   G   K   A   R   E    pHDMHgpm2.seq
2612  TTT TTT AGG GAA GAT CTG GCC TTC CCA CAA GGG AAG GCC AGG GAA 2150
2132  F   S   S   E   Q   T   R   A   N   S   P   T   R   R   E    NL4-3 genbank.SEQ
2132  TTT TCT TCA GAG CAG ACC AGA GCC AAC AGC CCC ACC AGA AGA GAG
2130  F   S   S   E   Q   T   R   A   N   S   P   T   R   R   E    pNL4-3.seq
2130  TTT TCT TCA GAG CAG ACC AGA GCC AAC AGC CCC ACC AGA AGA GAG
2657  F   S   S   E   Q   T   R   A   N   S   P   T   R   R   E    pHDMHgpm2.seq
2657  TTT TCT TCA GAG CAG ACC AGA GCC AAC AGC CCC ACC AGA AGA GAG 2180                               2210
2177  L   Q   V   W   G   R   D   N   N   S   L   S   E   A   G    NL4-3 genbank.SEQ
2177  CTT CAG GTT TGG GGA AGA GAC AAC AAC TCC CTC TCA GAA GCA GGA
2175  L   Q   V   W   G   R   D   N   N   S   L   S   E   A   G    pNL4-3.seq
2175  CTT CAG GTT TGG GGA AGA GAC AAC AAC TCC CTC TCA GAA GCA GGA
2702  L   Q   V   W   G   R   D   N   N   S   L   S   E   A   G    pHDMHgpm2.seq
2702  CTT CAG GTT TGG GGA AGA GAC AAC AAC TCC CTC TCA GAA GCA GGA 2240
2222  A   D   R   Q   G   T   V   S   F   S   F   P   Q   I   T    NL4-3 genbank.SEQ
2222  GCC GAT AGA CAA GGA ACT GTA TCC TTT AGC TTC CCT CAG ATC ACT
2220  A   D   R   Q   G   T   V   S   F   S   F   P   Q   I   T    pNL4-3.seq
2220  GCC GAT AGA CAA GGA ACT GTA TCC TTT AGC TTC CCT CAG ATC ACT
2747  A   D   R   Q   G   T   V   S   F   S   F   P   Q   I   T    pHDMHgpm2.seq
2747  GCC GAT AGA CAA GGA ACT GTA TCC TTT AGC TTC CCT CAG ATC ACT 2270                               2300
2267  L   W   Q   R   P   L   V   T   I   K   I   G   G   Q   L    NL4-3 genbank.SEQ
2267  CTT TGG CAG CGA CCC CTC GTC ACA ATA AAG ATA GGG GGG CAA TTA
2265  L   W   Q   R   P   L   V   T   I   K   I   G   G   Q   L    pNL4-3.seq
2265  CTT TGG CAG CGA CCC CTC GTC ACA ATA AAG ATA GGG GGG CAA TTA
2792  L   W   Q   R   P   L   V   T   I   K   I   G   G   Q   L    pHDMHgpm2.seq
2792  CTT TGG CAG CGA CCC CTC GTC ACA ATA AAG ATC GGT GGC CAG CTG 2330
2312  K   E   A   L   L   D   T   G   A   D   D   T   V   L   E    NL4-3 genbank.SEQ
2312  AAG GAA GCT CTA TTA GAT ACA GGA GCA GAT GAT ACA GTA TTA GAA
2310  K   E   A   L   L   D   T   G   A   D   D   T   V   L   E    pNL4-3.seq
2310  AAG GAA GCT CTA TTA GAT ACA GGA GCA GAT GAT ACA GTA TTA GAA
2837  K   E   A   L   L   D   T   G   A   D   D   T   V   L   E    pHDMHgpm2.seq
2837  AAG GAG GCC CTG CTG GAC ACC GGC GCC GAC GAC ACC GTG CTG GAG
```

Fig. 9A

Alignment Report of Codon Optimization (pol).MEG, using Clustal method with PAM250 residue weight table.

```
           2360                                    2390
2357   E    M    N    L    P    G    R    W    K    P    K    M    I    G    G    NL4-3 genbank.SEQ
2357  GAA  ATG  AAT  TTG  CCA  GGA  AGA  TGG  AAA  CCA  AAA  ATG  ATA  GGG  GGA
2355   E    M    N    L    P    G    R    W    K    P    K    M    I    G    G    pNL4-3.seq
2355  GAA  ATG  AAT  TTG  CCA  GGA  AGA  TGG  AAA  CCA  AAA  ATG  ATA  GGG  GGA
2882   E    M    N    L    P    G    R    W    P    K    M    I    G    G         pHDMHgpm2.seq
2882  GAG  ATG  AAC  CTG  CCC  GGC  CGC  TGG  AAG  CCC  AAG  ATG  ATC  GGC  GGC 2420
2402   I    G    G    F    I    K    V    G    Q    Y    D    Q    I    L    I    NL4-3 genbank.SEQ
2402  ATT  GGA  GGT  TTT  ATC  AAA  GTA  GGA  CAG  TAT  GAT  CAG  ATA  CTC  ATA
2400   I    G    G    F    I    K    V    R    Q    Y    D    Q    I    L    I    pNL4-3.seq
2400  ATT  GGA  GGT  TTT  ATC  AAA  GTA  AGA  CAG  TAT  GAT  CAG  ATA  CTC  ATA
2927   I    G    G    F    I    K    V    R    Q    Y    D    Q    I    L    I    pHDMHgpm2.seq
2927  ATC  GGC  GGC  TTC  ATC  AAA  GTC  CGC  CAG  TAC  GAC  CAG  ATC  CTG  ATC 2450                                    2480
2447   E    I    C    G    H    K    A    I    G    T    V    L    V    G    P    NL4-3 genbank.SEQ
2447  GAA  ATC  TGC  GGA  CAT  AAA  GCT  ATA  GGT  ACA  GTA  TTA  GTA  GGA  CCT
2445   E    I    C    G    H    K    A    I    G    T    V    L    V    G    P    pNL4-3.seq
2445  GAA  ATC  TGC  GGA  CAT  AAA  GCT  ATA  GGT  ACA  GTA  TTA  GTA  GGA  CCT
2972   E    I    C    G    H    K    A    I    G    T    V    L    V    G    P    pHDMHgpm2.seq
2972  GAG  ATC  TGC  GGC  CAC  AAG  GCC  ATC  GGC  ACC  GTG  CTG  GTG  GGC  CCC 2510
2492   T    P    V    N    I    I    G    R    N    L    L    T    Q    I    G    NL4-3 genbank.SEQ
2492  ACA  CCT  GTC  AAC  ATA  ATT  GGA  AGA  AAT  CTG  TTG  ACT  CAG  ATT  GGC
2490   T    P    V    N    I    I    G    R    N    L    L    T    Q    I    G    pNL4-3.seq
2490  ACA  CCT  GTC  AAC  ATA  ATT  GGA  AGA  AAT  CTG  TTG  ACT  CAG  ATT  GGC
3017   T    P    V    N    I    I    G    R    N    L    L    T    Q    I    G    pHDMHgpm2.seq
3017  ACC  CCC  GTG  AAC  ATC  ATC  GGC  CGC  AAC  CTG  CTG  ACC  CAG  ATC  GGC 2540                                    2570
2537   C    T    L    N    F    P    I    S    P    I    E    T    V    P    V    NL4-3 genbank.SEQ
2537  TGC  ACT  TTA  AAT  TTT  CCC  ATT  AGT  CCT  ATT  GAG  ACT  GTA  CCA  GTA
2535   C    T    L    N    F    P    I    S    P    I    E    T    V    P    V    pNL4-3.seq
2535  TGC  ACT  TTA  AAT  TTT  CCC  ATT  AGT  CCT  ATT  GAG  ACT  GTA  CCA  GTA
3062   C    T    L    N    F    P    I    S    P    I    E    T    V    P    V    pHDMHgpm2.seq
3062  TGC  ACC  CTG  AAC  TTC  CCC  ATC  TCC  CCC  ATC  GAG  ACC  GTG  CCC  GTG 2600
2582   K    L    K    P    G    M    D    G    P    K    V    K    Q    W    P    NL4-3 genbank.SEQ
2582  AAA  TTA  AAG  CCA  GGA  ATG  GAT  GGC  CCA  AAA  GTT  AAA  CAA  TGG  CCA
2580   K    L    K    P    G    M    D    G    P    K    V    K    Q    W    P    pNL4-3.seq
2580  AAA  TTA  AAG  CCA  GGA  ATG  GAT  GGC  CCA  AAA  GTT  AAA  CAA  TGG  CCA
3107   K    L    K    P    G    M    D    G    P    K    V    K    Q    W    P    pHDMHgpm2.seq
3107  AAG  CTG  AAG  CCC  GGC  ATG  GAC  GGC  CCC  AAA  GTC  AAG  CAG  TGG  CCC
```

Fig. 9B

Alignment Report of Codon Optimization (pol).MEG, using Clustal method with PAM250 residue weight table.

```
             2630                                    2660
2627    L    T    E    E    K    I    K    A    L    V    E    I    C    T    E    NL4-3 genbank.SEQ
2627    TTG  ACA  GAA  GAA  AAA  ATA  AAA  GCA  TTA  GTA  GAA  ATT  TGT  ACA  GAA
2625    L    T    E    E    K    I    K    A    L    V    E    I    C    T    E    pNL4-3.seq
2625    TTG  ACA  GAA  GAA  AAA  ATA  AAA  GCA  TTA  GTA  GAA  ATT  TGT  ACA  GAA
3152    L    T    E    E    K    I    K    A    L    V    E    I    C    T    E    pHDMHgpm2.seq
3152    CTG  ACC  GAG  GAG  AAG  ATC  AAG  GCC  CTG  GTG  GAG  ATC  TGC  ACC  GAG 2690
2672    M    E    K    E    G    K    I    S    K    I    G    P    E    N    P    NL4-3 genbank.SEQ
2672    ATG  GAA  AAG  GAA  GGA  AAA  ATT  TCA  AAA  ATT  GGG  CCT  GAA  AAT  CCA
2670    M    E    K    E    G    K    I    S    K    I    G    P    E    N    P    pNL4-3.seq
2670    ATG  GAA  AAG  GAA  GGA  AAA  ATT  TCA  AAA  ATT  GGG  CCT  GAA  AAT  CCA
3197    M    E    K    E    G    K    I    S    K    I    G    P    E    N    P    pHDMHgpm2.seq
3197    ATG  GAG  AAG  GAG  GGC  AAG  ATC  TCC  AAG  ATC  GGC  CCC  GAG  AAC  CCC 2720                                    2750
2717    Y    N    T    P    V    F    A    I    K    K    K    D    S    T    K    NL4-3 genbank.SEQ
2717    TAC  AAT  ACT  CCA  GTA  TTT  GCC  ATA  AAG  AAA  AAA  GAC  AGT  ACT  AAA
2715    Y    N    T    P    V    F    A    I    K    K    K    D    S    T    K    pNL4-3.seq
2715    TAC  AAT  ACT  CCA  GTA  TTT  GCC  ATA  AAG  AAA  AAA  GAC  AGT  ACT  AAA
3242    Y    N    T    P    V    F    A    I    K    K    K    D    S    T    K    pHDMHgpm2.seq
3242    TAC  AAC  ACC  CCC  GTG  TTC  GCC  ATC  AAG  AAG  AAG  GAC  TCC  ACC  AAG 2780
2762    W    R    K    L    V    D    F    R    E    L    N    K    R    T    Q    NL4-3 genbank.SEQ
2762    TGG  AGA  AAA  TTA  GTA  GAT  TTC  AGA  GAA  CTT  AAT  AAG  AGA  ACT  CAA
2760    W    R    K    L    V    D    F    R    E    L    N    K    R    T    Q    pNL4-3.seq
2760    TGG  AGA  AAA  TTA  GTA  GAT  TTC  AGA  GAA  CTT  AAT  AAG  AGA  ACT  CAA
3287    W    R    K    L    V    D    F    R    E    L    N    K    R    T    Q    pHDMHgpm2.seq
3287    TGG  CGC  AAG  CTG  GTG  GAC  TTC  CGC  GAG  CTG  AAC  AAG  CGC  ACC  CAG 2810                                    2840
2807    D    F    W    E    V    Q    L    G    I    P    H    P    A    G    L    NL4-3 genbank.SEQ
2807    GAT  TTC  TGG  GAA  GTT  CAA  TTA  GGA  ATA  CCA  CAT  CCT  GCA  GGG  TTA
2805    D    F    W    E    V    Q    L    G    I    P    H    P    A    G    L    pNL4-3.seq
2805    GAT  TTC  TGG  GAA  GTT  CAA  TTA  GGA  ATA  CCA  CAT  CCT  GCA  GGG  TTA
3332    D    F    W    E    V    Q    L    G    I    P    H    P    A    G    L    pHDMHgpm2.seq
3332    GAC  TTC  TGG  GAG  GTG  CAG  CTG  GGC  ATC  CCC  CAC  CCC  GCC  GGC  CTG 2870
2852    K    Q    K    K    S    V    T    V    L    D    V    G    D    A    Y    NL4-3 genbank.SEQ
2852    AAA  CAG  AAA  AAA  TCA  GTA  ACA  GTA  CTG  GAT  GTG  GGC  GAT  GCA  TAT
2850    K    Q    K    K    S    V    T    V    L    D    V    G    D    A    Y    pNL4-3.seq
2850    AAA  CAG  AAA  AAA  TCA  GTA  ACA  GTA  CTG  GAT  GTG  GGC  GAT  GCA  TAT
3377    K    Q    K    K    S    V    T    V    L    D    V    G    D    A    Y    pHDMHgpm2.seq
3377    AAG  CAG  AAG  AAG  TCC  GTG  ACC  GTG  CTG  GAC  GTG  GGC  GAC  GCC  TAC
```

Fig. 9C

Alignment Report of Codon Optimization (pol).MEG, using Clustal method with PAM250 residue weight table.

```
         2900                                    2930
2897   F    S    V    P    L    D    K    D    F    R    K    Y    T    A    F    NL4-3 genbank.SEQ
2897  TTT  TCA  GTT  CCC  TTA  GAT  AAA  GAC  TTC  AGG  AAG  TAT  ACT  GCA  TTT
2895   F    S    V    P    L    D    K    D    F    R    K    Y    T    A    F    pNL4-3.seq
2895  TTT  TCA  GTT  CCC  TTA  GAT  AAA  GAC  TTC  AGG  AAG  TAT  ACT  GCA  TTT
3422   F    S    V    P    L    D    K    D    F    R    K    Y    T    A    F    pHDMHgpm2.seq
3422  TTC  TCC  GTG  CCC  CTG  GAC  AAG  GAC  TTC  CGC  AAG  TAC  ACC  GCC  TTC 2960
2942   T    I    P    S    I    N    N    E    T    P    G    I    R    Y    Q    NL4-3 genbank.SEQ
2942  ACC  ATA  CCT  AGT  ATA  AAC  AAT  GAG  ACA  CCA  GGG  ATT  AGA  TAT  CAG
2940   T    I    P    S    I    N    N    E    T    P    G    I    R    Y    Q    pNL4-3.seq
2940  ACC  ATA  CCT  AGT  ATA  AAC  AAT  GAG  ACA  CCA  GGG  ATT  AGA  TAT  CAG
3467   T    I    P    S    I    N    N    E    T    P    G    I    R    Y    Q    pHDMHgpm2.seq
3467  ACC  ATC  CCC  TCC  ATC  AAC  AAC  GAG  ACC  CCC  GGC  ATC  CGC  TAC  CAG 2990                                    3020
2987   Y    N    V    L    P    Q    G    W    K    G    S    P    A    I    F    NL4-3 genbank.SEQ
2987  TAC  AAT  GTG  CTT  CCA  CAG  GGA  TGG  AAA  GGA  TCA  CCA  GCA  ATA  TTC
2985   Y    N    V    L    P    Q    G    W    K    G    S    P    A    I    F    pNL4-3.seq
2985  TAC  AAT  GTG  CTT  CCA  CAG  GGA  TGG  AAA  GGA  TCA  CCA  GCA  ATA  TTC
3512   Y    N    V    L    P    Q    G    W    K    G    S    P    A    I    F    pHDMHgpm2.seq
3512  TAC  AAC  GTG  CTG  CCC  CAG  GGC  TGG  AAG  GGC  TCC  CCC  GCC  ATC  TTC 3050
3032   Q    C    S    M    T    K    I    L    E    P    F    R    K    Q    N    NL4-3 genbank.SEQ
3032  CAG  TGT  AGC  ATG  ACA  AAA  ATC  TTA  GAG  CCT  TTT  AGA  AAA  CAA  AAT
3030   Q    C    S    M    T    K    I    L    E    P    F    R    K    Q    N    pNL4-3.seq
3030  CAG  TGT  AGC  ATG  ACA  AAA  ATC  TTA  GAG  CCT  TTT  AGA  AAA  CAA  AAT
3557   Q    C    S    M    T    K    I    L    E    P    F    R    K    Q    N    pHDMHgpm2.seq
3557  CAG  TGC  TCC  ATG  ACC  AAG  ATC  CTG  GAG  CCC  TTC  CGC  AAG  CAG  AAC 3080                                    3110
3077   P    D    I    V    I    Y    Q    Y    M    D    D    L    Y    V    G    NL4-3 genbank.SEQ
3077  CCA  GAC  ATA  GTC  ATC  TAT  CAA  TAC  ATG  GAT  GAT  TTG  TAT  GTA  GGA
3075   P    D    I    V    I    Y    Q    Y    M    D    D    L    Y    V    G    pNL4-3.seq
3075  CCA  GAC  ATA  GTC  ATC  TAT  CAA  TAC  ATG  GAT  GAT  TTG  TAT  GTA  GGA
3602   P    D    I    V    I    Y    Q    Y    M    D    D    L    Y    V    G    pHDMHgpm2.seq
3602  CCC  GAC  ATC  GTG  ATC  TAC  CAG  TAC  ATG  GAC  GAC  CTG  TAC  GTG  GGC 3140
3122   S    D    L    E    I    G    Q    H    R    T    K    I    E    E    L    NL4-3 genbank.SEQ
3122  TCT  GAC  TTA  GAA  ATA  GGG  CAG  CAT  AGA  ACA  AAA  ATA  GAG  GAA  CTG
3120   S    D    L    E    I    G    Q    H    R    T    K    I    E    E    L    pNL4-3.seq
3120  TCT  GAC  TTA  GAA  ATA  GGG  CAG  CAT  AGA  ACA  AAA  ATA  GAG  GAA  CTG
3647   S    D    L    E    I    G    Q    H    R    T    K    I    E    E    L    pHDMHgpm2.seq
3647  TCC  GAC  CTG  GAG  ATC  GGC  CAG  CAC  CGC  ACC  AAG  ATC  GAG  GAG  CTG
```

Fig. 9D

Alignment Report of Codon Optimization (pol).MEG, using Clustal method with PAM250 residue weight table.

```
              3170                                              3200
3167    R    Q    H    L    L    R    W    G    F    T    T    P    D    K    K    NL4-3 genbank.SEQ
3167   AGA  CAA  CAT  CTG  TTG  AGG  TGG  GGA  TTT  ACC  ACA  CCA  GAC  AAA  AAA
3165    R    Q    H    L    L    R    W    G    F    T    T    P    D    K    K    pNL4-3.seq
3165   AGA  CAA  CAT  CTG  TTG  AGG  TGG  GGA  TTT  ACC  ACA  CCA  GAC  AAA  AAA
3692    R    Q    H    L    L    R    W    G    F    T    T    P    D    K    K    pHDMHgpm2.seq
3692   CGC  CAG  CAC  CTG  CTG  CGC  TGG  GGC  TTC  ACC  ACC  CCC  GAC  AAG  AAG 3230
3212    H    Q    K    E    P    P    F    L    W    M    G    Y    E    L    H    NL4-3 genbank.SEQ
3212   CAT  CAG  AAA  GAA  CCT  CCA  TTC  CTT  TGG  ATG  GGT  TAT  GAA  CTC  CAT
3210    H    Q    K    E    P    P    F    L    W    M    G    Y    E    L    H    pNL4-3.seq
3210   CAT  CAG  AAA  GAA  CCT  CCA  TTC  CTT  TGG  ATG  GGT  TAT  GAA  CTC  CAT
3737    H    Q    K    E    P    P    F    L    W    M    G    Y    E    L    H    pHDMHgpm2.seq
3737   CAC  CAG  AAG  GAG  CCC  CCC  TTC  CTG  TGG  ATG  GGC  TAC  GAG  CTG  CAC 3260                                              3290
3257    P    D    K    W    T    V    Q    P    I    V    L    P    E    K    D    NL4-3 genbank.SEQ
3257   CCT  GAT  AAA  TGG  ACA  GTA  CAG  CCT  ATA  GTG  CTG  CCA  GAA  AAG  GAC
3255    P    D    K    W    T    V    Q    P    I    V    L    P    E    K    D    pNL4-3.seq
3255   CCT  GAT  AAA  TGG  ACA  GTA  CAG  CCT  ATA  GTG  CTG  CCA  GAA  AAG  GAC
3782    P    D    K    W    T    V    Q    P    I    V    L    P    E    K    D    pHDMHgpm2.seq
3782   CCC  GAC  AAG  TGG  ACC  GTG  CAG  CCC  ATC  GTG  CTG  CCC  GAG  AAG  GAC 3320
3302    S    W    T    V    N    D    I    Q    K    L    V    G    K    L    N    NL4-3 genbank.SEQ
3302   AGC  TGG  ACT  GTC  AAT  GAC  ATA  CAG  AAA  TTA  GTG  GGA  AAA  TTG  AAT
3300    S    W    T    V    N    D    I    Q    K    L    V    G    K    L    N    pNL4-3.seq
3300   AGC  TGG  ACT  GTC  AAT  GAC  ATA  CAG  AAA  TTA  GTG  GGA  AAA  TTG  AAT
3827    S    W    T    V    N    D    I    Q    K    L    V    G    K    L    N    pHDMHgpm2.seq
3827   TCC  TGG  ACC  GTG  AAC  GAC  ATC  CAG  AAG  CTG  GTG  GGC  AAG  CTG  AAC 3350                                              3380
3347    W    A    S    Q    I    Y    A    G    I    K    V    R    Q    L    C    NL4-3 genbank.SEQ
3347   TGG  GCA  AGT  CAG  ATT  TAT  GCA  GGG  ATT  AAA  GTA  AGG  CAA  TTA  TGT
3345    W    A    S    Q    I    Y    A    G    I    K    V    R    Q    L    C    pNL4-3.seq
3345   TGG  GCA  AGT  CAG  ATT  TAT  GCA  GGG  ATT  AAA  GTA  AGG  CAA  TTA  TGT
3872    W    A    S    Q    I    Y    A    G    I    K    V    R    Q    L    C    pHDMHgpm2.seq
3872   TGG  GCC  TCC  CAG  ATC  TAC  GCC  GGC  ATC  AAA  GTC  CGC  CAG  CTG  TGC 3410
3392    K    L    L    R    G    T    K    A    L    T    E    V    V    P    L    NL4-3 genbank.SEQ
3392   AAA  CTT  CTT  AGG  GGA  ACC  AAA  GCA  CTA  ACA  GAA  GTA  GTA  CCA  CTA
3390    K    L    L    R    G    T    K    A    L    T    E    V    V    P    L    pNL4-3.seq
3390   AAA  CTT  CTT  AGG  GGA  ACC  AAA  GCA  CTA  ACA  GAA  GTA  GTA  CCA  CTA
3917    K    L    L    R    G    T    K    A    L    T    E    V    V    P    L    pHDMHgpm2.seq
3917   AAG  CTG  CTG  CGC  GGC  ACC  AAG  GCC  CTG  ACC  GAG  GTG  GTG  CCC  CTG
```

Fig. 9E

Alignment Report of Codon Optimization (pol).MEG, using Clustal method with PAM250 residue weight table.

```
          3440                                    3470
3437   T   E   E   A   E   L   E   L   A   E   N   R   E   I   L    NL4-3 genbank.SEQ
3437  ACA GAA GAA GCA GAG CTA GAA CTG GCA GAA AAC AGG GAG ATT CTA
3435   T   E   E   A   E   L   E   L   A   E   N   R   E   I   L    pNL4-3.seq
3435  ACA GAA GAA GCA GAG CTA GAA CTG GCA GAA AAC AGG GAG ATT CTA
3962   T   E   E   A   E   L   E   L   A   E   N   R   E   I   L    pHDMHgpm2.seq
3962  ACC GAG GAG GCC GAG CTG GAG CTG GCC GAG AAC CGC GAG ATC CTG 3500
3482   K   E   P   V   H   G   V   Y   Y   D   P   S   K   D   L    NL4-3 genbank.SEQ
3482  AAA GAA CCG GTA CAT GGA GTG TAT TAT GAC CCA TCA AAA GAC TTA
3480   K   E   P   V   H   G   V   Y   Y   D   P   S   K   D   L    pNL4-3.seq
3480  AAA GAA CCG GTA CAT GGA GTG TAT TAT GAC CCA TCA AAA GAC TTA
4007   K   E   P   V   H   G   V   Y   Y   D   P   S   K   D   L    pHDMHgpm2.seq
4007  AAG GAG CCC GTG CAC GGC GTG TAC TAC GAC CCC TCC AAG GAC CTG 3530                                    3560
3527   I   A   E   I   Q   K   Q   G   Q   G   Q   W   T   Y   Q    NL4-3 genbank.SEQ
3527  ATA GCA GAA ATA CAG AAG CAG GGG CAA GGC CAA TGG ACA TAT CAA
3525   I   A   E   I   Q   K   Q   G   Q   G   Q   W   T   Y   Q    pNL4-3.seq
3525  ATA GCA GAA ATA CAG AAG CAG GGG CAA GGC CAA TGG ACA TAT CAA
4052   I   A   E   I   Q   K   Q   G   Q   G   Q   W   T   Y   Q    pHDMHgpm2.seq
4052  ATC GCC GAG ATC CAG AAG CAG GGC CAG GGC CAG TGG ACC TAC CAG 3590
3572   I   Y   Q   E   P   F   K   N   L   K   T   G   K   Y   A    NL4-3 genbank.SEQ
3572  ATT TAT CAA GAG CCA TTT AAA AAT CTG AAA ACA GGA AAA TAT GCA
3570   I   Y   Q   E   P   F   K   N   L   K   T   G   K   Y   A    pNL4-3.seq
3570  ATT TAT CAA GAG CCA TTT AAA AAT CTG AAA ACA GGA AAA TAT GCA
4097   I   Y   Q   E   P   F   K   N   L   K   T   G   K   Y   A    pHDMHgpm2.seq
4097  ATC TAC CAG GAG CCC TTC AAG AAC CTG AAG ACC GGC AAA TAC GCC 3620                                    3650
3617   R   M   K   G   A   H   T   N   D   V   K   Q   L   T   E    NL4-3 genbank.SEQ
3617  AGA ATG AAG GGT GCC CAC ACT AAT GAT GTG AAA CAA TTA ACA GAG
3615   R   M   K   G   A   H   T   N   D   V   K   Q   L   T   E    pNL4-3.seq
3615  AGA ATG AAG GGT GCC CAC ACT AAT GAT GTG AAA CAA TTA ACA GAG
4142   R   M   K   G   A   H   T   N   D   V   K   Q   L   T   E    pHDMHgpm2.seq
4142  CGC ATG AAG GGC GCC CAC ACC AAC GAC GTG AAG CAG CTG ACC GAG 3680
3662   A   V   Q   K   I   A   T   E   S   I   V   I   W   G   K    NL4-3 genbank.SEQ
3662  GCA GTA CAA AAA ATA GCC ACA GAA AGC ATA GTA ATA TGG GGA AAG
3660   A   V   Q   K   I   A   T   E   S   I   V   I   W   G   K    pNL4-3.seq
3660  GCA GTA CAA AAA ATA GCC ACA GAA AGC ATA GTA ATA TGG GGA AAG
4187   A   V   Q   K   I   A   T   E   S   I   V   I   W   G   K    pHDMHgpm2.seq
4187  GCC GTG CAG AAG ATC GCC ACC GAG TCC ATC GTG ATC TGG GGC AAG
```

Fig. 9F

Alignment Report of Codon Optimization (pol).MEG, using Clustal method with PAM250 residue weight table.

```
             3710                                    3740
3707   T   P   K   F   K   L   P   I   Q   K   E   T   W   E   A    NL4-3 genbank.SEQ
3707  ACT CCT AAA TTT AAA TTA CCC ATA CAA AAG GAA ACA TGG GAA GCA
3705   T   P   K   F   K   L   P   I   Q   K   E   T   W   E   A    pNL4-3.seq
3705  ACT CCT AAA TTT AAA TTA CCC ATA CAA AAG GAA ACA TGG GAA GCA
4232   T   P   K   F   K   L   P   I   Q   K   E   T   W   E   A    pHDMHgpm2.seq
4232  ACT CCC AAG TTC AAG CTG CCC ATC CAG AAG GAG ACC TGG GAG GCC 3770
3752   W   W   T   E   Y   W   Q   A   T   W   I   P   E   W   E    NL4-3 genbank.SEQ
3752  TGG TGG ACA GAG TAT TGG CAA GCC ACC TGG ATT CCT GAG TGG GAG
3750   W   W   T   E   Y   W   Q   A   T   W   I   P   E   W   E    pNL4-3.seq
3750  TGG TGG ACA GAG TAT TGG CAA GCC ACC TGG ATT CCT GAG TGG GAG
4277   W   W   T   E   Y   W   Q   A   T   W   I   P   E   W   E    pHDMHgpm2.seq
4277  TGG TGG ACC GAG TAC TGG CAG GCC ACC TGG ATC CCC GAG TGG GAG 3800                                    3830
3797   F   V   N   T   P   P   L   V   K   L   W   Y   Q   L   E    NL4-3 genbank.SEQ
3797  TTT GTC AAT ACC CCT CCC TTA GTG AAG TTA TGG TAC CAG TTA GAG
3795   F   V   N   T   P   P   L   V   K   L   W   Y   Q   L   E    pNL4-3.seq
3795  TTT GTC AAT ACC CCT CCC TTA GTG AAG TTA TGG TAC CAG TTA GAG
4322   F   V   N   T   P   P   L   V   K   L   W   Y   Q   L   E    pHDMHgpm2.seq
4322  TTC GTG AAC ACC CCC CCC CTG GTG AAG CTG TGG TAC CAG CTG GAG 3860
3842   K   E   P   I   I   G   A   E   T   F   Y   V   D   G   A    NL4-3 genbank.SEQ
3842  AAA GAA CCC ATA ATA GGA GCA GAA ACT TTC TAT GTA GAT GGG GCA
3840   K   E   P   I   I   G   A   E   T   F   Y   V   D   G   A    pNL4-3.seq
3840  AAA GAA CCC ATA ATA GGA GCA GAA ACT TTC TAT GTA GAT GGG GCA
4367   K   E   P   I   I   G   A   E   T   F   Y   V   D   G   A    pHDMHgpm2.seq
4367  AAG GAG CCC ATC ATC GGC GCC GAG ACC TTC TAC GTG GAC GGC GCC 3890                                    3920
3887   A   N   R   E   T   K   L   G   K   A   G   Y   V   T   D    NL4-3 genbank.SEQ
3887  GCC AAT AGG GAA ACT AAA TTA GGA AAA GCA GGA TAT GTA ACT GAC
3885   A   N   R   E   T   K   L   G   K   A   G   Y   V   T   D    pNL4-3.seq
3885  GCC AAT AGG GAA ACT AAA TTA GGA AAA GCA GGA TAT GTA ACT GAC
4412   A   N   R   E   T   K   L   G   K   A   G   Y   V   T   D    pHDMHgpm2.seq
4412  GCC AAC CGC GAG ACC AAG CTG GGC AAG GCC GGC TAC GTG ACC GAC 3950
3932   R   G   R   Q   K   V   V   P   L   T   D   T   T   N   Q    NL4-3 genbank.SEQ
3932  AGA GGA AGA CAA AAA GTT GTC CCC CTA ACG GAC ACA ACA AAT CAG
3930   R   G   R   Q   K   V   V   P   L   T   D   T   T   N   Q    pNL4-3.seq
3930  AGA GGA AGA CAA AAA GTT GTC CCC CTA ACG GAC ACA ACA AAT CAG
4457   R   G   R   Q   K   V   V   P   L   T   D   T   T   N   Q    pHDMHgpm2.seq
4457  CGC GGC CGC CAG AAG GTG GTG CCC CTG ACC GAC ACC ACC AAC CAG
```

Fig. 9G

Alignment Report of Codon Optimization (pol).MEG, using Clustal method with PAM250 residue weight table.

```
            3980                                        4010
3977    K    T    E    L    Q    A    I    H    L    A    L    Q    D    S    G    NL4-3 genbank.SEQ
3977    AAG  ACT  GAG  TTA  CAA  GCA  ATT  CAT  CTA  GCT  TTG  CAG  GAT  TCG  GGA
3975    K    T    E    L    Q    A    I    H    L    A    L    Q    D    S    G    pNL4-3.seq
3975    AAG  ACT  GAG  TTA  CAA  GCA  ATT  CAT  CTA  GCT  TTG  CAG  GAT  TCG  GGA
4502    K    T    E    L    Q    A    I    H    L    A    L    Q    D    S    G    pHDMHgpm2.seq
4502    AAG  ACC  GAG  CTG  CAG  GCC  ATC  CAC  CTG  GCC  CTG  CAA  GAC  TCC  GGC 4040
4022    L    E    V    N    I    V    T    D    S    Q    Y    A    L    G    I    NL4-3 genbank.SEQ
4022    TTA  GAA  GTA  AAC  ATA  GTG  ACA  GAC  TCA  CAA  TAT  GCA  TTG  GGA  ATC
4020    L    E    V    N    I    V    T    D    S    Q    Y    A    L    G    I    pNL4-3.seq
4020    TTA  GAA  GTA  AAC  ATA  GTG  ACA  GAC  TCA  CAA  TAT  GCA  TTG  GGA  ATC
4547    L    E    V    N    I    V    T    D    S    Q    Y    A    L    G    I    pHDMHgpm2.seq
4547    CTG  GAG  GTG  AAC  ATC  GTG  ACC  GAC  TCC  CAG  TAT  GCA  TTG  GGC  ATC 4070                                        4100
4067    I    Q    A    Q    P    D    K    S    E    S    E    L    V    S    Q    NL4-3 genbank.SEQ
4067    ATT  CAA  GCA  CAA  CCA  GAT  AAG  AGT  GAA  TCA  GAG  TTA  GTC  AGT  CAA
4065    I    Q    A    Q    P    D    K    S    E    S    E    L    V    S    Q    pNL4-3.seq
4065    ATT  CAA  GCA  CAA  CCA  GAT  AAG  AGT  GAA  TCA  GAG  TTA  GTC  AGT  CAA
4592    I    Q    A    Q    P    D    K    S    E    S    E    L    V    S    Q    pHDMHgpm2.seq
4592    ATC  CAG  GCC  CAG  CCC  GAC  AAG  TCC  GAG  TCC  GAG  CTG  GTG  TCC  CAG 4130
4112    I    I    E    Q    L    I    K    K    E    K    V    Y    L    A    W    NL4-3 genbank.SEQ
4112    ATA  ATA  GAG  CAG  TTA  ATA  AAA  AAG  GAA  AAA  GTC  TAC  CTG  GCA  TGG
4110    I    I    E    Q    L    I    K    K    E    K    V    Y    L    A    W    pNL4-3.seq
4110    ATA  ATA  GAG  CAG  TTA  ATA  AAA  AAG  GAA  AAA  GTC  TAC  CTG  GCA  TGG
4637    I    I    E    Q    L    I    K    K    E    K    V    Y    L    A    W    pHDMHgpm2.seq
4637    ATC  ATC  GAG  CAG  CTG  ATC  AAG  AAG  GAG  AAG  GTG  TAC  CTG  GCC  TGG 4160                                        4190
4157    V    P    A    H    K    G    I    G    G    N    E    Q    V    D    G    NL4-3 genbank.SEQ
4157    GTA  CCA  GCA  CAC  AAA  GGA  ATT  GGA  GGA  AAT  GAA  CAA  GTA  GAT  GGG
4155    V    P    A    H    K    G    I    G    G    N    E    Q    V    D    K    pNL4-3.seq
4155    GTA  CCA  GCA  CAC  AAA  GGA  ATT  GGA  GGA  AAT  GAA  CAA  GTA  GAT  AAG
4682    V    P    A    H    K    G    I    G    G    N    E    Q    V    D    K    pHDMHgpm2.seq
4682    GTG  CCC  GCC  CAC  AAG  GGC  ATC  GGC  GGC  AAC  GAG  CAG  GTG  GAC  AAG 4220
4202    L    V    S    A    G    I    R    K    V    L    F    L    D    G    I    NL4-3 genbank.SEQ
4202    TTG  GTC  AGT  GCT  GGA  ATC  AGG  AAA  GTA  CTA  TTT  TTA  GAT  GGA  ATA
4200    L    V    S    A    G    I    R    K    V    L    F    L    D    G    I    pNL4-3.seq
4200    TTG  GTC  AGT  GCT  GGA  ATC  AGG  AAA  GTA  CTA  TTT  TTA  GAT  GGA  ATA
4727    L    V    S    A    G    I    R    K    V    L    F    L    D    G    I    pHDMHgpm2.seq
4727    CTG  GTG  TCC  GCC  GGC  ATC  CGC  AAG  GTG  CTG  TTC  CTG  GAC  GGC  ATC
```

Fig. 9H

Alignment Report of Codon Optimization (pol).MEG, using Clustal method with PAM250 residue weight table.

```
             4250                                    4280
             |                                       |
4247   D   K   A   Q   E   E   H   E   K   Y   H   S   N   W   R    NL4-3 genbank.SEQ
4247  GAT AAG GCC CAA GAA GAA CAT GAG AAA TAT CAC AGT AAT TGG AGA
4245   D   K   A   Q   E   E   H   E   K   Y   H   S   N   W   R    pNL4-3.seq
4245  GAT AAG GCC CAA GAA GAA CAT GAG AAA TAT CAC AGT AAT TGG AGA
4772   D   K   A   Q   E   E   H   E   K   Y   H   S   N   W   R    pHDMHgpm2.seq
4772  GAC AAG GCC CAG GAG GAG CAC GAG AAG TAC CAC TCC AAC TGG CGC 4310
                                 |
4292   A   M   A   S   D   F   N   L   P   P   V   V   A   K   E    NL4-3 genbank.SEQ
4292  GCA ATG GCT AGT GAT TTT AAC CTA CCA CCT GTA GTA GCA AAA GAA
4290   A   M   A   S   D   F   N   L   P   P   V   V   A   K   E    pNL4-3.seq
4290  GCA ATG GCT AGT GAT TTT AAC CTA CCA CCT GTA GTA GCA AAA GAA
4817   A   M   A   S   D   F   N   L   P   P   V   V   A   K   E    pHDMHgpm2.seq
4817  GCC ATG GCC TCC GAC TTC AAC CTG CCC CCC GTG GTG GCC AAG GAG 4340                                    4370
             |                                       |
4337   I   V   A   S   C   D   K   C   Q   L   K   G   E   A   M    NL4-3 genbank.SEQ
4337  ATA GTA GCC AGC TGT GAT AAA TGT CAG CTA AAA GGG GAA GCC ATG
4335   I   V   A   S   C   D   K   C   Q   L   K   G   E   A   M    pNL4-3.seq
4335  ATA GTA GCC AGC TGT GAT AAA TGT CAG CTA AAA GGG GAA GCC ATG
4862   I   V   A   S   C   D   K   C   Q   L   K   G   E   A   M    pHDMHgpm2.seq
4862  ATC GTG GCC TCC TGC GAC AAG TGC CAG CTG AAG GGC GAG GCC ATG 4400
                             |
4382   H   G   Q   V   D   C   S   P   G   I   W   Q   L   D   C    NL4-3 genbank.SEQ
4382  CAT GGA CAA GTA GAC TGT AGC CCA GGA ATA TGG CAG CTA GAT TGT
4380   H   G   Q   V   D   C   S   P   G   I   W   Q   L   D   C    pNL4-3.seq
4380  CAT GGA CAA GTA GAC TGT AGC CCA GGA ATA TGG CAG CTA GAT TGT
4907   H   G   Q   V   D   C   S   P   G   I   W   Q   L   D   C    pHDMHgpm2.seq
4907  CAC GGC CAG GTG GAC TGC TCC CCC GGC ATC TGG CAG CTG GAC TGC 4430                                    4460
             |                                       |
4427   T   H   L   E   G   K   V   I   L   V   A   V   H   V   A    NL4-3 genbank.SEQ
4427  ACA CAT TTA GAA GGA AAA GTT ATC TTG GTA GCA GTT CAT GTA GCC
4425   T   H   L   E   G   K   V   I   L   V   A   V   H   V   A    pNL4-3.seq
4425  ACA CAT TTA GAA GGA AAA GTT ATC TTG GTA GCA GTT CAT GTA GCC
4952   T   H   L   E   G   K   V   I   L   V   A   V   H   V   A    pHDMHgpm2.seq
4952  ACC CAC CTG GAG GGC AAG GTG ATC CTG GTG GCC GTG CAC GTG GCC 4490
                         |
4472   S   G   Y   I   E   A   E   V   I   P   A   E   T   G   Q    NL4-3 genbank.SEQ
4472  AGT GGA TAT ATA GAA GCA GAA GTA ATT CCA GCA GAG ACA GGG CAA
4470   S   G   Y   I   E   A   E   V   I   P   A   E   T   G   Q    pNL4-3.seq
4470  AGT GGA TAT ATA GAA GCA GAA GTA ATT CCA GCA GAG ACA GGG CAA
4997   S   G   Y   I   E   A   E   V   I   P   A   E   T   G   Q    pHDMHgpm2.seq
4997  TCC GGC TAC ATC GAG GCC GAG GTG ATC CCC GCC GAG ACC GGC CAG
```

Fig. 9I

Alignment Report of Codon Optimization (pol).MEG, using Clustal method with PAM250 residue weight table.

```
       4520                                     4550
4517   E   T   A   Y   F   L   L   K   L   A   G   R   W   P   V   NL4-3 genbank.SEQ
4517   GAA ACA GCA TAC TTC CTC TTA AAA TTA GCA GGA AGA TGG CCA GTA
4515   E   T   A   Y   F   L   L   K   L   A   G   R   W   P   V   pNL4-3.seq
4515   GAA ACA GCA TAC TTC CTC TTA AAA TTA GCA GGA AGA TGG CCA GTA
5042   E   T   A   Y   F   L   L   K   L   A   G   R   W   P   V   pHDMHgpm2.seq
5042   GAG ACC GCC TAC TTC CTG CTG AAG CTG GCC GGC CGC TGG CCC GTG 4580
4562   K   T   V   H   T   D   N   G   S   N   F   T   S   T   T   NL4-3 genbank.SEQ
4562   AAA ACA GTA CAT ACA GAC AAT GGC AGC AAT TTC ACC AGT ACT ACA
4560   K   T   V   H   T   D   N   G   S   N   F   T   S   T   T   pNL4-3.seq
4560   AAA ACA GTA CAT ACA GAC AAT GGC AGC AAT TTC ACC AGT ACT ACA
5087   K   T   V   H   T   D   N   G   S   N   F   T   S   T   T   pHDMHgpm2.seq
5087   AAG ACC GTG CAC ACC GAC AAC GGC TCC AAC TTC ACC TCC ACC ACC 4610                                     4640
4607   V   K   A   A   C   W   W   A   G   I   K   Q   E   F   G   NL4-3 genbank.SEQ
4607   GTT AAG GCC GCC TGT TGG TGG GCG GGG ATC AAG CAG GAA TTT GGC
4605   V   K   A   A   C   W   W   A   G   I   K   Q   E   F   G   pNL4-3.seq
4605   GTT AAG GCC GCC TGT TGG TGG GCG GGG ATC AAG CAG GAA TTT GGC
5132   V   K   A   A   C   W   W   A   G   I   K   Q   E   F   G   pHDMHgpm2.seq
5132   GTG AAG GCC GCC TGC TGG TGG GCC GGC ATC AAG CAG GAG TTC GGC 4670
4652   I   P   Y   N   P   Q   S   Q   G   V   I   E   S   M   N   NL4-3 genbank.SEQ
4652   ATT CCC TAC AAT CCC CAA AGT CAA GGA GTA ATA GAA TCT ATG AAT
4650   I   P   Y   N   P   Q   S   Q   G   V   I   E   S   M   N   pNL4-3.seq
4650   ATT CCC TAC AAT CCC CAA AGT CAA GGA GTA ATA GAA TCT ATG AAT
5177   I   P   Y   N   P   Q   S   Q   G   V   I   E   S   M   N   pHDMHgpm2.seq
5177   ATC CCC TAC AAC CCC CAG TCC CAG GGC GTG ATC GAG TCC ATG AAC 4700                                     4730
4697   K   E   L   K   K   I   I   G   Q   V   R   D   Q   A   E   NL4-3 genbank.SEQ
4697   AAA GAA TTA AAG AAA ATT ATA GGA CAG GTA AGA GAT CAG GCT GAA
4695   K   E   L   K   K   I   I   G   Q   V   R   D   Q   A   E   pNL4-3.seq
4695   AAA GAA TTA AAG AAA ATT ATA GGA CAG GTA AGA GAT CAG GCT GAA
5222   K   E   L   K   K   I   I   G   Q   V   R   D   Q   A   E   pHDMHgpm2.seq
5222   AAG GAG CTG AAG AAG ATC ATC GGC CAA GTC CGC GAC CAG GCC GAG 4760
4742   H   L   K   T   A   V   Q   M   A   V   F   I   H   N   F   NL4-3 genbank.SEQ
4742   CAT CTT AAG ACA GCA GTA CAA ATG GCA GTA TTC ATC CAC AAT TTT
4740   H   L   K   T   A   V   Q   M   A   V   F   I   H   N   F   pNL4-3.seq
4740   CAT CTT AAG ACA GCA GTA CAA ATG GCA GTA TTC ATC CAC AAT TTT
5267   H   L   K   T   A   V   Q   M   A   V   F   I   H   N   F   pHDMHgpm2.seq
5267   CAC CTG AAG ACC GCC GTG CAG ATG GCC GTG TTC ATC CAC AAC TTC
```

Fig. 9J

Alignment Report of Codon Optimization (pol).MEG, using Clustal method with PAM250 residue weight table.

```
          4790                              4820
4787   K    R    K    G    G    I    G    G    Y    S    A    G    E    R    I    NL4-3 genbank.SEQ
4787  AAA  AGA  AAA  GGG  GGG  ATT  GGG  GGG  TAC  AGT  GCA  GGG  GAA  AGA  ATA
4785   K    R    K    G    G    I    G    G    Y    S    A    G    E    R    I    pNL4-3.seq
4785  AAA  AGA  AAA  GGG  GGG  ATT  GGG  GGG  TAC  AGT  GCA  GGG  GAA  AGA  ATA
5312   K    R    K    G    G    I    G    G    Y    S    A    G    E    R    I    pHDMHgpm2.seq
5312  AAG  CGC  AAG  GGC  GGC  ATC  GGC  GGC  TAC  TCC  GCC  GGC  GAG  CGC  ATC 4850
4832   V    D    I    I    A    T    D    I    Q    T    K    E    L    Q    K    NL4-3 genbank.SEQ
4832  GTA  GAC  ATA  ATA  GCA  ACA  GAC  ATA  CAA  ACT  AAA  GAA  TTA  CAA  AAA
4830   V    D    I    I    A    T    D    I    Q    T    K    E    L    Q    K    pNL4-3.seq
4830  GTA  GAC  ATA  ATA  GCA  ACA  GAC  ATA  CAA  ACT  AAA  GAA  TTA  CAA  AAA
5357   V    D    I    I    A    T    D    I    Q    T    K    E    L    Q    K    pHDMHgpm2.seq
5357  GTG  GAC  ATC  ATC  GCC  ACC  GAC  ATC  CAG  ACC  AAG  GAG  CTG  CAG  AAG 4880                              4910
4877   Q    I    T    K    I    Q    N    F    R    V    Y    Y    R    D    S    NL4-3 genbank.SEQ
4877  CAA  ATT  ACA  AAA  ATT  CAA  AAT  TTT  CGG  GTT  TAT  TAC  AGG  GAC  AGC
4875   Q    I    T    K    I    Q    N    F    R    V    Y    Y    R    D    S    pNL4-3.seq
4875  CAA  ATT  ACA  AAA  ATT  CAA  AAT  TTT  CGG  GTT  TAT  TAC  AGG  GAC  AGC
5402   Q    I    T    K    I    Q    N    F    R    V    Y    Y    R    D    S    pHDMHgpm2.seq
5402  CAG  ATC  ACC  AAG  ATC  CAG  AAC  TTC  CGC  GTG  TAC  TAC  CGC  GAC  TCC 4940
4922   R    D    P    V    W    K    G    P    A    K    L    L    W    K    G    NL4-3 genbank.SEQ
4922  AGA  GAT  CCA  GTT  TGG  AAA  GGA  CCA  GCA  AAG  CTC  CTC  TGG  AAA  GGT
4920   R    D    P    V    W    K    G    P    A    K    L    L    W    K    G    pNL4-3.seq
4920  AGA  GAT  CCA  GTT  TGG  AAA  GGA  CCA  GCA  AAG  CTC  CTC  TGG  AAA  GGT
5447   R    D    P    V    W    K    G    P    A    K    L    L    W    K    G    pHDMHgpm2.seq
5447  CGC  GAC  CCC  GTG  TGG  AAG  GGC  CCC  GCC  AAG  CTG  CTG  TGG  AAG  GGC 4970                              5000
4967   E    G    A    V    V    I    Q    D    N    S    D    I    K    V    V    NL4-3 genbank.SEQ
4967  GAA  GGG  GCA  GTA  GTA  ATA  CAA  GAT  AAT  AGT  GAC  ATA  AAA  GTA  GTG
4965   E    G    A    V    V    I    Q    D    N    S    D    I    K    V    V    pNL4-3.seq
4965  GAA  GGG  GCA  GTA  GTA  ATA  CAA  GAT  AAT  AGT  GAC  ATA  AAA  GTA  GTG
5492   E    G    A    V    V    I    Q    D    N    S    D    I    K    V    V    pHDMHgpm2.seq
5492  GAG  GGC  GCC  GTG  GTG  ATC  CAG  GAC  AAC  TCC  GAC  ATC  AAG  GTG  GTG 5030
5012   P    R    R    K    A    K    I    I    R    D    Y    G    K    Q    M    NL4-3 genbank.SEQ
5012  CCA  AGA  AGA  AAA  GCA  AAG  ATC  ATC  AGG  GAT  TAT  GGA  AAA  CAG  ATG
5010   P    R    R    K    A    K    I    I    R    D    Y    G    K    Q    M    pNL4-3.seq
5010  CCA  AGA  AGA  AAA  GCA  AAG  ATC  ATC  AGG  GAT  TAT  GGA  AAA  CAG  ATG
5537   P    R    R    K    A    K    I    I    R    D    Y    G    K    Q    M    pHDMHgpm2.seq
5537  CCC  CGC  CGC  AAG  GCC  AAG  ATC  ATC  CGC  GAC  TAC  GGC  AAG  CAG  ATG
```

Fig. 9K

Alignment Report of Codon Optimization (pol).MEG, using Clustal method with PAM250 residue weight table.

```
         5060                                        5090
5057   A   G   D   D   C   V   A   S   R   Q   D   E   D           NL4-3 genbank.SEQ
5057  GCA GGT GAT GAT TGT GTG GCA AGT AGA CAG GAT GAG GAT TAA
5055   A   G   D   D   C   V   A   S   R   Q   D   E   D           pNL4-3.seq
5055  GCA GGT GAT GAT TGT GTG GCA AGT AGA CAG GAT GAG GAT TAA
5582   A   G   D   D   C   V   A   S   R   Q   D   E   D           pHDMHgpm2.seq
5582  GCC GGC GAC GAC TGC GTG GCC TCC CGC CAG GAC GAG GAC TAA
```

Fig. 9L

```
AGCTTGGCCC ATTGCATACG TTGTATCCAT ATCATAATAT GTACATTTAT ATTGGCTCAT    60
GTCCAACATT ACCGCCATGT TGACATTGAT TATTGACTAG TTATTAATAG TAATCAATTA   120
CGGGGTCATT AGTTCATAGC CCATATATGG AGTTCCGCGT TACATAACTT ACGGTAAATG   180
GCCCGCCTGG CTGACCGCCC AACGACCCCC GCCCATTGAC GTCAATAATG ACGTATGTTC   240
CCATAGTAAC GCCAATAGGG ACTTTCCATT GACGTCAATG GGTGGAGTAT TTACGGTAAA   300
CTGCCCACTT GGCAGTACAT CAAGTGTATC ATATGCCAAG TACGCCCCCT ATTGACGTCA   360
ATGACGGTAA ATGGCCCGCC TGGCATTATG CCCAGTACAT GACCTTATGG GACTTTCCTA   420
CTTGGCAGTA CATCTACGTA TTAGTCATCG CTATTACCAT GGTGATGCGG TTTTGGCAGT   480
ACATCAATGG GCGTGGATAG CGGTTTGACT CACGGGGATT TCCAAGTCTC CACCCCATTG   540
ACGTCAATGG GAGTTTGTTT TGGCACCAAA ATCAACGGGA CTTTCCAAAA TGTCGTAACA   600
ACTCCGCCCC ATTGACGCAA ATGGGCGGTA GGCGTGTACG GTGGGAGGTC TATATAAGCA   660
GAGCTCGTTT AGTGAACCGT CAGATCGCCT GGAGACGCCA TCCACGCTGT TTTGACCTCC   720
ATAGAAGACA CCGGGACCGA TCCAGCCTCC CCTCGAAGCT GATCCTGAGA ACTTCAGGGT   780
GAGTCTATGG GACCCTTGAT GTTTTCTTTC CCCTTCTTTT CTATGGTTAA GTTCATGTCA   840
TAGGAAGGGG AGAAGTAACA GGGTACACAT ATTGACCAAA TCAGGGTAAT TTTGCATTTG   900
TAATTTTAAA AAATGCTTTC TTCTTTTAAT ATACTTTTTT GTTTATCTTA TTTCTAATAC   960
TTTCCCTAAT CTCTTTCTTT CAGGGCAATA ATGATACAAT GTATCATGCC TCTTTGCACC  1020
ATTCTAAAGA ATAACAGTGA TAATTTCTGG GTTAAGGCAA TAGCAATATT CTGCATATA  1080
AATATTTCTG CATATAAATT GTAACTGATG TAAGAGGTTT CATATTGCTA ATAGCAGCTA  1140
CAATCCAGCT ACCATTCTGC TTTTATTTTA TGGTTGGGAT AAGGCTGGAT TATTCTGAGT  1200
CCAAGCTAGG CCCTTTTGCT AATCATGTTC ATACCTCTTA TCTTCCTCCC ACAGCTCCTG  1260
GGCAACGTGC TGGTCTGTGT GCTGGCCCAT CACTTTGGCA AAGAATTCTA GACTGCCATG  1320
GGCGCCCGCG CCTCCGTGCT GTCCGGCGGC GAGCTGGACA AGTGGGAGAA GATCCGCCTG  1380
CGCCCCGGCG GCAAGAAGCA GTACAAGCTG AAGCACATCG TGTGGGCCTC CCGCGAGCTG  1440
GAGCGCTTCG CCGTGAACCC CGGCCTGCTG GAGACCTCCG AGGGCTGCCG CCAGATCCTG  1500
GGCCAGCTGC AGCCCTCCCT GCAAACCGGC TCCGAGGAGC TGCGCTCCCT GTACAACACC  1560
ATCGCCGTGC TGTACTGCGT GCACCAGCGC ATCGACGTGA AGGACACCAA GGAGGCCCTG  1620
GACAAGATCG AGGAGGAGCA GAACAAGTCC AAGAAGAAGG CCCAGCAGGC CGCCGCCGAC  1680
ACCGGCAACA ACTCCCAGGT GTCCCAGAAC TACCCCATCG TGCAGAACCT GCAGGGCCAG  1740
ATGGTGCACC AGGCCATCTC CCCCCGCACC CTGAACGCCT GGGTGAAGGT GGTGGAGGAG  1800
AAGGCCTTCT CCCCCGAAGT CATCCCCATG TTCTCCGCCC TGTCCGAGGG CGCCACCCCC  1860
CAGGACCTGA ACACCATGCT GAACACCGTG GGCGGCCACC AGGCCGCCAT GCAGATGCTG  1920
AAGGAGACCA TCAACGAGGA GGCCGCCGAG TGGGACCGCC TGCACCCCGT GCACGCCGGC  1980
CCCATCGCCC CCGGCCAGAT GCGCGAGCCC CGCGGCTCCG ACATCGCCGG CACCACCTCC  2040
ACCCTGCAAG AGCAGATCGG CTGGATGACC CACAACCCCC CCATCCCCGT GGGCGAGATC  2100
TACAAGCGCT GGATCATCCT GGGCCTGAAC AAGATCGTGC GCATGTACTC CCCCACCTCC  2160
ATCCTGGACA TCCGCCAGGG CCCCAAGGAG CCCTTCCGCG ACTACGTGGA CCGCTTCTAC  2220
AAGACCCTGC GCGCCGAGCA GGCCTCCCAG GAGGTAAAGA ACTGGATGAC CGAGACCCTG  2280
CTGGTGCAGA ACGCCAACCC CGACTGCAAG ACCATCCTGA AGGCCCTGGG CCCCGGCGCC  2340
ACCCTGGAGG AGATGATGAC CGCCTGCCAG GGCGTGGGCG GCCCCGGCCA CAAGGCCCGC  2400
GTGCTGGCCG AGGCCATGTC CCAAGTCACC AACCCCGCCA CCATCATGAT CCAGAAGGGC  2460
AACTTCCGCA ACCAGCGCAA GACCGTGAAG TGCTTCAACT GCGGCAAGGA GGGCCACATC  2520
GCCAAGAACT GCCGCGCCCC CCGCAAGAAG GGCTGCTGGA AGTGCGGCAA GGAGGGCCAC  2580
CAGATGAAAG ATTGTACTGA GAGACAGGCT AATTTTTTAG GGAAGATCTG GCCTTCCCAC  2640
AAGGGAAGGC CAGGGAATTT TCTTCAGAGC AGACCAGAGC AACAGCCCC ACCAGAAGAG  2700
AGCTTCAGGT TTGGGGAAGA GACAACAACT CCCTCTCAGA AGCAGGAGCC GATAGACAAG  2760
GAACTGTATC CTTTAGCTTC CCTCAGATCA CTCTTTGGCA GCGACCCCTC GTCACAATAA  2820
```

Fig. 10A

```
AGATCGGTGG CCAGCTGAAG GAGGCCCTGC TGGACACCGG CGCCGACGAC ACCGTGCTGG  2880
AGGAGATGAA CCTGCCCGGC CGCTGGAAGC CCAAGATGAT CGGCGGCATC GGCGGCTTCA  2940
TCAAAGTCCG CCAGTACGAC CAGATCCTGA TCGAGATCTG CGGCCACAAG GCCATCGGCA  3000
CCGTGCTGGT GGGCCCCACC CCCGTGAACA TCATCGGCCG CAACCTGCTG ACCCAGATCG  3060
GCTGCACCCT GAACTTCCCC ATCTCCCCCA TCGAGACCGT GCCCGTGAAG CTGAAGCCCG  3120
GCATGGACGG CCCCAAAGTC AAGCAGTGGC CCCTGACCGA GGAGAAGATC AAGGCCCTGG  3180
TGGAGATCTG CACCGAGATG GAGAAGGAGG GCAAGATCTC CAAGATCGGC CCGAGAACC   3240
CCTACAACAC CCCCGTGTTC GCCATCAAGA AGAAGGACTC CACCAAGTGG CGCAAGCTGG  3300
TGGACTTCCG CGAGCTGAAC AAGCGCACCC AGGACTTCTG GGAGGTGCAG CTGGGCATCC  3360
CCCACCCCGC CGGCCTGAAG CAGAAGAAGT CCGTGACCGT GCTGGACGTG GGCGACGCCT  3420
ACTTCTCCGT GCCCCTGGAC AAGGACTTCC GCAAGTACAC CGCCTTCACC ATCCCCTCCA  3480
TCAACAACGA GACCCCCGGC ATCCGCTACC AGTACAACGT GCTGCCCCAG GGCTGGAAGG  3540
GCTCCCCCGC CATCTTCCAG TGCTCCATGA CCAAGATCCT GGAGCCCTTC CGCAAGCAGA  3600
ACCCCGACAT CGTGATCTAC CAGTACATGG ACGACCTGTA CGTGGGCTCC GACCTGGAGA  3660
TCGGCCAGCA CCGCACCAAG ATCGAGGAGC TGCGCCAGCA CCTGCTGCGC TGGGGCTTCA  3720
CCACCCCCGA CAAGAAGCAC CAGAAGGAGC CCCCCTTCCT GTGGATGGGC TACGAGCTGC  3780
ACCCCGACAA GTGGACCGTG CAGCCCATCG TGCTGCCCGA GAAGGACTCC TGGACCGTGA  3840
ACGACATCCA GAAGCTGGTG GGCAAGCTGA ACTGGGCCTC CCAGATCTAC GCCGGCATCA  3900
AAGTCCGCCA GCTGTGCAAG CTGCTGCGCG GCACCAAGGC CCTGACCGAG GTGGTGCCCC  3960
TGACCGAGGA GGCCGAGCTG GAGCTGGCCG AGAACCGCGA GATCCTGAAG GAGCCCGTGC  4020
ACGGCGTGTA CTACGACCCC TCCAAGGACC TGATCGCCGA GATCCAGAAG CAGGGCCAGG  4080
GCCAGTGGAC CTACCAGATC TACCAGGAGC CCTTCAAGAA CCTGAAGACC GGCAAATACG  4140
CCCGCATGAA GGGCGCCCAC ACCAACGACG TGAAGCAGCT GACCGAGGCC GTGCAGAAGA  4200
TCGCCACCGA GTCCATCGTG ATCTGGGGCA AGACTCCCAA GTTCAAGCTG CCCATCCAGA  4260
AGGAGACCTG GGAGGCCTGG TGGACCGAGT ACTGGCAGGC CACCTGGATC CCCGAGTGGG  4320
AGTTCGTGAA CACCCCCCCC CTGGTGAAGC TGTGGTACCA GCTGGAGAAG GAGCCCATCA  4380
TCGGCGCCGA GACCTTCTAC GTGGACGGCG CCGCCAACCG CGAGACCAAG CTGGGCAAGG  4440
CCGGCTACGT GACCGACCGC GGCCGCCAGA AGGTGGTGCC CCTGACCGAC ACCACCAACC  4500
AGAAGACCGA GCTGCAGGCC ATCCACCTGG CCCTGCAAGA CTCCGGCCTG GAGGTGAACA  4560
TCGTGACCGA CTCCCAGTAT GCATTGGGCA TCATCCAGGC CCAGCCCGAC AAGTCCGAGT  4620
CCGAGCTGGT GTCCCAGATC ATCGAGCAGC TGATCAAGAA GGAGAAGGTG TACCTGGCCT  4680
GGGTGCCCGC CCACAAGGGC ATCGGCGGCA ACGAGCAGGT GGACAAGCTG GTGTCCGCCG  4740
GCATCCGCAA GGTGCTGTTC CTGGACGGCA TCGACAAGGC CCAGGAGGAG CACGAGAAGT  4800
ACCACTCCAA CTGGCGCGCC ATGGCCTCCG ACTTCAACCT GCCCCCCGTG GTGGCCAAGG  4860
AGATCGTGGC CTCCTGCGAC AAGTGCCAGC TGAAGGGCGA GGCCATGCAC GGCCAGGTGG  4920
ACTGCTCCCC CGGCATCTGG CAGCTGGACT GCACCCACCT GGAGGGCAAG GTGATCCTGG  4980
TGGCCGTGCA CGTGGCCTCC GGCTACATCG AGGCCGAGGT GATCCCCGCC GAGACCGGCC  5040
AGGAGACCGC CTACTTCCTG CTGAAGCTGG CCGGCCGCTG GCCCGTGAAG ACCGTGCACA  5100
CCGACAACGG CTCCAACTTC ACCTCCACCA CCGTGAAGGC CGCCTGCTGG TGGGCCGGCA  5160
TCAAGCAGGA GTTCGGCATC CCCTACAACC CCCAGTCCCA GGGCGTGATC GAGTCCATGA  5220
ACAAGGAGCT GAAGAAGATC ATCGGCCAAG TCCGCGACCA GGCCGAGCAC CTGAAGACCG  5280
CCGTGCAGAT GGCCGTGTTC ATCCACAACT TCAAGCGCAA GGGCGGCATC GGCGGCTACT  5340
CCGCCGGCGA GCGCATCGTG GACATCATCG CCACCGACAT CCAGACCAAG GAGCTGCAGA  5400
AGCAGATCAC CAAGATCCAG AACTTCCGCG TGTACTACCG CGACTCCGC GACCCCGTGT  5460
GGAAGGGCCC CGCCAAGCTG CTGTGGAAGG GCGAGGGCGC CGTGGTGATC CAGGACAACT  5520
CCGACATCAA GGTGGTGCCC CGCCGCAAGG CCAAGATCAT CCGCGACTAC GGCAAGCAGA  5580
TGGCCGGCGA CGACTGCGTG GCCTCCCGCC AGGACGAGGA CTAACACATG GAAAAGATTA  5640
```

Fig. 10B

```
GTAAAACACC ATAGGCCGCT CTAGAGGATC CAAGCTTATC GATACCGTCG ACCTCGAGGG  5700
CCCAGATCTA ATTCACCCCA CCAGTGCAGG CTGCCTATCA GAAAGTGGTG GCTGGTGTGG  5760
CTAATGCCCT GGCCCACAAG TATCACTAAG CTCGCTTTCT TGCTGTCCAA TTTCTATTAA  5820
AGGTTCCTTT GTTCCCTAAG TCCAACTACT AAACTGGGGG ATATTATGAA GGGCCTTGAG  5880
CATCTGGATT CTGCCTAATA AAAACATTT ATTTTCATTG CAATGATGTA TTTAAATTAT  5940
TTCTGAATAT TTTACTAAAA AGGGAATGTG GGAGGTCAGT GCATTTAAAA CATAAAGAAA  6000
TGAAGAGCTA GTTCAAACCT TGGGAAAATA CACTATATCT TAAACTCCAT GAAAGAAGGT  6060
GAGGCTGCAA ACAGCTAATG CACATTGGCA ACAGCCCCTG ATGCCTATGC CTTATTCATC  6120
CCTCAGAAAA GGATTCAAGT AGAGGCTTGA TTTGGAGGTT AAAGTTTTGC TATGCTGTAT  6180
TTTACATTAC TTATTGTTTT AGCTGTCCTC ATGAATGTCT TTTCACTACC CATTTGCTTA  6240
TCCTGCATCT CTCAGCCTTG ACTCCACTCA GTTCTCTTGC TTAGAGATAC CACCTTTCCC  6300
CTGAAGTGTT CCTTCCATGT TTTACGGCGA GATGGTTTCT CCTCGCCTGG CCACTCAGCC  6360
TTAGTTGTCT CTGTTGTCTT ATAGAGGTCT ACTTGAAGAA GGAAAAACAG GGGGCATGGT  6420
TTGACTGTCC TGTGAGCCCT TCTTCCCTGC CTCCCCCACT CACAGTGACC CGGAATCCCT  6480
CGACATGGCA GTCTAGATCA TTCTTGAAGA CGAAAGGGCC TCGTGATACG CCTATTTTTA  6540
TAGGTTAATG TCATGATAAT AATGGTTTCT TAGACGTCAG GTGGCACTTT TCGGGGAAAT  6600
GTGCGCGGAA CCCCTATTTG TTTATTTTTC TAAATACATT CAAATATGTA TCCGCTCATG  6660
AGACAATAAC CCTGATAAAT GCTTCAATAA TATTGAAAAA GGAAGAGTAT GAGTATTCAA  6720
CATTTCCGTG TCGCCCTTAT TCCCTTTTTT GCGGCATTTT GCCTTCCTGT TTTTGCTCAC  6780
CCAGAAACGC TGGTGAAAGT AAAAGATGCT GAAGATCAGT TGGGTGCACG AGTGGGTTAC  6840
ATCGAACTGG ATCTCAACAG CGGTAAGATC CTTGAGAGTT TTCGCCCCGA AGAACGTTTT  6900
CCAATGATGA GCACTTTTAA AGTTCTGCTA TGTGGCGCGG TATTATCCCG TATTGACGCC  6960
GGGCAAGAGC AACTCGGTCG CCGCATACAC TATTCTCAGA ATGACTTGGT TGAGTACTCA  7020
CCAGTCACAG AAAAGCATCT TACGGATGGC ATGACAGTAA GAGAATTATG CAGTGCTGCC  7080
ATAACCATGA GTGATAACAC TGCGGCCAAC TTACTTCTGA CAACGATCGG AGGACCGAAG  7140
GAGCTAACCG CTTTTTTGCA CAACATGGGG GATCATGTAA CTCGCCTTGA TCGTTGGGAA  7200
CCGGAGCTGA ATGAAGCCAT ACCAAACGAC GAGCGTGACA CCACGATGCC TGTAGCAATG  7260
GCAACAACGT TGCGCAAACT ATTAACTGGC GAACTACTTA CTCTAGCTTC CCGGCAACAA  7320
TTAATAGACT GGATGGAGGC GGATAAAGTT GCAGGACCAC TTCTGCGCTC GGCCCTTCCG  7380
GCTGGCTGGT TTATTGCTGA TAAATCTGGA GCCGGTGAGC GTGGGTCTCG CGGTATCATT  7440
GCAGCACTGG GGCCAGATGG TAAGCCCTCC CGTATCGTAG TTATCTACAC GACGGGGAGT  7500
CAGGCAACTA TGGATGAACG AAATAGACAG ATCGCTGAGA TAGGTGCCTC ACTGATTAAG  7560
CATTGGTAAC TGTCAGACCA AGTTTACTCA TATATACTTT AGATTGATTT AAAACTTCAT  7620
TTTTAATTTA AAAGGATCTA GGTGAAGATC CTTTTTGATA ATCTCATGAC CAAAATCCCT  7680
TAACGTGAGT TTTCGTTCCA CTGAGCGTCA GACCCCGTAG AAAAGATCAA AGGATCTTCT  7740
TGAGATCCTT TTTTTCTGCG CGTAATCTGC TGCTTGCAAA CAAAAAAACC ACCGCTACCA  7800
GCGGTGGTTT GTTTGCCGGA TCAAGAGCTA CCAACTCTTT TTCCGAAGGT AACTGGCTTC  7860
AGCAGAGCGC AGATACCAAA TACTGTTCTT CTAGTGTAGC CGTAGTTAGG CCACCACTTC  7920
AAGAACTCTG TAGCACCGCC TACATACCTC GCTCTGCTAA TCCTGTTACC AGTGGCTGCT  7980
GCCAGTGGCG ATAAGTCGTG TCTTACCGGG TTGGACTCAA GACGATAGTT ACCGGATAAG  8040
GCGCAGCGGT CGGGCTGAAC GGGGGGTTCG TGCACACAGC CCAGCTTGGA GCGAACGACC  8100
TACACCGAAC TGAGATACCT ACAGCGTGAG CTATGAGAAA GCGCCACGCT TCCCGAAGGG  8160
AGAAAGGCGG ACAGGTATCC GGTAAGCGGC AGGGTCGGAA CAGGAGAGCG CACGAGGGAG  8220
CTTCCAGGGG GAAACGCCTG GTATCTTTAT AGTCCTGTCG GGTTTCGCCA CCTCTGACTT  8280
GAGCGTCGAT TTTTGTGATG CTCGTCAGGG GGCGGAGCC TATGGAAAAA CGCCAGCAAC  8340
GGATGCGCCG CGTGCGGCTG CTGGAGATGG CGGACGCGAT GGATATGTTC TGCCAAGGGT  8400
TGGTTTGCGC ATTCACAGTT CTCCGCAAGA ATTGATTGGC TCCAATTCTT GGAGTGGTGA  8460
```

Fig. 10C

```
ATCCGTTAGC GAGGTGCCGC CGGCTTCCAT TCAGGTCGAG GTGGCCCGGC TCCATGCACC  8520
GCGACGCAAC GCGGGGAGGC AGACAAGGTA TAGGGCGGCG CCTACAATCC ATGCCAACCC  8580
GTTCCATGTG CTCGCCGAGG CGGCATAAAT CCCCGTGACG ATCAGCGGTC CAATGATCGA  8640
AGTTAGGCTG GTAAGAGCCG CGAGCGATCC TTGAAGCTGT CCCTGATGGT CGTCATCTAC  8700
CTGCCTGGAC AGCATGGCCT GCAACGCGGG CATCCCGATG CCGCCGGAAG CGAGAAGAAT  8760
CATAATGGGG AAGGCCATCC AGCCTCGCGT CGGGGAGCTT TTTGCAAAAG CCTAGGCCTC  8820
CAAAAAAGCC TCCTCACTAC TTCTGGAATA GCTCAGAGGC CGAGGCGGCC TCGGCCTCTG  8880
CATAAATAAA AAAAATTAGT CAGCCATG  8908
```

PACKAGING CELLS COMPRISING CODON-OPTIMIZED *GAGPOL* SEQUENCES AND LACKING LENTIVIRAL ACCESSORY PROTEINS

RELATED APPLICATIONS

This application claims the benefit of U.S. Provisional Application No. 60/100,063, filed Sep. 12, 1998 and U.S. Provisional Application No. 60/100,022, filed Sep. 11, 1998, the contents of which are incorporated herein by reference in their entirety.

BACKGROUND OF THE INVENTION

Retroviral vectors based on lentiviruses, such as human immunodeficiency viruses (HIV), can infect nondividing cells, and integration of proviral DNA occurs without the need for cell division. These properties make lentiviruses attractive for gene transfer into nondividing cells, such as hepatocytes, myofibers, hematopoietic stem cells, and neurons.

However, the use of lentivirus vectors, particularly HIV vectors, particularly for gene therapy, is hampered by concern over their safety. Thus, a need for the development of lentivirus vectors, particularly HIV vectors, with improved safety, particularly for gene therapy, exists.

SUMMARY OF THE INVENTION

The present invention relates to novel packaging cell lines useful for generating viral accessory protein independent lentivirus-derived, particularly HIV-derived, retroviral vector particles, to construction of such cell lines and to methods of using the accessory protein independent lentivirus-derived retroviral vector particles to introduce DNA of interest into cells (e.g, eukaryotic cells such as animal (particularly mammalian), plant or yeast cells or prokaryotic cells such as bacterial cells). In a preferred embodiment, the packaging cell lines of the present invention are stable packaging cell lines.

In one embodiment of the invention, packaging cell lines for producing a viral accessory protein independent lentivirus-derived retroviral vector particles comprise (a) a cell (e.g., mammalian cell); and (b) a retroviral nucleotide sequence in the cell which comprises a coding sequence for lentivirus gagpol, wherein said coding sequence has been codon optimized by mutagenisis to improve expression of the lentivirus gagpol proteins.

In second embodiment of the invention, packaging cell lines for producing a viral accessory protein independent lentivirus-derived retroviral vector particles comprise (a) a cell (e.g., mammalian cell); (b) a first retroviral nucleotide sequence in the cell which comprises a coding sequence for lentivirus gagpol, wherein said coding sequence has been codon optimized by mutagenisis to improve expression of the lentivirus gagpol proteins; and (c) a second retroviral nucleotide sequence in the cell which comprises the coding sequence for a heterologous envelope protein.

In a third embodiment of the invention, packaging cell lines for producing a viral accessory protein independent lentivirus-derived retroviral vector particles comprise (a) a cell (e.g., mammalian cell); (b) a first retroviral nucleotide sequence in the cell which comprises a coding sequence for lentivirus gagpol, wherein said coding sequence has been codon optimized by mutagenisis to improve expression of the lentivirus gagpol proteins; (c) a second retroviral nucleotide sequence in the cell which comprises the coding sequence for a heterologous envelope protein; and (d) a third retroviral nucleotide sequence which comprises a DNA sequence of interest and lentivirus cis-acting sequences required for packaging, reverse transcription and integration.

In a fourth embodiment of the invention, packaging cell lines for producing a viral accessory protein independent lentivirus-derived retroviral vector particles comprise (a) a cell (e.g., mammalian cell); (b) a retroviral nucleotide sequence in the cell which comprises a coding sequence for lentivirus gagpol, wherein said coding sequence has been codon optimized by mutagenisis to improve expression of the lentivirus gagpol proteins; and (c) a retroviral nucleotide sequence which comprises a DNA sequence of interest and lentivirus cis-acting sequences required for packaging, reverse transcription and integration.

In a fifth embodiment of the invention, packaging cell lines for producing a viral accessory protein independent HIV-derived retroviral vector particles comprise (a) a cell (e.g., mammalian cell); and (b) a retroviral nucleotide sequence in the cell which comprises a coding sequence for HIV gagpol, wherein said coding sequence has been codon optimized by mutagenisis to improve expression of the HIV gagpol proteins.

In sixth embodiment of the invention, packaging cell lines for producing a viral accessory protein independent HIV-derived retroviral vector particles comprise (a) a cell (e.g., mammalian cell); (b) a first retroviral nucleotide sequence in the cell which comprises a coding sequence for HIV gagpol, wherein said coding sequence has been codon optimized by mutagenisis to improve expression of the HIV gagpol proteins; and (c) a second retroviral nucleotide sequence in the cell which comprises the coding sequence for a heterologous envelope protein.

In a seventh embodiment of the invention, packaging cell lines for producing a viral accessory protein independent HIV-derived retroviral vector particles comprise (a) a cell (e.g., mammalian cell); (b) a first retroviral nucleotide sequence in the cell which comprises a coding sequence for HIV gagpol, wherein said coding sequence has been codon optimized by mutagenisis to improve expression of the HIV gagpol proteins; (c) a second retroviral nucleotide sequence in the cell which comprises the coding sequence for a heterologous envelope protein; and (d) a third retroviral nucleotide sequence which comprises a DNA sequence of interest and HIV cis-acting sequences required for packaging, reverse transcription and integration.

In a eighth embodiment of the invention, packaging cell lines for producing a viral accessory protein independent HIV-derived retroviral vector particles comprise (a) a cell (e.g., mammalian cell); (b) a retroviral nuclcotide sequence in the cell which comprises a coding sequence for HIV gagpol, wherein said coding sequence has been codon optimized by mutagenisis to improve expression of the HIV gagpol proteins; and (c) a retroviral nucleotide sequence which comprises a DNA sequence of interest and HIV cis-acting sequences required for packaging, reverse transcription and integration.

Alternatively, each of the packaging cell lines described herein can be produced using (1) a retroviral nucleotide sequence which comprises a codon optimized gag coding sequence and (2) a retroviral nucleotide sequence which comprises a codon optimized pol coding sequence, in place of the retroviral nucleotide sequence which comprises a codon optimized gagpol coding sequence.

In a particular embodiment, the heterologous envelope protein is the G glycoprotein of vesicular stomatitis virus (VSV G). In another embodiment, the heterologous envelope protein is the amphotropic envelope of the Moloney leukemia virus (MLV).

Cell lines for producing a viral accessory protein independent lentivirus-derived retroviral vector particles are produced by transfecting host cells (e.g., mammalian host cells) with a plasmid comprising a DNA sequence which encodes lentivirus gagpol proteins, wherein said DNA sequence has been codon optimized by mutagenisis to improve expression of the lentivirus gagpol proteins. Depending upon the particular cell line being produced, the host cells are also co-transfected with a plasmid comprising a DNA sequence which encodes a heterologous envelope protein, or a plasmid comprising a DNA sequence of interest and lentivirus cis-acting sequences required for packaging, reverse transcription and integration, or both of these plasmids. Alternatively, host cells are transfected with a plasmid comprising a codon optimized DNA sequence encoding a lentivirus gag protein and a plasmid comprising a codon optimized DNA sequence encoding a lentivirus pol protein, in place of the plasmid comprising a codon optimized DNA sequence encoding both lentivirus gagpol proteins.

Cell lines for producing a viral accessory protein independent HIV-derived retroviral vector particles are produced by co-transfecting host cells (e.g., mammalian host cells) with a plasmid comprising a DNA sequence which encodes HIV gagpol proteins, wherein said DNA sequence has been codon optimized by mutagenisis to improve expression of the HIV gagpol proteins. Depending upon the particular cell line being produced, the host cells are also co-transfected with a plasmid comprising a DNA sequence which encodes a heterologous envelope protein, or a plasmid comprising a DNA sequence of interest and HIV cis-acting sequences required for packaging, reverse transcription and integration, or both of these plasmids. Alternatively, host cells are transfected with a plasmid comprising a codon optimized DNA sequence encoding a HIV gag protein and a plasmid comprising a codon optimized DNA sequence encoding a HIV pol protein, in place of the plasmid comprising a codon optimized DNA sequence encoding both HIV gagpol proteins.

The present invention also relates to methods of producing viral accessory protein independent lentivirus-derived retroviral vector particles, comprising co-transfecting host cells (e.g., mammalian host cells) with (a) a first plasmid comprising a DNA sequence which encodes lentivirus gagpol proteins, wherein said DNA sequence has been codon optimized by mutagenisis to improve expression of the lentivirus gagpol proteins; (b) a second plasmid comprising a DNA sequence which encodes a heterologous envelope protein; and (c) a third plasmid comprising a DNA sequence of interest and lentivirus cis-acting sequences required for packaging, reverse transcription and integration. Alternatively, host cells are transfected with a plasmid comprising a codon optimized DNA sequence encoding a lentivirus gag protein and a plasmid comprising a codon optimized DNA sequence encoding a lentivirus pol protein, in place of the first plasmid comprising a codon optimized DNA sequence encoding both lentivirus gagpol proteins.

In a particular embodiment, the invention relates to methods of producing viral accessory protein independent HIV-derived retroviral vector particles, comprising co-transfecting host cells (e.g., mammalian host cells) with (a) a first plasmid comprising a DNA sequence which encodes HIV gagpol proteins, wherein said DNA sequence has been codon optimized by mutagenisis to improve expression of the HIV gagpol proteins; (b) a second plasmid comprising a DNA sequence which encodes a heterologous envelope protein; and (c) a third plasmid comprising a DNA sequence of interest and HIV cis-acting sequences required for packaging, reverse transcription and integration. Alternatively, host cells are transfected with a plasmid comprising a codon optimized DNA sequence encoding a HIV gag protein and a plasmid comprising a codon optimized DNA sequence encoding a HIV pol protein, in place of the first plasmid comprising a codon optimized DNA sequence encoding both HIV gagpol proteins.

The present invention also relates to viral accessory protein-independent retroviral particles produced by or obtainable by (obtained by) the methods described herein.

The present invention further relates to isolated DNA encoding a codon optimized lentivirus gagpol, isolated DNA encoding the gag coding region of a codon optimized lentivirus gagpol, and isolated DNA encoding the pol coding region of a codon optimized lentivirus gagpol. In a particular embodiment, the present invention relates to isolated DNA encoding a codon optimized HIV gagpol, isolated DNA encoding the gag coding region of a codon optimized HIV gagpol, and isolated DNA encoding the pol coding region of a codon optimized HIV gagpol.

The packaging cell lines and viral particles of the present invention can be used for gene therapy or gene replacement with improved safety. The packaging cell lines and viral particles of the present invention can also be used in development and production of vaccines, and in production of biochemical reagents. Gene therapy vectors produced with the cell lines of the present invention are expected to be valuable medical therapeutics.

BRIEF DESCRIPTION OF THE DRAWINGS

FIG. 2 is a table which depicts codon usage frequencies in genes which are highly expressed and in the codon optimized gagpol open reading frame of the HIV packaging construct described herein.

FIG. 4 is a list of some characteristics relating to the HIV Rev protein.

FIG. 5 is a list of some points relating to codon optimization of HIV gagpol.

FIG. 6 is a partial DNA sequence of HIV gag (SEQ ID NO: 1), showing inactivation of inhibitory sequences as described in Schwartz, S. et al., J. Virol., 66(12):7176–7182 (1992).

FIGS. 8A–8E depict the alignment of the nucleotide sequences and predicted amino acid sequences for the gag coding region of a wildtype HIV gagpol and a codon optimized HIV gagpol. "NL4-3 genbank.SEQ" indicates the nucleotide sequence (SEQ ID NO:2) and predicted amino acid sequence (SEQ ID NO:3) for the gag coding region of a wildtype HIV gagpol. "pHDMHgpm2.seq" indicates the nucleotide sequence (SEQ ID NO:4) and predicted amino acid sequence (SEQ ID NO:5) for the gag coding region of a codon optimized HIV gagpol. The "NL4-3 genbank.SEQ" sequences are publicly available at the NIH GenBank sequence repository (Accesssion No. M19921).

FIGS. 9A–9L depict the alignment of the nucleotide sequences and predicted amino acid sequences for the pol coding region of a wildtype HIV gagpol and a codon optimized HIV gagpol. "NL4-3 genbank.SEQ" indicates a nucleotide sequence (SEQ ID NO:6) and a predicted amino acid sequence (SEQ ID NO:7) for the pol coding region of a wildtype HIV gagpol available in the NIH GenBank sequence repository (Accesssion No. M19921). The nucleotide and amino acid sequences for the pol coding region available in the GenBank sequence repository contain two sequence errors, which are indicated in FIGS. 9A–9L with shading. "pNL4-3.seq" indicates the correct nucleotide sequence (SEQ ID NO:8) and predicted amino acid sequence (SEQ ID NO:9) for the pol coding region of a wildtype HIV gagpol. "pHDMHgpm2.seq" indicates the nucleotide sequence (SEQ ID NO: 10) and predicted amino acid sequence (SEQ ID NO: 11) for the pol coding region of a codon optimized HIV gagpol.

FIGS. 10A–10D depict the DNA sequence (SEQ ID NO:12) for pHDMHgpm2. The CMV enhancer/promoter is at nucleotides 97 to 679, human betaglobin sequences (Bglobin) are at nucleotides 761 to 864, 865 to 1303 and 5710 to 6469 (end of Bglobin is at nucleotdes 6445 to 6469), mRNA sequences are at nucleotides 680 to 778 and 1255 to 592 1, SV40 origin of replication is at hucleotides 8796 to 8908, beta-lactamase (bla) coding region is at nucleotides 6709 to 7569, intron sequences are at nucleotides 779 to 1254, the codon optimized gag coding region is at nucleotides 1318 to 2820, the codon optimized pol coding region is at nucleotides 2619 to 5624 and the poly A site is at nucleotides 5897 to 5921.

DETAILED DESCRIPTION OF THE INVENTION

Figure 1:
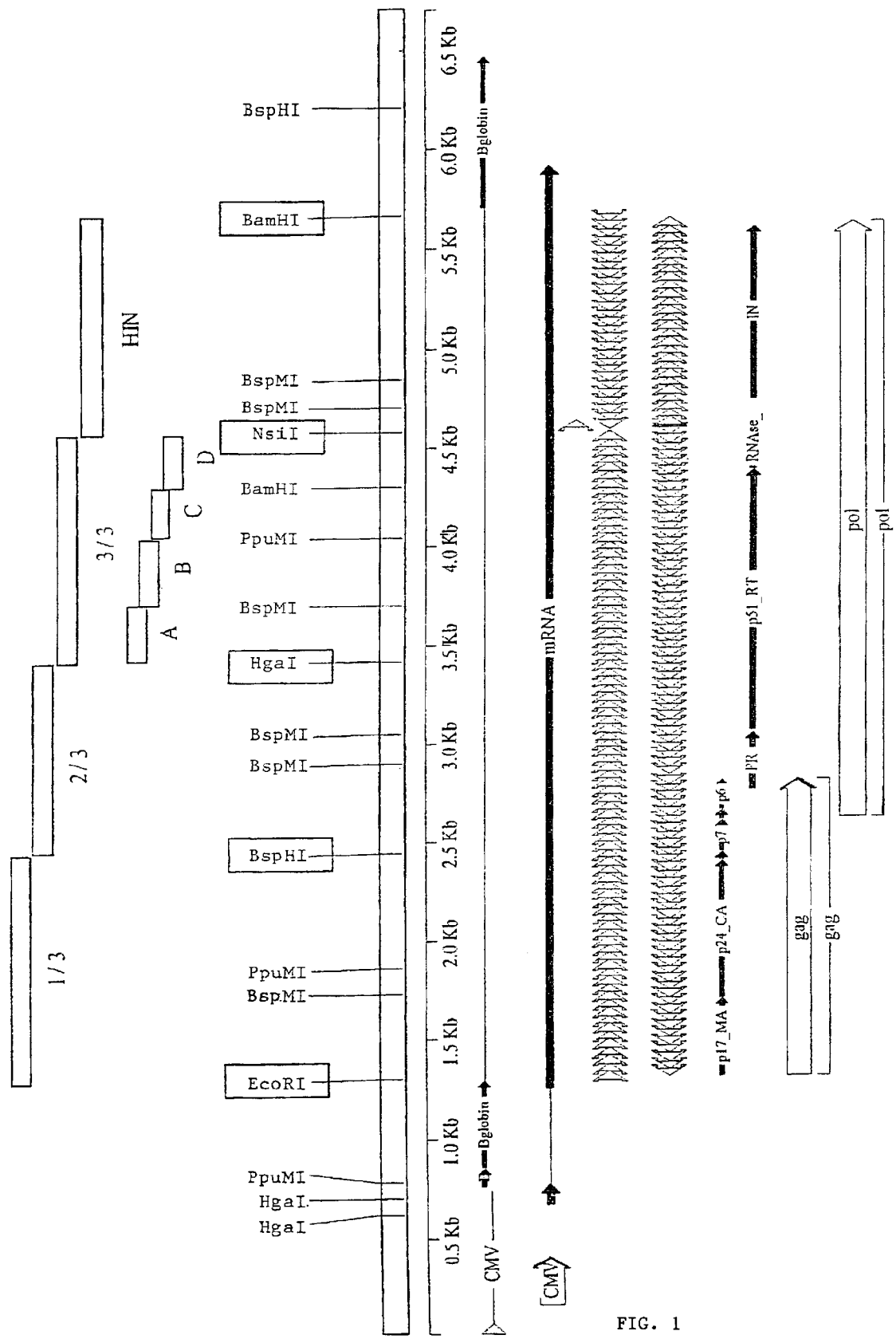
FIG. 1 is a schematic diagram of an expression cassette containing the codon optimized gagpol genes. The DNA was constructed in multiple segments, which arc indicated at the top as ⅓, ⅔, 3/3 (A, B, C and D) and HIN. Restriction sites used to assemble the cloned segments are indicated above the kilobasepair (Kb) ruler. Below the ruler are multiple features showing the location of the human cytomegalovirus (CMV) promoter, human betaglobin sequences (Bglobin), mRNA sequences (thinner line represents intronic sequence), the gag and pol open reading frames, the individual proteolytic fragment coding sequences (p17_MA, p24_CA, p7, p6, PR, p51_RT, RNaseH and integrase (IN)) and each synthetic oligonucleotide used in the assembly process (multiple adjacent open arrows).

The present invention relates to novel packaging cell lines useful for generating viral accessory protein independent lentivirus-derived, particularly HIV-derived, retroviral vector particles, to construction of such cell lines and to methods of using the accessory protein independent lentivirus-derived retroviral vector particles to introduce DNA of interest into cells (e.g, eukaryotic cells such as animal (particularly mammalian), plant or yeast cells or prokaryotic cells such as bacterial cells). In a particular embodiment, the packaging cell lines of the present invention are stable packaging cell lines.

The cell lines are engineered to express the lentivirus proteins necessary for virus particle formation (gagpol proteins), without containing DNA sequences from lentivirus accessory proteins (tat, vif, vpr, vpu, nef and rev proteins and Rev response element (RRE)). Additionally, no viral sequences (such as cis-acting elements termed constitutive transport elements (CTEs)) will be expressed as RNA of any kind. DNA sequences for lentivirus gagpol are codon optimized by extensively mutagenizing the sequences to improve expression and to reduce the risk of recombination between transfer vector sequences and gagpol messenger RNA. This greatly improves the safety of virus preparations generated from these cell lines. In a particular embodiment, the DNA sequences for lentivirus gagpol are not codon optimized in the overlap region between the gag and pol sequences and in cis-acting signals necessary for translation of pol.

Examples of lentiviruses include human immunodeficiency viruses (e.g., HIV-1, HIV-2, HIV-3), bovine lentiviruses (e.g., bovine immunodeficiency viruses, bovine immunodeficiency-like viruses, Jembrana disease viruses), equine lentiviruses (e.g., equine infectious anemia viruses), feline lentiviruses (e.g., feline immunodeficiency viruses, panther lentiviruses, puma lentiviruses), ovine/caprine lentiviruses (e.g., Brazilian caprine lentiviruses, caprine arthritis-encephalitis viruses, Maedi-Visna viruses, Maedi-Visna-like viruses, Maedi-Visna-related viruses, ovine lentiviruses, Visna lentiviruses), Simian AIDS retroviruses (e.g., human T-cell lymphotropic virus type 4), simian immunodeficiency viruses, simian-human immunodeficiency viruses, human lymphotrophic viruses (e.g., type III), simian T-cell lymphotrophic viruses.

In another embodiment, cell lines are engineered to express the HIV proteins necessary for virus particle formation (gagpol proteins), without containing DNA sequences from HIV accessory proteins (tat, vif, vpr, vpu, nef and rev proteins and Rev response element (RRE)). Additionally, no viral sequences (such as cis-acting elements termed constitutive transport elements (CTEs)) will be expressed as RNA of any kind. DNA sequences for a HIV gagpol are codon optimized by mutagenesis to improve expression and to reduce the risk of recombination between transfer vector sequences and gagpol messenger RNA. In a particular embodiment, the DNA sequences for HIV gagpol are not codon optimized in the overlap region between the gag and pol sequences and in cis-acting signals necessary for translation of pol.

Alternatively, each of the packaging cell lines described herein can be produced using (1) a nucleotide sequence which comprises a codon optimized gag coding sequence and (2) a nucleotide sequence which comprises a codon optimized pol coding sequence, in place of the nucleotide sequence which comprises a codon optimized gagpol coding sequence. In this embodiment, the gag and pol coding sequences can be completely codon optimized Benefits of the present invention include the removal of potentially harmful lentivirus accessory proteins and other viral sequences, and the reduction of the risk of recombination to produce replication competent virus.

Packaging cell lines for producing a viral accessory protein independent lentivirus-derived retroviral vector particles comprise a mammalian cell and a retroviral nucleotide sequence comprising a coding sequence for a lentivirus gagpol which has been codon optimized. In a particular embodiment the packaging cell lines further comprise a retroviral nucleotide sequence comprising a coding sequence for a heterologous envelope protein. In a second embodiment, the packaging cell lines further comprise a retroviral nucleotide sequence comprising a coding sequence for a heterologous envelope protein and a retroviral nucleotide sequence which comprises a DNA sequence of interest and HIV cis-acting sequences required for packaging, reverse transcription and integration. In third embodiment, the packaging cell lines further comprise a retroviral nucleotide sequence which comprises a DNA sequence of interest and HIV cis-acting sequences required for packaging, reverse transcription and integration. Alternatively, the packaging cell lines of the present invention comprise a retroviral nucleotide sequence which comprises a codon optimized gag coding sequence and (2) a retroviral nucleotide sequence which comprises a codon optimized pol coding sequence, in place of the retroviral nucleotide sequence which comprises a codon optimized gagpol coding sequence.

The coding sequence(s) for lentivirus gagpol which has (have) been codon optimized results in improved expression of the lentivirus gagpol proteins and reduces the risk of recombination between the transfer vector and gagpol messenger RNA. Codon optimization of the coding sequence(s) for lentivirus gagpol was obtained by mutagenizing for each particular amino acid residue, specific nucleic acid bases in a codon for the particular amino acid residue to a nucleic acid base which is present in a codon which occurs at a high frequency in genes which are highly expressed for the same amino acid residue. In a particular embodiment, the resulting optimized codon also does not cause introduction of mRNA splicing signals into the codon optimized sequence. Thus, in a particular embodiment, codon optimization of the coding sequence(s) for lentivirus gagpol is obtained by mutagenizing for each particular amino acid residue, specific nucleic acid bases in a codon for the particular amino acid residue to a nucleic acid base that is present in a codon which (1) occurs at a high frequency in genes which are highly expressed for the same amino acid residue and (2) does not cause introduction of mRNA splicing signals into the codon optimized sequence. Codon optimization typically results in the removal of nucleic acid base A-rich instability elements.

In a particular embodiment, the coding sequence for a HIV gagpol (pNL4-3; available through the AIDS repository, NIH; Adachi et al., *J Virol.*, 59:284–291 (1986)) has been codon optimized to improve translational efficiency of the HIV gagpol proteins and reduce the risk of recombination between the transfer vector and HIV gagpol messenger RNA. Two hundred thirty-seven base pairs (237 bp) consisting of the gag pol overlap and cis-acting signals necessary for translation of pol (nucleotides 2583 to 2819 of SEQ ID NO: 12) were not optimized. The HIV gagpol sequence obtained using the codon optimization process does not differ at the amino acid level from the wildtype HIV gagpol sequence, but differs at the nucleotide level from the HIV gagpol sequence. A codon optimized HIV gag sequence is shown in FIGS. 8A–8E (pHDMHgpm2.seq) (SEQ ID NO:4). A codon optimized HIV pol sequence is shown in FIGS. 9A–9L (pHDMHgpm2.seq) (SEQ ID NO: 10).

A plasmid comprising DNA sequences which encode codon optimized lentivirus gagpol proteins is also referred to herein as a packaging construct. This plasmid includes a promoter which drives the expression of the gagpol proteins, such as the human cytomegalovirus (hCMV) immediate early promoter. This plasmid is defective for the production of the viral envelope and accessory proteins tat, vif, vpr, vpu, nef and rev and the Rev response element (RRE). The packaging construct also does not contain viral sequences which are transcribed into mRNA, such as constitutive transport elements (CTEs).

Figure 11:
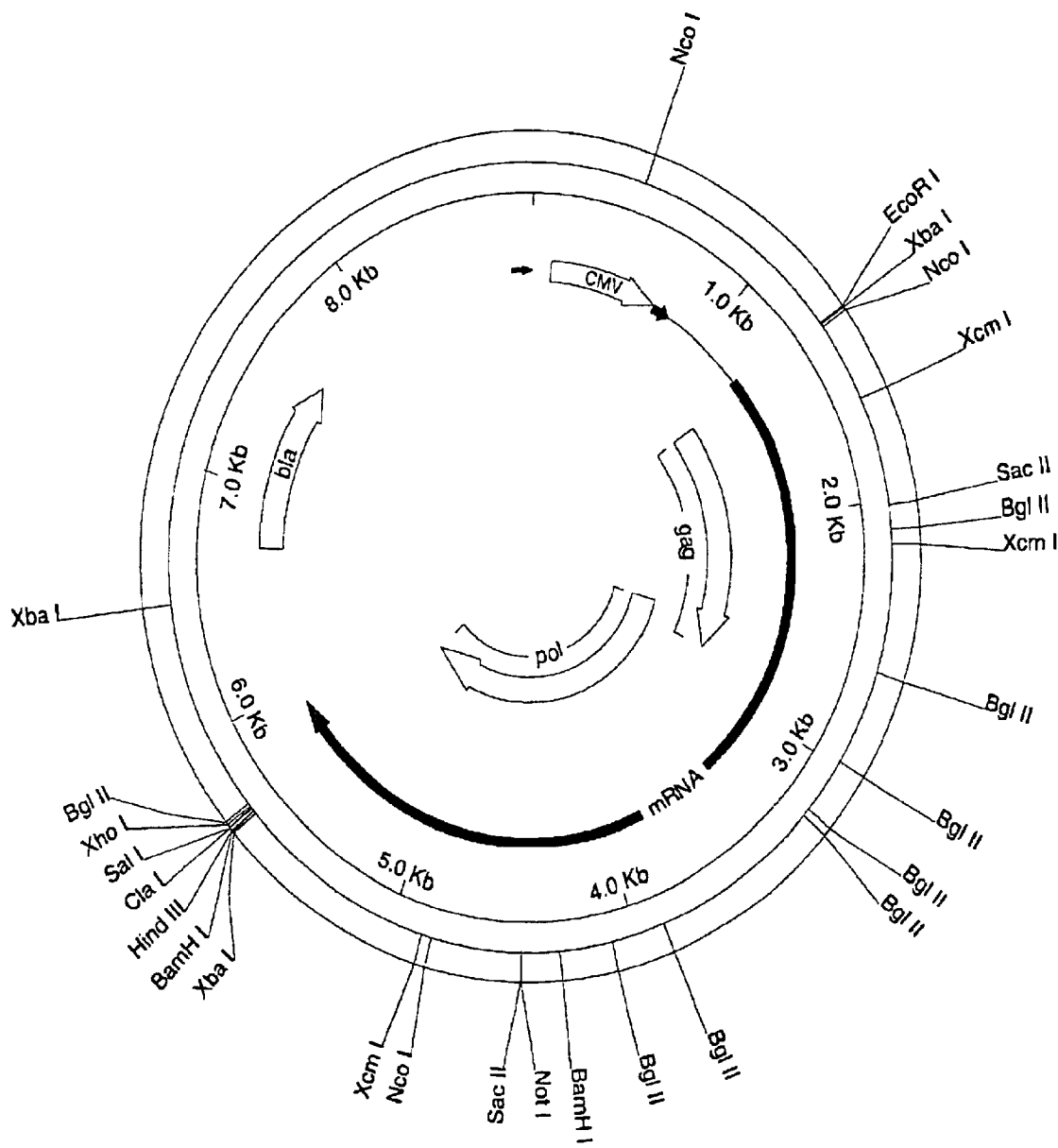
FIG. 11 is a circular map of plasmid pHDMHgpm2.

A packaging construct comprising a codon optimized HIV gagpol is depicted in FIG. 1 and in FIG. 11. FIGS. 10A–10D depict the DNA sequence (SEQ ID NO:12) for the packaging construct pHDMHgpm2. This packaging construct (pHDMHgpm2) was constructed as follows: Plasmid pMDA.HIVgp mam was generated by chemical synthesis and PCR assembly (which is described in, for example, Stemmer et al., *Gene*, 164:49–53 (1995)) of 215 different oligonucleotides. The DNA sequence for pMDA.HIVgp mam is the same as the DNA sequence for pMDA.HIVgp jtg except for 4.3 kb which was codon optimized using the DNAStar program (LaserGene, Madison, Wis.). Two hundred thirty-seven base pairs (237 bp) consisting of the gag pol overlap and cis-acting signals necessary for translation of pol (nucleotides 2583 to 2819 of SEQ ID NO: 12) were not optimized due to dual reading frame constraints. A NsiI site 5' of IN was preserved to aid fusion with wildtype sequences. Several single or double base pair silent mutations were introduced either to prevent potential splice donors and acceptors, or by the synthesis process. pMDA-.HIVgp jtg was derived from HIV-1 strain NL4-3. The protease mutation that is present in the NL4-3 NIH GenBank sequence was then repaired (FIG. 9B), changing the nucleotide present at position 2948 of SEQ ID NO:12 from a "G" to a "C", thereby producing the codon present at nucleotide positions 2948 to 2950 of SEQ ID NO: 12 which encodes an arginine instead of the glycine present in the NL4-3 GenBank amino acid sequence. The resulting plasmid was named pMDHgpmam. The EcoRI-HindIII fragment of pMDHgpmam was inserted into pHDM2b, a high copy version of the pMD vector (Ory, D. et al., *Proc. Natl. Acad. Sci. USA*, 93(21):11400–11406 (1996)), to produce plasmid pHDMHgpm. The sequencing mutation that is present in the RNase domain of the NL4-3 NIH GenBank sequence was repaired (FIG. 9H), changing the codon present at nucleotide positions 4724 to 4726 of SEQ ID NO:12 from "GGG" to "AAG", thereby producing a codon encoding a lysine instead of the glycine present in the NL4-3 GenBank amino acid sequence. The resulting plasmid was named pHDMHgpm2. Codon usage frequencies in the codon optimized gagpol open reading frame of the packaging construct pHDMHgpm2 are shown in FIG. 2.

As used herein, a heterologous envelope protein permits pseudotyping of particles generated by the packaging construct and includes the G glycoprotein of vesicular stomatitis virus (VSV G) and the amphotropic envelope of the Moloney leukemia virus (MLV). A plasmid comprising a DNA sequence which encodes a heterologous envelope protein is also referred to herein as an envelope coding plasmid.

The terms "mammal" and "mammalian", as used herein, refer to any vertebrate animal, including monotremes, marsupials and placental, that suckle their young and either give birth to living young (eutharian or placental mammals) or are egg-laying (metatharian or nonplacental mammals). Examples of mammalian species include humans and other primates (e.g., monkeys, chimpanzees), rodents (e.g., rats, mice, guinea pigs) and ruminants (e.g., cows, pigs, horses).

Examples of mammalian cells include human (such as HeLa cells, 293T cells, NIH 3T3 cells), bovine, ovine, porcine, murine (such as embryonic stem cells), rabbit and monkey (such as COS1 cells) cells. The cell may be a non-dividing cell (including hepatocytes, myofibers, hematopoietic stem cells, neurons) or a dividing cell. The cell may be an embryonic cell, bone marrow stem cell or other progenitor cell. Where the cell is a somatic cell, the cell can be, for example, an epithelial cell, fibroblast, smooth muscle cell, blood cell (including a hematopoietic cell, red blood cell, T-cell, B-cell, etc.), tumor cell, cardiac muscle cell, macrophage, dendritic cell, neuronal cell (e.g., a glial cell or astrocyte), or pathogen-infected cell (e.g., those infected by bacteria, viruses, virusoids, parasites, or prions).

Typically, cells isolated from a specific tissue (such as epithelium, fibroblast or hematopoietic cells) are categorized as a "cell-type." The cells can be obtained commercially or from a depository or obtained directly from an animal, such as by biopsy. Alternatively, the cell need not be isolated at all from the animal where, for example, it is desirable to deliver the virus to the animal in gene therapy.

To produce the cell lines of the present invention for producing a viral accessory protein independent lentivirus-derived retroviral vector particles, mammalian host cells are co-transfected with (a) a first plasmid comprising DNA sequence which encode lentivirus gagpol proteins, wherein said DNA sequence has been codon optimized by mutagenisis, as described above, to improve expression of the lentivirus gagpol proteins; and (2) a second plasmid comprising a DNA sequence which encodes a heterologous envelope protein, or a retroviral nucleotide sequence which comprises a DNA sequence of interest and lentivirus cis-acting sequences required for packaging, reverse transcription and integration, or both, under conditions appropriate for transfection of the cells.

In a particular embodiment, to produce the cell lines of the present invention for producing viral accessory protein independent HIV-derived retroviral vector particles mammalian host cells were cotransfected with (a) a first plasmid comprising DNA sequence which encode HIV gagpol proteins, wherein said DNA sequence has been codon optimized by mutagenisis, as described above, to improve expression of the HIV gagpol proteins; and (2) a second plasmid comprising a DNA sequence which encodes a heterologous envelope protein, or a retroviral nucleotide sequence which comprises a DNA sequence of interest and HIV cis-acting sequences required for packaging, reverse transcription and integration, or both, under conditions appropriate for transfection of the cells.

Virus stocks consisting of viral accessory protein independent lentivirus-derived, particularly HIV-derived, retroviral vector particles of the present invention are produced by maintaining the transfected cells under conditions suitable for virus production (e.g., in an appropriate growth media and for an appropriate period of time). Such conditions, which are not critical to the invention, are generally known in the art. See, e.g., *Sambrook et al., Molecular Cloning: A Laboratory Manual*, Second Edition, Cold Spring Harbor University Press, New York (1989); *Ausubel et al., Current Protocols in Molecular Biology*, John Wiley & Sons, New York (1998); U.S. Pat. No. 5,449,614; and U.S. Pat. No. 5,460,959, the teachings of which are incorporated herein by reference.

To generate viral accessory protein independent lentivirus-derived retroviral vector particles, mammalian host cells can be co-transfected with (a) a first plasmid comprising DNA sequence which encode lentivirus gagpol proteins, wherein said DNA sequence has been codon optimized by mutagenisis, as described above, to improve expression of the lentivirus gagpol proteins; (b) a second plasmid comprising a DNA sequence which encodes a heterologous envelope protein; and (c) a third plasmid comprising a DNA sequence of interest and lentivirus cis-acting sequences required for packaging, reverse transcription and integration. Alternatively, mammalian cells are transfected with a plasmid comprising a codon optimized DNA sequence encoding a lentivirus gag protein and a plasmid comprising a codon optimized DNA sequence encoding a lentivirus pol protein, in place of the first plasmid comprising a codon optimized DNA sequence encoding both lentivirus gagpol proteins. Alternatively, mammalian host cells are transfected with a plasmid comprising a codon optimized DNA sequence encoding a lentivirus gag protein and a plasmid comprising a codon optimized DNA sequence encoding a lentivirus pol protein, in place of the first plasmid comprising a codon optimized DNA sequence encoding both lentivirus gagpol proteins.

In a particular embodiment, the invention relates to methods of producing viral accessory protein independent HIV-derived retroviral vector particles, comprising co-transfecting mammalian host cells with (a) a first plasmid comprising DNA sequence which encode HIV gagpol proteins, wherein said DNA sequence has been codon optimized by mutagenisis, as described above, to improve expression of the HIV gagpol proteins; (b) a second plasmid containing a DNA sequence which encodes a heterologous envelope protein; and (c) a third plasmid comprising a DNA sequence of interest and HIV cis-acting sequences required for packaging, reverse transcription and integration. Alternatively, mammalian host cells are transfected with a plasmid comprising a codon optimized DNA sequence encoding a HIV gag protein and a plasmid comprising a codon optimized DNA sequence encoding a HIV pol protein, in place of the first plasmid comprising a codon optimized DNA sequence encoding both HIV gagpol proteins.

Virus particles produced by the methods described herein, using a codon optimized HIV packaging construct produced as described herein, were compared by Western analysis with virus particles produced as described in Naldini et al., *Science*, 272:263–267 (1996), using the packaging construct plasmid pCMVΔR8.2. Both the immunological reactivity and the proteolytic processing were confirmed to be indistinguishable.

Figure 3:
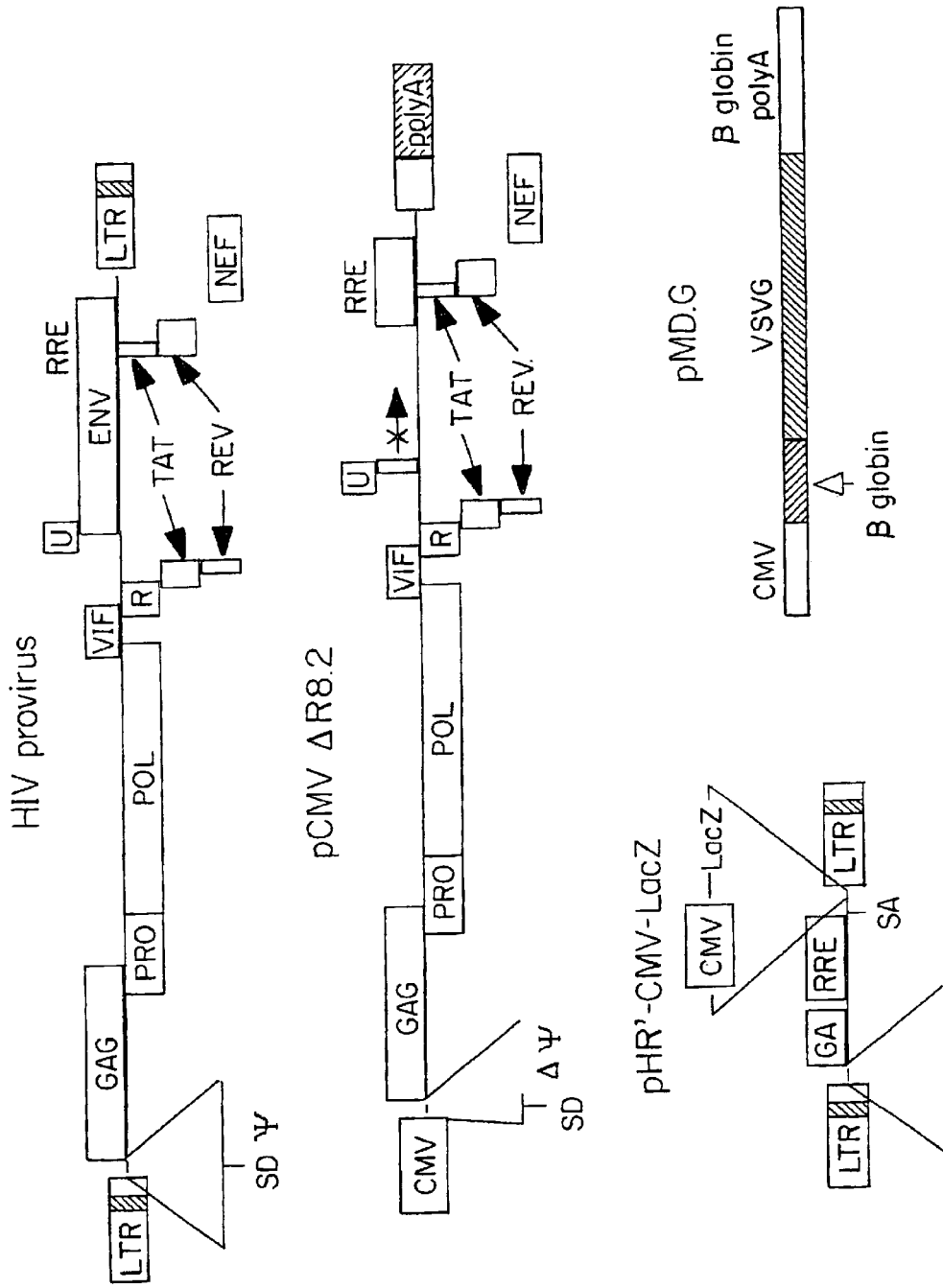
FIG. 3 is a schematic representation of the HIV provirus and a prior art three-plasmid expression system used for generating a pseudotyped HIV-based vector by transient transfection as described in Naldini et al., Science, 272:263–267 (1996).
Figure 7:
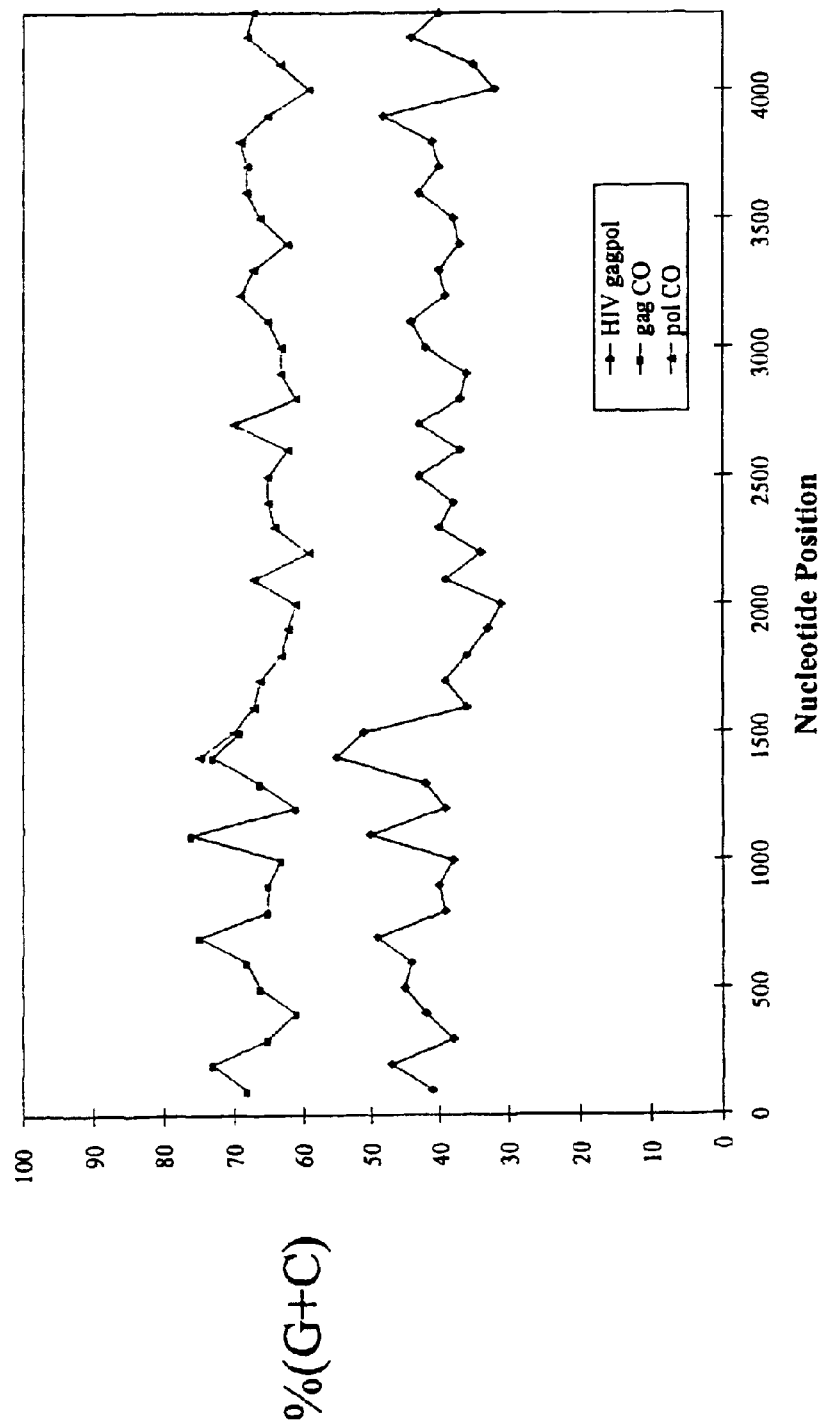
FIG. 7 a plot of the % (G+C) content of wildtype HIV gagpol sequences and theoretically codon optimized HIV gagpol sequences. The percent of bases, either G or C, was calculated for a 30 nucleotide moving window for the entire length of the gagpol gene, and the value plotted versus nucleotide position. Diamonds=HIV gagpol sequences; squares=full optimal back-translation for gag open reading frame; triangles=full optimal back-translation for pol open reading frame; CO=codon optimized.

A plasmid comprising a DNA sequence of interest and HIV cis-acting sequences required for packaging, reverse transcription and integration is also referred to herein as a transfer vector. A transfer vector, as used herein, refers to a vehicle which is used to introduce a DNA of interest into a eurkaryotic cell, particularly a mammalian cell. FIG. 3 depicts an example of a transfer vector.

DNA sequence of interest, as used herein, include all or a portion of a gene or genes encoding a nucleic acid product whose expression in a cell or a mammal is desired. In a particular embodiment, the nucleic acid product is a heterologous therapeutic protein. Examples of therapeutic proteins include antigens or immunogens, such as a polyvalent vaccine, cytokines, tumor necrosis factor, interferons, interleukins, adenosinc dearninase, insulin, T-cell receptors, soluble CD4, growth factors, such as epidermal growth factor, human growth factor, insulin-like growth factors, fibroblast growth factors), blood factors, such as Factor VIII, Factor IX, cytochrome b, glucocerebrosidase, ApoE, ApoC, ApoAI, the LDL receptor, negative selection markers or "suicide proteins", such as thymidine kinase (including the HSV, CMV, VZV TK), anti-angiogenic factors, Fc receptors, plasminogen activators, such as t-PA, u-PA and streptokinase, dopamine, MHC, tumor suppressor genes such as p53 and Rb, monoclonal antibodies or antigen binding fragments thereof, drug resistance genes, ion channels, such as a calcium channel or a potassium channel, adrenergic receptors, hormones (including growth hormones) and anti-cancer agents. In another embodiment, the nucleic acid product is a gene product to be expressed in a cell or a mammal and which product is otherwise defective or absent in the cell or mammal. For example, the nucleic acid product can be a functional gene(s) which is defective or absent in the cell or mammal.

DNA sequence of interest includes DNA sequences (control sequences) which are necessary to drive the expression of the gene or genes. The control sequences are operably linked to the gene. The term "operably linked", as used herein, is defined to mean that the gene is linked to control sequences in a manner which allows expression of the gene (or the nucleic acid sequence). Generally, operably linked means contiguous. Control sequences include a transcriptional promoter, an optional operator sequence to control transcription, a sequence encoding suitable MRNA ribosomal binding sites and sequences which control termination of transcription and translation. In a particular embodiment, a recombinant gene encoding a desired nucleic acid product can be placed under the regulatory control of a promoter which can be induced or repressed, thereby offering a greater degree of control with respect to the level of the product produced.

As used herein, the term "promoter" refers to a sequence of DNA, usually upstream (5') of the coding region of a structural gene, which controls the expression of the coding region by providing recognition and binding sites for RNA polymerase and other factors which may be required for initiation of transcription. Suitable promoters are well known in the art. Exemplary promoters include the SV40, CMV and human elongation factor (EFI) promoters. Other suitable promoters are readily available in the art (see, eg., Ausubel et al., *Current Protocols in Molecular Biology*, John Wiley & Sons, Inc., New York (1998); Sambrook et al., *Molecular Cloning: A Laboratory Manual*, 2nd edition, Cold Spring Harbor University Press, New York (1989); and U.S. Pat. No. 5,681,735).

A DNA sequence of interest can be isolated from nature, modified from native sequences or manufactured de novo, as described in, for example, Ausubel et al., *Current Protocols in Molecular Biology*, John Wiley & Sons, New York (1998); and Sambrook et al., *Molecular Cloning: A Laboratory Manual*, 2nd edition, Cold Spring Harbor University Press, New York. (1989). DNA sequences can be isolated and fused together by methods known in the art, such as exploiting and manufacturing compatible cloning or restriction sites.

The packaging cell lines and viral particles of the present invention can be used, in vitro, in vivo and ex vivo, to introduce DNA of interest into a eukaryotic cell (e.g., a mammalian cell) or a mammal (e.g., a human or other mammal or vertebrate). The cells can be obtained commercially or from a depository or obtained directly from a mammal, such as by biopsy. The cells can be obtained from a mammal to whom they will be returned or from another/different mammal of the same or different species. For example, using the packaging cell lines or viral particles of the present invention, DNA of interest can be introduced into nonhuman cells, such as pig cells, which are then introduced into a human. Alternatively, the cell need not be isolated from the mammal where, for example, it is desirable to deliver vial particles of the present invention to the mammal in gene therapy.

Ex vivo therapy has been described, for example, in Kasid et al., *Proc. Natl. Acad. Sci. USA*, 87:473 (1990); Rosenberg et al., *N. Engl. J. Med.*, 323:570 (1990); Williams et al., *Nature*, 310:476 (1984); Dick et al., Cell, 42:71 (1985); Keller et al., *Nature*, 318:149 (1985); and Anderson et al., U.S. Pat. No. 5,399,346.

Methods for administering (introducing) viral particles directly to a mammal are generally known to those practiced in the art. For example, modes of administration include parenteral, injection, mucosal, systemic, implant, intraperitoneal, oral, intradernal, transdermal (e.g., in slow release polymers), intramuscular, intravenous including infusion and/or bolus injection, subcutaneous, topical, epidural, etc. Viral particles of the present invention can, preferably, be administered in a pharmaceutically acceptable carrier, such as saline, sterile water, Ringer's solution, and isotonic sodium chloride solution.

The dosage of a viral particle of the present invention administered to a mammal, including frequency of administration, will vary depending upon a variety of factors, including mode and route of administration; size, age, sex, health, body weight and diet of the recipient mammal; nature and extent of symptoms of the disease or disorder being treated; kind of concurrent treatment, frequency of treatment, and the effect desired.

The teachings of all the articles, patents, patent applications and GenBank sequences cited herein are incorporated by reference in their entirety.

While this invention has been particularly shown and described with references to preferred embodiments thereof, it will be understood by those skilled in the art that various changes in form and details may be made therein without departing from the spirit and scope of the invention as defined by the appended claims.

SEQUENCE LISTING

<160> NUMBER OF SEQ ID NOS: 12

<210> SEQ ID NO 1
<211> LENGTH: 396
<212> TYPE: DNA
<213> ORGANISM: Homo sapien

<400> SEQUENCE: 1

```
atgggtgcga gagcgtcagt attaagcggg ggagaattag atcgatggga aaaaattcgg      60
ttaaggccag ggggaaagaa aaaatataaa ttaaaacata tagtatgggc aagcagggag     120
ctagaacgat tcgcagttaa tcctggcctg ttagaaacat cagaaggctg tagacaaata     180
```

-continued

```
ctgggacagc tacaaccatc ccttcagaca ggatcagaag aacttagatc attatataat    240
acagtagcaa ccctctattg tgtgcatcaa aggatagaga taaaagacac caaggaagct    300
ttagacaaga tagaggaaga gcaaaacaaa agtaagaaaa aagcacagca agcagcagct    360
gacacaggac acagcaatca ggtcagccaa aattac                              396
```

<210> SEQ ID NO 2
<211> LENGTH: 1503
<212> TYPE: DNA
<213> ORGANISM: Homo sapien
<220> FEATURE:
<221> NAME/KEY: CDS
<222> LOCATION: (1)...(1503)

<400> SEQUENCE: 2

```
atg ggt gcg aga gcg tcg gta tta agc ggg gga gaa tta gat aaa tgg     48
Met Gly Ala Arg Ala Ser Val Leu Ser Gly Gly Glu Leu Asp Lys Trp
 1               5                  10                  15 gaa aaa att cgg tta agg cca ggg gga aag aaa caa tat aaa cta aaa    96
Glu Lys Ile Arg Leu Arg Pro Gly Gly Lys Lys Gln Tyr Lys Leu Lys
             20                  25                  30 cat ata gta tgg gca agc agg gag cta gaa cga ttc gca gtt aat cct   144
His Ile Val Trp Ala Ser Arg Glu Leu Glu Arg Phe Ala Val Asn Pro
         35                  40                  45 ggc ctt tta gag aca tca gaa ggc tgt aga caa ata ctg gga cag cta   192
Gly Leu Leu Glu Thr Ser Glu Gly Cys Arg Gln Ile Leu Gly Gln Leu
     50                  55                  60 caa cca tcc ctt cag aca gga tca gaa gaa ctt aga tca tta tat aat   240
Gln Pro Ser Leu Gln Thr Gly Ser Glu Glu Leu Arg Ser Leu Tyr Asn
 65                  70                  75                  80 aca ata gca gtc ctc tat tgt gtg cat caa agg ata gat gta aaa gac   288
Thr Ile Ala Val Leu Tyr Cys Val His Gln Arg Ile Asp Val Lys Asp
                 85                  90                  95 acc aag gaa gcc tta gat aag ata gag gaa gag caa aac aaa agt aag   336
Thr Lys Glu Ala Leu Asp Lys Ile Glu Glu Glu Gln Asn Lys Ser Lys
            100                 105                 110 aaa aag gca cag caa gca gca gct gac aca gga aac aac agc cag gtc   384
Lys Lys Ala Gln Gln Ala Ala Ala Asp Thr Gly Asn Asn Ser Gln Val
        115                 120                 125 agc caa aat tac cct ata gtg cag aac ctc cag ggg caa atg gta cat   432
Ser Gln Asn Tyr Pro Ile Val Gln Asn Leu Gln Gly Gln Met Val His
    130                 135                 140 cag gcc ata tca cct aga act tta aat gca tgg gta aaa gta gta gaa   480
Gln Ala Ile Ser Pro Arg Thr Leu Asn Ala Trp Val Lys Val Val Glu
145                 150                 155                 160 gag aag gct ttc agc cca gaa gta ata ccc atg ttt tca gca tta tca   528
Glu Lys Ala Phe Ser Pro Glu Val Ile Pro Met Phe Ser Ala Leu Ser
                165                 170                 175 gaa gga gcc acc cca caa gat tta aat acc atg cta aac aca gtg ggg   576
Glu Gly Ala Thr Pro Gln Asp Leu Asn Thr Met Leu Asn Thr Val Gly
            180                 185                 190 gga cat caa gca gcc atg caa atg tta aaa gag acc atc aat gag gaa   624
Gly His Gln Ala Ala Met Gln Met Leu Lys Glu Thr Ile Asn Glu Glu
        195                 200                 205 gct gca gaa tgg gat aga ttg cat cca gtg cat gca ggg cct att gca   672
Ala Ala Glu Trp Asp Arg Leu His Pro Val His Ala Gly Pro Ile Ala
    210                 215                 220 cca ggc cag atg aga gaa cca agg gga agt gac ata gca gga act act   720
Pro Gly Gln Met Arg Glu Pro Arg Gly Ser Asp Ile Ala Gly Thr Thr
225                 230                 235                 240
```

-continued

```
agt acc ctt cag gaa caa ata gga tgg atg aca cat aat cca cct atc      768
Ser Thr Leu Gln Glu Gln Ile Gly Trp Met Thr His Asn Pro Pro Ile
                245                 250                 255 cca gta gga gaa atc tat aaa aga tgg ata atc ctg gga tta aat aaa      816
Pro Val Gly Glu Ile Tyr Lys Arg Trp Ile Ile Leu Gly Leu Asn Lys
            260                 265                 270 ata gta aga atg tat agc cct acc agc att ctg gac ata aga caa gga      864
Ile Val Arg Met Tyr Ser Pro Thr Ser Ile Leu Asp Ile Arg Gln Gly
        275                 280                 285 cca aag gaa ccc ttt aga gac tat gta gac cga ttc tat aaa act cta      912
Pro Lys Glu Pro Phe Arg Asp Tyr Val Asp Arg Phe Tyr Lys Thr Leu
    290                 295                 300 aga gcc gag caa gct tca caa gag gta aaa aat tgg atg aca gaa acc      960
Arg Ala Glu Gln Ala Ser Gln Glu Val Lys Asn Trp Met Thr Glu Thr
305                 310                 315                 320 ttg ttg gtc caa aat gcg aac cca gat tgt aag act att tta aaa gca     1008
Leu Leu Val Gln Asn Ala Asn Pro Asp Cys Lys Thr Ile Leu Lys Ala
                325                 330                 335 ttg gga cca gga gcg aca cta gaa gaa atg atg aca gca tgt cag gga     1056
Leu Gly Pro Gly Ala Thr Leu Glu Glu Met Met Thr Ala Cys Gln Gly
            340                 345                 350 gtg ggg gga ccc ggc cat aaa gca aga gtt ttg gct gaa gca atg agc     1104
Val Gly Gly Pro Gly His Lys Ala Arg Val Leu Ala Glu Ala Met Ser
        355                 360                 365 caa gta aca aat cca gct acc ata atg ata cag aaa ggc aat ttt agg     1152
Gln Val Thr Asn Pro Ala Thr Ile Met Ile Gln Lys Gly Asn Phe Arg
    370                 375                 380 aac caa aga aag act gtt aag tgt ttc aat tgt ggc aaa gaa ggg cac     1200
Asn Gln Arg Lys Thr Val Lys Cys Phe Asn Cys Gly Lys Glu Gly His
385                 390                 395                 400 ata gcc aaa aat tgc agg gcc cct agg aaa aag ggc tgt tgg aaa tgt     1248
Ile Ala Lys Asn Cys Arg Ala Pro Arg Lys Lys Gly Cys Trp Lys Cys
                405                 410                 415 gga aag gaa gga cac caa atg aaa gat tgt act gag aga cag gct aat     1296
Gly Lys Glu Gly His Gln Met Lys Asp Cys Thr Glu Arg Gln Ala Asn
            420                 425                 430 ttt tta ggg aag atc tgg cct tcc cac aag gga agg cca ggg aat ttt     1344
Phe Leu Gly Lys Ile Trp Pro Ser His Lys Gly Arg Pro Gly Asn Phe
        435                 440                 445 ctt cag agc aga cca gag cca aca gcc cca cca gaa gag agc ttc agg     1392
Leu Gln Ser Arg Pro Glu Pro Thr Ala Pro Pro Glu Glu Ser Phe Arg
    450                 455                 460 ttt ggg gaa gag aca aca act ccc tct cag aag cag gag ccg ata gac     1440
Phe Gly Glu Glu Thr Thr Thr Pro Ser Gln Lys Gln Glu Pro Ile Asp
465                 470                 475                 480 aag gaa ctg tat cct tta gct tcc ctc aga tca ctc ttt ggc agc gac     1488
Lys Glu Leu Tyr Pro Leu Ala Ser Leu Arg Ser Leu Phe Gly Ser Asp
                485                 490                 495 ccc tcg tca caa taa                                                 1503
Pro Ser Ser Gln
            500

<210> SEQ ID NO 3
<211> LENGTH: 500
<212> TYPE: PRT
<213> ORGANISM: Homo sapien

<400> SEQUENCE: 3

Met Gly Ala Arg Ala Ser Val Leu Ser Gly Gly Glu Leu Asp Lys Trp
 1               5                  10                  15
```

-continued

Glu Lys Ile Arg Leu Arg Pro Gly Gly Lys Lys Gln Tyr Lys Leu Lys
              20                  25                  30

His Ile Val Trp Ala Ser Arg Glu Leu Glu Arg Phe Ala Val Asn Pro
              35                  40                  45

Gly Leu Leu Glu Thr Ser Glu Gly Cys Arg Gln Ile Leu Gly Gln Leu
              50                  55                  60

Gln Pro Ser Leu Gln Thr Gly Ser Glu Glu Leu Arg Ser Leu Tyr Asn
65                  70                  75                  80

Thr Ile Ala Val Leu Tyr Cys Val His Gln Arg Ile Asp Val Lys Asp
              85                  90                  95

Thr Lys Glu Ala Leu Asp Lys Ile Glu Glu Glu Gln Asn Lys Ser Lys
              100                 105                 110

Lys Lys Ala Gln Gln Ala Ala Ala Asp Thr Gly Asn Asn Ser Gln Val
              115                 120                 125

Ser Gln Asn Tyr Pro Ile Val Gln Asn Leu Gln Gly Gln Met Val His
              130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
              165                 170                 175

Glu Gly Ala Thr Pro Gln Asp Leu Asn Thr Met Leu Asn Thr Val Gly
              180                 185                 190

Gly His Gln Ala Ala Met Gln Met Leu Lys Glu Thr Ile Asn Glu Glu
              195                 200                 205

Ala Ala Glu Trp Asp Arg Leu His Pro Val His Ala Gly Pro Ile Ala
              210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr His Asn Pro Pro Ile
              245                 250                 255

Pro Val Gly Glu Ile Tyr Lys Arg Trp Ile Ile Leu Gly Leu Asn Lys
              260                 265                 270

Ile Val Arg Met Tyr Ser Pro Thr Ser Ile Leu Asp Ile Arg Gln Gly
              275                 280                 285

Pro Lys Glu Pro Phe Arg Asp Tyr Val Asp Arg Phe Tyr Lys Thr Leu
              290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
              325                 330                 335

Leu Gly Pro Gly Ala Thr Leu Glu Glu Met Met Thr Ala Cys Gln Gly
              340                 345                 350

Val Gly Gly Pro Gly His Lys Ala Arg Val Leu Ala Glu Ala Met Ser
              355                 360                 365

Gln Val Thr Asn Pro Ala Thr Ile Met Ile Gln Lys Gly Asn Phe Arg
              370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
              405                 410                 415

Gly Lys Glu Gly His Gln Met Lys Asp Cys Thr Glu Arg Gln Ala Asn
              420                 425                 430

```
Phe Leu Gly Lys Ile Trp Pro Ser His Lys Gly Arg Pro Gly Asn Phe
            435                 440                 445

Leu Gln Ser Arg Pro Glu Pro Thr Ala Pro Pro Glu Glu Ser Phe Arg
        450                 455                 460

Phe Gly Glu Glu Thr Thr Thr Pro Ser Gln Lys Gln Glu Pro Ile Asp
465                 470                 475                 480

Lys Glu Leu Tyr Pro Leu Ala Ser Leu Arg Ser Leu Phe Gly Ser Asp
                485                 490                 495

Pro Ser Ser Gln
            500

<210> SEQ ID NO 4
<211> LENGTH: 1503
<212> TYPE: DNA
<213> ORGANISM: Artificial Sequence
<220> FEATURE:
<223> OTHER INFORMATION: Codon optimized form of HIV gag coding region
<220> FEATURE:
<221> NAME/KEY: CDS
<222> LOCATION: (1)...(1503)

<400> SEQUENCE: 4 atg ggc gcc cgc gcc tcc gtg ctg tcc ggc ggc gag ctg gac aag tgg      48
Met Gly Ala Arg Ala Ser Val Leu Ser Gly Gly Glu Leu Asp Lys Trp
 1               5                  10                  15 gag aag atc cgc ctg cgc ccc ggc ggc aag aag cag tac aag ctg aag      96
Glu Lys Ile Arg Leu Arg Pro Gly Gly Lys Lys Gln Tyr Lys Leu Lys
                20                  25                  30 cac atc gtg tgg gcc tcc cgc gag ctg gag cgc ttc gcc gtg aac ccc     144
His Ile Val Trp Ala Ser Arg Glu Leu Glu Arg Phe Ala Val Asn Pro
            35                  40                  45 ggc ctg ctg gag acc tcc gag ggc tgc cgc cag atc ctg ggc cag ctg     192
Gly Leu Leu Glu Thr Ser Glu Gly Cys Arg Gln Ile Leu Gly Gln Leu
        50                  55                  60 cag ccc tcc ctg caa acc ggc tcc gag gag ctg cgc tcc ctg tac aac     240
Gln Pro Ser Leu Gln Thr Gly Ser Glu Glu Leu Arg Ser Leu Tyr Asn
 65                  70                  75                  80 acc atc gcc gtg ctg tac tgc gtg cac cag cgc atc gac gtg aag gac     288
Thr Ile Ala Val Leu Tyr Cys Val His Gln Arg Ile Asp Val Lys Asp
                85                  90                  95 acc aag gag gcc ctg gac aag atc gag gag gag cag aac aag tcc aag     336
Thr Lys Glu Ala Leu Asp Lys Ile Glu Glu Glu Gln Asn Lys Ser Lys
                100                 105                 110 aag aag gcc cag cag gcc gcc gcc gac acc ggc aac aac tcc cag gtg     384
Lys Lys Ala Gln Gln Ala Ala Ala Asp Thr Gly Asn Asn Ser Gln Val
            115                 120                 125 tcc cag aac tac ccc atc gtg cag aac ctg cag ggc cag atg gtg cac     432
Ser Gln Asn Tyr Pro Ile Val Gln Asn Leu Gln Gly Gln Met Val His
        130                 135                 140 cag gcc atc tcc ccc cgc acc ctg aac gcc tgg gtg aag gtg gtg gag     480
Gln Ala Ile Ser Pro Arg Thr Leu Asn Ala Trp Val Lys Val Val Glu
145                 150                 155                 160 gag aag gcc ttc tcc ccc gaa gtc atc ccc atg ttc tcc gcc ctg tcc     528
Glu Lys Ala Phe Ser Pro Glu Val Ile Pro Met Phe Ser Ala Leu Ser
                165                 170                 175 gag ggc gcc acc ccc cag gac ctg aac acc atg ctg aac acc gtg ggc     576
Glu Gly Ala Thr Pro Gln Asp Leu Asn Thr Met Leu Asn Thr Val Gly
            180                 185                 190 ggc cac cag gcc gcc atg cag atg ctg aag gag acc atc aac gag gag     624
Gly His Gln Ala Ala Met Gln Met Leu Lys Glu Thr Ile Asn Glu Glu
        195                 200                 205
```

```
gcc gcc gag tgg gac cgc ctg cac ccc gtg cac gcc ggc ccc atc gcc      672
Ala Ala Glu Trp Asp Arg Leu His Pro Val His Ala Gly Pro Ile Ala
210                 215                 220 ccc ggc cag atg cgc gag ccc cgc ggc tcc gac atc gcc ggc acc acc      720
Pro Gly Gln Met Arg Glu Pro Arg Gly Ser Asp Ile Ala Gly Thr Thr
225                 230                 235                 240 tcc acc ctg caa gag cag atc ggc tgg atg acc cac aac ccc ccc atc      768
Ser Thr Leu Gln Glu Gln Ile Gly Trp Met Thr His Asn Pro Pro Ile
                245                 250                 255 ccc gtg ggc gag atc tac aag cgc tgg atc atc ctg ggc ctg aac aag      816
Pro Val Gly Glu Ile Tyr Lys Arg Trp Ile Ile Leu Gly Leu Asn Lys
            260                 265                 270 atc gtg cgc atg tac tcc ccc acc tcc atc ctg gac atc cgc cag ggc      864
Ile Val Arg Met Tyr Ser Pro Thr Ser Ile Leu Asp Ile Arg Gln Gly
        275                 280                 285 ccc aag gag ccc ttc cgc gac tac gtg gac cgc ttc tac aag acc ctg      912
Pro Lys Glu Pro Phe Arg Asp Tyr Val Asp Arg Phe Tyr Lys Thr Leu
    290                 295                 300 cgc gcc gag cag gcc tcc cag gag gta aag aac tgg atg acc gag acc      960
Arg Ala Glu Gln Ala Ser Gln Glu Val Lys Asn Trp Met Thr Glu Thr
305                 310                 315                 320 ctg ctg gtg cag aac gcc aac ccc gac tgc aag acc atc ctg aag gcc     1008
Leu Leu Val Gln Asn Ala Asn Pro Asp Cys Lys Thr Ile Leu Lys Ala
                325                 330                 335 ctg ggc ccc ggc gcc acc ctg gag gag atg atg acc gcc tgc cag ggc     1056
Leu Gly Pro Gly Ala Thr Leu Glu Glu Met Met Thr Ala Cys Gln Gly
            340                 345                 350 gtg ggc ggc ccc ggc cac aag gcc cgc gtg ctg gcc gag gcc atg tcc     1104
Val Gly Gly Pro Gly His Lys Ala Arg Val Leu Ala Glu Ala Met Ser
        355                 360                 365 caa gtc acc aac ccc gcc acc atc atg atc cag aag ggc aac ttc cgc     1152
Gln Val Thr Asn Pro Ala Thr Ile Met Ile Gln Lys Gly Asn Phe Arg
    370                 375                 380 aac cag cgc aag acc gtg aag tgc ttc aac tgc ggc aag gag ggc cac     1200
Asn Gln Arg Lys Thr Val Lys Cys Phe Asn Cys Gly Lys Glu Gly His
385                 390                 395                 400 atc gcc aag aac tgc cgc gcc ccc cgc aag aag ggc tgc tgg aag tgc     1248
Ile Ala Lys Asn Cys Arg Ala Pro Arg Lys Lys Gly Cys Trp Lys Cys
                405                 410                 415 ggc aag gag ggc cac cag atg aaa gat tgt act gag aga cag gct aat     1296
Gly Lys Glu Gly His Gln Met Lys Asp Cys Thr Glu Arg Gln Ala Asn
            420                 425                 430 ttt tta ggg aag atc tgg cct tcc cac aag gga agg cca ggg aat ttt     1344
Phe Leu Gly Lys Ile Trp Pro Ser His Lys Gly Arg Pro Gly Asn Phe
        435                 440                 445 ctt cag agc aga cca gag cca aca gcc cca cca gaa gag agc ttc agg     1392
Leu Gln Ser Arg Pro Glu Pro Thr Ala Pro Pro Glu Glu Ser Phe Arg
    450                 455                 460 ttt ggg gaa gag aca aca act ccc tct cag aag cag gag ccg ata gac     1440
Phe Gly Glu Glu Thr Thr Thr Pro Ser Gln Lys Gln Glu Pro Ile Asp
465                 470                 475                 480 aag gaa ctg tat cct tta gct tcc ctc aga tca ctc ttt ggc agc gac     1488
Lys Glu Leu Tyr Pro Leu Ala Ser Leu Arg Ser Leu Phe Gly Ser Asp
                485                 490                 495 ccc tcg tca caa taa                                                  1503
Pro Ser Ser Gln
            500

<210> SEQ ID NO 5
```

<211> LENGTH: 500
<212> TYPE: PRT
<213> ORGANISM: Artificial Sequence
<220> FEATURE:
<223> OTHER INFORMATION: Codon optimized form of HIV gag coding region

<400> SEQUENCE: 5

```
Met Gly Ala Arg Ala Ser Val Leu Ser Gly Gly Glu Leu Asp Lys Trp
 1               5                  10                  15

Glu Lys Ile Arg Leu Arg Pro Gly Gly Lys Lys Gln Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Ile Ala Val Leu Tyr Cys Val His Gln Arg Ile Asp Val Lys Asp
                85                  90                  95

Thr Lys Glu Ala Leu Asp Lys Ile Glu Glu Gln Asn Lys Ser Lys
            100                 105                 110

Lys Lys Ala Gln Gln Ala Ala Ala Asp Thr Gly Asn Asn Ser Gln Val
        115                 120                 125

Ser Gln Asn Tyr Pro Ile Val Gln Asn Leu Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
                165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
        195                 200                 205

Ala Ala Glu Trp Asp Arg Leu His Pro Val His Ala Gly Pro Ile Ala
    210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr His Asn Pro Pro Ile
                245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
        275                 280                 285

Pro Lys Glu Pro Phe Arg Asp Tyr Val Asp Arg Phe Tyr Lys Thr Leu
    290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
                325                 330                 335

Leu Gly Pro Gly Ala Thr Leu Glu Glu Met Met Thr Ala Cys Gln Gly
            340                 345                 350

Val Gly Gly Pro Gly His Lys Ala Arg Val Leu Ala Glu Ala Met Ser
        355                 360                 365

Gln Val Thr Asn Pro Ala Thr Ile Met Ile Gln Lys Gly Asn Phe Arg
    370                 375                 380
```

```
Asn Gln Arg Lys Thr Val Lys Cys Phe Asn Cys Gly Lys Glu Gly His
385                 390                 395                 400

Ile Ala Lys Asn Cys Arg Ala Pro Arg Lys Gly Cys Trp Lys Cys
                405                 410                 415

Gly Lys Glu Gly His Gln Met Lys Asp Cys Thr Glu Arg Gln Ala Asn
                420                 425                 430

Phe Leu Gly Lys Ile Trp Pro Ser His Lys Gly Arg Pro Gly Asn Phe
                435                 440                 445

Leu Gln Ser Arg Pro Glu Pro Thr Ala Pro Pro Glu Glu Ser Phe Arg
    450                 455                 460

Phe Gly Glu Glu Thr Thr Thr Pro Ser Gln Lys Gln Glu Pro Ile Asp
465                 470                 475                 480

Lys Glu Leu Tyr Pro Leu Ala Ser Leu Arg Ser Leu Phe Gly Ser Asp
                485                 490                 495

Pro Ser Ser Gln
            500

<210> SEQ ID NO 6
<211> LENGTH: 3012
<212> TYPE: DNA
<213> ORGANISM: Homo sapien
<220> FEATURE:
<221> NAME/KEY: CDS
<222> LOCATION: (1)...(3012)

<400> SEQUENCE: 6 ttt ttt agg gaa gat ctg gcc ttc cca caa ggg aag gcc agg gaa ttt      48
Phe Phe Arg Glu Asp Leu Ala Phe Pro Gln Gly Lys Ala Arg Glu Phe
1               5                   10                  15 tct tca gag cag acc aga gcc aac agc ccc acc aga aga gag ctt cag     96
Ser Ser Glu Gln Thr Arg Ala Asn Ser Pro Thr Arg Arg Glu Leu Gln
                20                  25                  30 gtt tgg gga aga gac aac aac tcc ctc tca gaa gca gga gcc gat aga    144
Val Trp Gly Arg Asp Asn Asn Ser Leu Ser Glu Ala Gly Ala Asp Arg
            35                  40                  45 caa gga act gta tcc ttt agc ttc cct cag atc act ctt tgg cag cga    192
Gln Gly Thr Val Ser Phe Ser Phe Pro Gln Ile Thr Leu Trp Gln Arg
        50                  55                  60 ccc ctc gtc aca ata aag ata ggg ggg caa tta aag gaa gct cta tta    240
Pro Leu Val Thr Ile Lys Ile Gly Gly Gln Leu Lys Glu Ala Leu Leu
65                  70                  75                  80 gat aca gga gca gat gat aca gta tta gaa gaa atg aat ttg cca gga    288
Asp Thr Gly Ala Asp Asp Thr Val Leu Glu Glu Met Asn Leu Pro Gly
                85                  90                  95 aga tgg aaa cca aaa atg ata ggg gga att gga ggt ttt atc aaa gta    336
Arg Trp Lys Pro Lys Met Ile Gly Gly Ile Gly Gly Phe Ile Lys Val
            100                 105                 110 gga cag tat gat cag ata ctc ata gaa atc tgc gga cat aaa gct ata    384
Gly Gln Tyr Asp Gln Ile Leu Ile Glu Ile Cys Gly His Lys Ala Ile
        115                 120                 125 ggt aca gta tta gta gga cct aca cct gtc aac ata att gga aga aat    432
Gly Thr Val Leu Val Gly Pro Thr Pro Val Asn Ile Ile Gly Arg Asn
    130                 135                 140 ctg ttg act cag att ggc tgc act tta aat ttt ccc att agt cct att    480
Leu Leu Thr Gln Ile Gly Cys Thr Leu Asn Phe Pro Ile Ser Pro Ile
145                 150                 155                 160 gag act gta cca gta aaa tta aag cca gga atg gat ggc cca aaa gtt    528
Glu Thr Val Pro Val Lys Leu Lys Pro Gly Met Asp Gly Pro Lys Val
                165                 170                 175
```

-continued

| | |
|---|---|
| aaa caa tgg cca ttg aca gaa gaa aaa ata aaa gca tta gta gaa att<br>Lys Gln Trp Pro Leu Thr Glu Glu Lys Ile Lys Ala Leu Val Glu Ile<br>            180                  185                190 | 576 |
| tgt aca gaa atg gaa aag gaa gga aaa att tca aaa att ggg cct gaa<br>Cys Thr Glu Met Glu Lys Glu Gly Lys Ile Ser Lys Ile Gly Pro Glu<br>195                    200                205 | 624 |
| aat cca tac aat act cca gta ttt gcc ata aag aaa aag gac agt act<br>Asn Pro Tyr Asn Thr Pro Val Phe Ala Ile Lys Lys Lys Asp Ser Thr<br>          210                 215             220 | 672 |
| aaa tgg aga aaa tta gta gat ttc aga gaa ctt aat aag aga act caa<br>Lys Trp Arg Lys Leu Val Asp Phe Arg Glu Leu Asn Lys Arg Thr Gln<br>225                  230              235           240 | 720 |
| gat ttc tgg gaa gtt caa tta gga ata cca cat cct gca ggg tta aaa<br>Asp Phe Trp Glu Val Gln Leu Gly Ile Pro His Pro Ala Gly Leu Lys<br>               245                250            255 | 768 |
| cag aaa aaa tca gta aca gta ctg gat gtg ggc gat gca tat ttt tca<br>Gln Lys Lys Ser Val Thr Val Leu Asp Val Gly Asp Ala Tyr Phe Ser<br>          260               265             270 | 816 |
| gtt ccc tta gat aaa gac ttc agg aag tat act gca ttt acc ata cct<br>Val Pro Leu Asp Lys Asp Phe Arg Lys Tyr Thr Ala Phe Thr Ile Pro<br>275                  280              285 | 864 |
| agt ata aac aat gag aca cca ggg att aga tat cag tac aat gtg ctt<br>Ser Ile Asn Asn Glu Thr Pro Gly Ile Arg Tyr Gln Tyr Asn Val Leu<br>          290               295             300 | 912 |
| cca cag gga tgg aaa gga tca cca gca ata ttc cag tgt agc atg aca<br>Pro Gln Gly Trp Lys Gly Ser Pro Ala Ile Phe Gln Cys Ser Met Thr<br>305                  310              315           320 | 960 |
| aaa atc tta gag cct ttt aga aaa caa aat cca gac ata gtc atc tat<br>Lys Ile Leu Glu Pro Phe Arg Lys Gln Asn Pro Asp Ile Val Ile Tyr<br>               325                330            335 | 1008 |
| caa tac atg gat gat ttg tat gta gga tct gac tta gaa ata ggg cag<br>Gln Tyr Met Asp Asp Leu Tyr Val Gly Ser Asp Leu Glu Ile Gly Gln<br>              340               345             350 | 1056 |
| cat aga aca aaa ata gag gaa ctg aga caa cat ctg ttg agg tgg gga<br>His Arg Thr Lys Ile Glu Glu Leu Arg Gln His Leu Leu Arg Trp Gly<br>          355               360             365 | 1104 |
| ttt acc aca cca gac aaa aaa cat cag aaa gaa cct cca ttc ctt tgg<br>Phe Thr Thr Pro Asp Lys Lys His Gln Lys Glu Pro Pro Phe Leu Trp<br>370                  375              380 | 1152 |
| atg ggt tat gaa ctc cat cct gat aaa tgg aca gta cag cct ata gtg<br>Met Gly Tyr Glu Leu His Pro Asp Lys Trp Thr Val Gln Pro Ile Val<br>385                  390              395           400 | 1200 |
| ctg cca gaa aag gac agc tgg act gtc aat gac ata cag aaa tta gtg<br>Leu Pro Glu Lys Asp Ser Trp Thr Val Asn Asp Ile Gln Lys Leu Val<br>               405                410            415 | 1248 |
| gga aaa ttg aat tgg gca agt cag att tat gca ggg att aaa gta agg<br>Gly Lys Leu Asn Trp Ala Ser Gln Ile Tyr Ala Gly Ile Lys Val Arg<br>              420               425             430 | 1296 |
| caa tta tgt aaa ctt ctt agg gga acc aaa gca cta aca gaa gta gta<br>Gln Leu Cys Lys Leu Leu Arg Gly Thr Lys Ala Leu Thr Glu Val Val<br>          435               440             445 | 1344 |
| cca cta aca gaa gaa gca gag cta gaa ctg gca gaa aac agg gag att<br>Pro Leu Thr Glu Glu Ala Glu Leu Glu Leu Ala Glu Asn Arg Glu Ile<br>450                  455              460 | 1392 |
| cta aaa gaa ccg gta cat gga gtg tat tat gac cca tca aaa gac tta<br>Leu Lys Glu Pro Val His Gly Val Tyr Tyr Asp Pro Ser Lys Asp Leu<br>465                  470              475           480 | 1440 |
| ata gca gaa ata cag aag cag ggg caa ggc caa tgg aca tat caa att<br>Ile Ala Glu Ile Gln Lys Gln Gly Gln Gly Gln Trp Thr Tyr Gln Ile | 1488 |

```
                485                 490                 495
tat caa gag cca ttt aaa aat ctg aaa aca gga aaa tat gca aga atg     1536
Tyr Gln Glu Pro Phe Lys Asn Leu Lys Thr Gly Lys Tyr Ala Arg Met
                500                 505                 510 aag ggt gcc cac act aat gat gtg aaa caa tta aca gag gca gta caa     1584
Lys Gly Ala His Thr Asn Asp Val Lys Gln Leu Thr Glu Ala Val Gln
            515                 520                 525 aaa ata gcc aca gaa agc ata gta ata tgg gga aag act cct aaa ttt     1632
Lys Ile Ala Thr Glu Ser Ile Val Ile Trp Gly Lys Thr Pro Lys Phe
        530                 535                 540 aaa tta ccc ata caa aag gaa aca tgg gaa gca tgg tgg aca gag tat     1680
Lys Leu Pro Ile Gln Lys Glu Thr Trp Glu Ala Trp Trp Thr Glu Tyr
545                 550                 555                 560 tgg caa gcc acc tgg att cct gag tgg gag ttt gtc aat acc cct ccc     1728
Trp Gln Ala Thr Trp Ile Pro Glu Trp Glu Phe Val Asn Thr Pro Pro
                565                 570                 575 tta gtg aag tta tgg tac cag tta gag aaa gaa ccc ata ata gga gca     1776
Leu Val Lys Leu Trp Tyr Gln Leu Glu Lys Glu Pro Ile Ile Gly Ala
            580                 585                 590 gaa act ttc tat gta gat ggg gca gcc aat agg gaa act aaa tta gga     1824
Glu Thr Phe Tyr Val Asp Gly Ala Ala Asn Arg Glu Thr Lys Leu Gly
        595                 600                 605 aaa gca gga tat gta act gac aga gga aga caa aaa gtt gtc ccc cta     1872
Lys Ala Gly Tyr Val Thr Asp Arg Gly Arg Gln Lys Val Val Pro Leu
610                 615                 620 acg gac aca aca aat cag aag act gag tta caa gca att cat cta gct     1920
Thr Asp Thr Thr Asn Gln Lys Thr Glu Leu Gln Ala Ile His Leu Ala
625                 630                 635                 640 ttg cag gat tcg gga tta gaa gta aac ata gtg aca gac tca caa tat     1968
Leu Gln Asp Ser Gly Leu Glu Val Asn Ile Val Thr Asp Ser Gln Tyr
                645                 650                 655 gca ttg gga atc att caa gca caa cca gat aag agt gaa tca gag tta     2016
Ala Leu Gly Ile Ile Gln Ala Gln Pro Asp Lys Ser Glu Ser Glu Leu
            660                 665                 670 gtc agt caa ata ata gag cag tta ata aaa aag gaa aaa gtc tac ctg     2064
Val Ser Gln Ile Ile Glu Gln Leu Ile Lys Lys Glu Lys Val Tyr Leu
        675                 680                 685 gca tgg gta cca gca cac aaa gga att gga gga aat gaa caa gta gat     2112
Ala Trp Val Pro Ala His Lys Gly Ile Gly Gly Asn Glu Gln Val Asp
690                 695                 700 ggg ttg gtc agt gct gga atc agg aaa gta cta ttt tta gat gga ata     2160
Gly Leu Val Ser Ala Gly Ile Arg Lys Val Leu Phe Leu Asp Gly Ile
705                 710                 715                 720 gat aag gcc caa gaa gaa cat gag aaa tat cac agt aat tgg aga gca     2208
Asp Lys Ala Gln Glu Glu His Glu Lys Tyr His Ser Asn Trp Arg Ala
                725                 730                 735 atg gct agt gat ttt aac cta cca cct gta gta gca aaa gaa ata gta     2256
Met Ala Ser Asp Phe Asn Leu Pro Pro Val Val Ala Lys Glu Ile Val
            740                 745                 750 gcc agc tgt gat aaa tgt cag cta aaa ggg gaa gcc atg cat gga caa     2304
Ala Ser Cys Asp Lys Cys Gln Leu Lys Gly Glu Ala Met His Gly Gln
        755                 760                 765 gta gac tgt agc cca gga ata tgg cag cta gat tgt aca cat tta gaa     2352
Val Asp Cys Ser Pro Gly Ile Trp Gln Leu Asp Cys Thr His Leu Glu
770                 775                 780 gga aaa gtt atc ttg gta gca gtt cat gta gcc agt gga tat ata gaa     2400
Gly Lys Val Ile Leu Val Ala Val His Val Ala Ser Gly Tyr Ile Glu
785                 790                 795                 800 gca gaa gta att cca gca gag aca ggg caa gaa aca gca tac ttc ctc     2448
```

-continued

| | | |
|---|---|---|
| Ala Glu Val Ile Pro Ala Glu Thr Gly Gln Glu Thr Ala Tyr Phe Leu<br>805 810 815 | | |
| tta aaa tta gca gga aga tgg cca gta aaa aca gta cat aca gac aat<br>Leu Lys Leu Ala Gly Arg Trp Pro Val Lys Thr Val His Thr Asp Asn<br>820 825 830 | | 2496 |
| ggc agc aat ttc acc agt act aca gtt aag gcc gcc tgt tgg tgg gcg<br>Gly Ser Asn Phe Thr Ser Thr Thr Val Lys Ala Ala Cys Trp Trp Ala<br>835 840 845 | | 2544 |
| ggg atc aag cag gaa ttt ggc att ccc tac aat ccc caa agt caa gga<br>Gly Ile Lys Gln Glu Phe Gly Ile Pro Tyr Asn Pro Gln Ser Gln Gly<br>850 855 860 | | 2592 |
| gta ata gaa tct atg aat aaa gaa tta aag aaa att ata gga cag gta<br>Val Ile Glu Ser Met Asn Lys Glu Leu Lys Lys Ile Ile Gly Gln Val<br>865 870 875 880 | | 2640 |
| aga gat cag gct gaa cat ctt aag aca gca gta caa atg gca gta ttc<br>Arg Asp Gln Ala Glu His Leu Lys Thr Ala Val Gln Met Ala Val Phe<br>885 890 895 | | 2688 |
| atc cac aat ttt aaa aga aaa ggg ggg att ggg ggg tac agt gca ggg<br>Ile His Asn Phe Lys Arg Lys Gly Gly Ile Gly Gly Tyr Ser Ala Gly<br>900 905 910 | | 2736 |
| gaa aga ata gta gac ata ata gca aca gac ata caa act aaa gaa tta<br>Glu Arg Ile Val Asp Ile Ile Ala Thr Asp Ile Gln Thr Lys Glu Leu<br>915 920 925 | | 2784 |
| caa aaa caa att aca aaa att caa aat ttt cgg gtt tat tac agg gac<br>Gln Lys Gln Ile Thr Lys Ile Gln Asn Phe Arg Val Tyr Tyr Arg Asp<br>930 935 940 | | 2832 |
| agc aga gat cca gtt tgg aaa gga cca gca aag ctc ctc tgg aaa ggt<br>Ser Arg Asp Pro Val Trp Lys Gly Pro Ala Lys Leu Leu Trp Lys Gly<br>945 950 955 960 | | 2880 |
| gaa ggg gca gta gta ata caa gat aat agt gac ata aaa gta gtg cca<br>Glu Gly Ala Val Val Ile Gln Asp Asn Ser Asp Ile Lys Val Val Pro<br>965 970 975 | | 2928 |
| aga aga aaa gca aag atc atc agg gat tat gga aaa cag atg gca ggt<br>Arg Arg Lys Ala Lys Ile Ile Arg Asp Tyr Gly Lys Gln Met Ala Gly<br>980 985 990 | | 2976 |
| gat gat tgt gtg gca agt aga cag gat gag gat taa<br>Asp Asp Cys Val Ala Ser Arg Gln Asp Glu Asp<br>995 1000 | | 3012 |

<210> SEQ ID NO 7
<211> LENGTH: 1003
<212> TYPE: PRT
<213> ORGANISM: Homo sapien

<400> SEQUENCE: 7

Phe Phe Arg Glu Asp Leu Ala Phe Pro Gln Gly Lys Ala Arg Glu Phe
1               5                   10                  15

Ser Ser Glu Gln Thr Arg Ala Asn Ser Pro Thr Arg Arg Glu Leu Gln
            20                  25                  30

Val Trp Gly Arg Asp Asn Asn Ser Leu Ser Glu Ala Gly Ala Asp Arg
        35                  40                  45

Gln Gly Thr Val Ser Phe Ser Phe Pro Gln Ile Thr Leu Trp Gln Arg
    50                  55                  60

Pro Leu Val Thr Ile Lys Ile Gly Gly Gln Leu Lys Glu Ala Leu Leu
65                  70                  75                  80

Asp Thr Gly Ala Asp Asp Thr Val Leu Glu Glu Met Asn Leu Pro Gly
                85                  90                  95

Arg Trp Lys Pro Lys Met Ile Gly Gly Ile Gly Gly Phe Ile Lys Val
            100                 105                 110

```
Gly Gln Tyr Asp Gln Ile Leu Ile Glu Ile Cys Gly His Lys Ala Ile
            115                 120                 125
Gly Thr Val Leu Val Gly Pro Thr Val Asn Ile Ile Gly Arg Asn
    130                 135                 140
Leu Leu Thr Gln Ile Gly Cys Thr Leu Asn Phe Pro Ile Ser Pro Ile
145                 150                 155                 160
Glu Thr Val Pro Val Lys Leu Lys Pro Gly Met Asp Gly Pro Lys Val
                165                 170                 175
Lys Gln Trp Pro Leu Thr Glu Glu Lys Ile Lys Ala Leu Val Glu Ile
            180                 185                 190
Cys Thr Glu Met Glu Lys Glu Gly Lys Ile Ser Lys Ile Gly Pro Glu
            195                 200                 205
Asn Pro Tyr Asn Thr Pro Val Phe Ala Ile Lys Lys Lys Asp Ser Thr
    210                 215                 220
Lys Trp Arg Lys Leu Val Asp Phe Arg Glu Leu Asn Lys Arg Thr Gln
225                 230                 235                 240
Asp Phe Trp Glu Val Gln Leu Gly Ile Pro His Pro Ala Gly Leu Lys
            245                 250                 255
Gln Lys Lys Ser Val Thr Val Leu Asp Val Gly Asp Ala Tyr Phe Ser
                260                 265                 270
Val Pro Leu Asp Lys Asp Phe Arg Lys Tyr Thr Ala Phe Thr Ile Pro
            275                 280                 285
Ser Ile Asn Asn Glu Thr Pro Gly Ile Arg Tyr Gln Tyr Asn Val Leu
    290                 295                 300
Pro Gln Gly Trp Lys Gly Ser Pro Ala Ile Phe Gln Cys Ser Met Thr
305                 310                 315                 320
Lys Ile Leu Glu Pro Phe Arg Lys Gln Asn Pro Asp Ile Val Ile Tyr
                325                 330                 335
Gln Tyr Met Asp Asp Leu Tyr Val Gly Ser Asp Leu Glu Ile Gly Gln
            340                 345                 350
His Arg Thr Lys Ile Glu Glu Leu Arg Gln His Leu Leu Arg Trp Gly
            355                 360                 365
Phe Thr Thr Pro Asp Lys Lys His Gln Lys Glu Pro Pro Phe Leu Trp
    370                 375                 380
Met Gly Tyr Glu Leu His Pro Asp Lys Trp Thr Val Gln Pro Ile Val
385                 390                 395                 400
Leu Pro Glu Lys Asp Ser Trp Thr Val Asn Asp Ile Gln Lys Leu Val
                405                 410                 415
Gly Lys Leu Asn Trp Ala Ser Gln Ile Tyr Ala Gly Ile Lys Val Arg
            420                 425                 430
Gln Leu Cys Lys Leu Leu Arg Gly Thr Lys Ala Leu Thr Glu Val Val
            435                 440                 445
Pro Leu Thr Glu Glu Ala Glu Leu Glu Leu Ala Glu Asn Arg Glu Ile
    450                 455                 460
Leu Lys Glu Pro Val His Gly Val Tyr Tyr Asp Pro Ser Lys Asp Leu
465                 470                 475                 480
Ile Ala Glu Ile Gln Lys Gln Gly Gln Gly Gln Trp Thr Tyr Gln Ile
                485                 490                 495
Tyr Gln Glu Pro Phe Lys Asn Leu Lys Thr Gly Lys Tyr Ala Arg Met
            500                 505                 510
Lys Gly Ala His Thr Asn Asp Val Lys Gln Leu Thr Glu Ala Val Gln
            515                 520                 525
```

-continued

```
Lys Ile Ala Thr Glu Ser Ile Val Trp Gly Lys Thr Pro Lys Phe
530                 535                 540
Lys Leu Pro Ile Gln Lys Glu Thr Trp Glu Ala Trp Trp Thr Glu Tyr
545                 550                 555                 560
Trp Gln Ala Thr Trp Ile Pro Glu Trp Glu Phe Val Asn Thr Pro Pro
                565                 570                 575
Leu Val Lys Leu Trp Tyr Gln Leu Glu Lys Glu Pro Ile Ile Gly Ala
            580                 585                 590
Glu Thr Phe Tyr Val Asp Gly Ala Ala Asn Arg Glu Thr Lys Leu Gly
        595                 600                 605
Lys Ala Gly Tyr Val Thr Asp Arg Gly Arg Gln Lys Val Val Pro Leu
610                 615                 620
Thr Asp Thr Thr Asn Gln Lys Thr Glu Leu Gln Ala Ile His Leu Ala
625                 630                 635                 640
Leu Gln Asp Ser Gly Leu Glu Val Asn Ile Val Thr Asp Ser Gln Tyr
                645                 650                 655
Ala Leu Gly Ile Ile Gln Ala Gln Pro Asp Lys Ser Glu Ser Glu Leu
            660                 665                 670
Val Ser Gln Ile Ile Glu Gln Leu Ile Lys Lys Glu Lys Val Tyr Leu
        675                 680                 685
Ala Trp Val Pro Ala His Lys Gly Ile Gly Gly Asn Glu Gln Val Asp
690                 695                 700
Gly Leu Val Ser Ala Gly Ile Arg Lys Val Leu Phe Leu Asp Gly Ile
705                 710                 715                 720
Asp Lys Ala Gln Glu Glu His Glu Lys Tyr His Ser Asn Trp Arg Ala
                725                 730                 735
Met Ala Ser Asp Phe Asn Leu Pro Pro Val Val Ala Lys Glu Ile Val
            740                 745                 750
Ala Ser Cys Asp Lys Cys Gln Leu Lys Gly Glu Ala Met His Gly Gln
        755                 760                 765
Val Asp Cys Ser Pro Gly Ile Trp Gln Leu Asp Cys Thr His Leu Glu
770                 775                 780
Gly Lys Val Ile Leu Val Ala Val His Val Ala Ser Gly Tyr Ile Glu
785                 790                 795                 800
Ala Glu Val Ile Pro Ala Glu Thr Gly Gln Glu Thr Ala Tyr Phe Leu
                805                 810                 815
Leu Lys Leu Ala Gly Arg Trp Pro Val Lys Thr Val His Thr Asp Asn
            820                 825                 830
Gly Ser Asn Phe Thr Ser Thr Thr Val Lys Ala Ala Cys Trp Trp Ala
        835                 840                 845
Gly Ile Lys Gln Glu Phe Gly Ile Pro Tyr Asn Pro Gln Ser Gln Gly
850                 855                 860
Val Ile Glu Ser Met Asn Lys Glu Leu Lys Lys Ile Ile Gly Gln Val
865                 870                 875                 880
Arg Asp Gln Ala Glu His Leu Lys Thr Ala Val Gln Met Ala Val Phe
                885                 890                 895
Ile His Asn Phe Lys Arg Lys Gly Gly Ile Gly Gly Tyr Ser Ala Gly
            900                 905                 910
Glu Arg Ile Val Asp Ile Ile Ala Thr Asp Ile Gln Thr Lys Glu Leu
        915                 920                 925
Gln Lys Gln Ile Thr Lys Ile Gln Asn Phe Arg Val Tyr Tyr Arg Asp
930                 935                 940
Ser Arg Asp Pro Val Trp Lys Gly Pro Ala Lys Leu Leu Trp Lys Gly
```

-continued

```
              945                 950                 955                 960
              Glu Gly Ala Val Val Ile Gln Asp Asn Ser Asp Ile Lys Val Pro
                              965                 970                 975
              Arg Arg Lys Ala Lys Ile Ile Arg Asp Tyr Gly Lys Gln Met Ala Gly
                              980                 985                 990
              Asp Asp Cys Val Ala Ser Arg Gln Asp Glu Asp
                              995                 1000

<210> SEQ ID NO 8
<211> LENGTH: 3012
<212> TYPE: DNA
<213> ORGANISM: Homo sapien
<220> FEATURE:
<221> NAME/KEY: CDS
<222> LOCATION: (1)...(3012)

<400> SEQUENCE: 8 ttt ttt agg gaa gat ctg gcc ttc cca caa ggg aag gcc agg gaa ttt        48
Phe Phe Arg Glu Asp Leu Ala Phe Pro Gln Gly Lys Ala Arg Glu Phe
  1               5                  10                  15 tct tca gag cag acc aga gcc aac agc ccc acc aga aga gag ctt cag        96
Ser Ser Glu Gln Thr Arg Ala Asn Ser Pro Thr Arg Arg Glu Leu Gln
              20                  25                  30 gtt tgg gga aga gac aac aac tcc ctc tca gaa gca gga gcc gat aga       144
Val Trp Gly Arg Asp Asn Asn Ser Leu Ser Glu Ala Gly Ala Asp Arg
          35                  40                  45 caa gga act gta tcc ttt agc ttc cct cag atc act ctt tgg cag cga       192
Gln Gly Thr Val Ser Phe Ser Phe Pro Gln Ile Thr Leu Trp Gln Arg
      50                  55                  60 ccc ctc gtc aca ata aag ata ggg ggg caa tta aag gaa gct cta tta       240
Pro Leu Val Thr Ile Lys Ile Gly Gly Gln Leu Lys Glu Ala Leu Leu
 65                  70                  75                  80 gat aca gga gca gat gat aca gta tta gaa gaa atg aat ttg cca gga       288
Asp Thr Gly Ala Asp Asp Thr Val Leu Glu Glu Met Asn Leu Pro Gly
                  85                  90                  95 aga tgg aaa cca aaa atg ata ggg gga att gga ggt ttt atc aaa gta       336
Arg Trp Lys Pro Lys Met Ile Gly Gly Ile Gly Gly Phe Ile Lys Val
             100                 105                 110 aga cag tat gat cag ata ctc ata gaa atc tgc gga cat aaa gct ata       384
Arg Gln Tyr Asp Gln Ile Leu Ile Glu Ile Cys Gly His Lys Ala Ile
         115                 120                 125 ggt aca gta tta gta gga cct aca cct gtc aac ata att gga aga aat       432
Gly Thr Val Leu Val Gly Pro Thr Pro Val Asn Ile Ile Gly Arg Asn
     130                 135                 140 ctg ttg act cag att ggc tgc act tta aat ttt ccc att agt cct att       480
Leu Leu Thr Gln Ile Gly Cys Thr Leu Asn Phe Pro Ile Ser Pro Ile
145                 150                 155                 160 gag act gta cca gta aaa tta aag cca gga atg gat ggc cca aaa gtt       528
Glu Thr Val Pro Val Lys Leu Lys Pro Gly Met Asp Gly Pro Lys Val
                 165                 170                 175 aaa caa tgg cca ttg aca gaa gaa aaa ata aaa gca tta gta gaa att       576
Lys Gln Trp Pro Leu Thr Glu Glu Lys Ile Lys Ala Leu Val Glu Ile
             180                 185                 190 tgt aca gaa atg gaa aag gaa gga aaa att tca aaa att ggg cct gaa       624
Cys Thr Glu Met Glu Lys Glu Gly Lys Ile Ser Lys Ile Gly Pro Glu
         195                 200                 205 aat cca tac aat act cca gta ttt gcc ata aag aaa aaa gac agt act       672
Asn Pro Tyr Asn Thr Pro Val Phe Ala Ile Lys Lys Lys Asp Ser Thr
     210                 215                 220 aaa tgg aga aaa tta gta gat ttc aga gaa ctt aat aag aga act caa       720
```

| | | | | | | | | | | | | | | | |
|---|---|---|---|---|---|---|---|---|---|---|---|---|---|---|---|
| Lys | Trp | Arg | Lys | Leu | Val | Asp | Phe | Arg | Glu | Leu | Asn | Lys | Arg | Thr | Gln |
| 225 | | | | 230 | | | | 235 | | | | 240 | | | |

| gat | ttc | tgg | gaa | gtt | caa | tta | gga | ata | cca | cat | cct | gca | ggg | tta | aaa | 768 |
|---|---|---|---|---|---|---|---|---|---|---|---|---|---|---|---|---|
| Asp | Phe | Trp | Glu | Val | Gln | Leu | Gly | Ile | Pro | His | Pro | Ala | Gly | Leu | Lys | |
| | | | 245 | | | | 250 | | | | 255 | | | | | |

| cag | aaa | aaa | tca | gta | aca | gta | ctg | gat | gtg | ggc | gat | gca | tat | ttt | tca | 816 |
|---|---|---|---|---|---|---|---|---|---|---|---|---|---|---|---|---|
| Gln | Lys | Lys | Ser | Val | Thr | Val | Leu | Asp | Val | Gly | Asp | Ala | Tyr | Phe | Ser | |
| | | | 260 | | | | 265 | | | | 270 | | | | | |

| gtt | ccc | tta | gat | aaa | gac | ttc | agg | aag | tat | act | gca | ttt | acc | ata | cct | 864 |
|---|---|---|---|---|---|---|---|---|---|---|---|---|---|---|---|---|
| Val | Pro | Leu | Asp | Lys | Asp | Phe | Arg | Lys | Tyr | Thr | Ala | Phe | Thr | Ile | Pro | |
| | | 275 | | | | 280 | | | | 285 | | | | | | |

| agt | ata | aac | aat | gag | aca | cca | ggg | att | aga | tat | cag | tac | aat | gtg | ctt | 912 |
|---|---|---|---|---|---|---|---|---|---|---|---|---|---|---|---|---|
| Ser | Ile | Asn | Asn | Glu | Thr | Pro | Gly | Ile | Arg | Tyr | Gln | Tyr | Asn | Val | Leu | |
| | 290 | | | | 295 | | | | 300 | | | | | | | |

| cca | cag | gga | tgg | aaa | gga | tca | cca | gca | ata | ttc | cag | tgt | agc | atg | aca | 960 |
|---|---|---|---|---|---|---|---|---|---|---|---|---|---|---|---|---|
| Pro | Gln | Gly | Trp | Lys | Gly | Ser | Pro | Ala | Ile | Phe | Gln | Cys | Ser | Met | Thr | |
| 305 | | | | 310 | | | | 315 | | | | 320 | | | | |

| aaa | atc | tta | gag | cct | ttt | aga | aaa | caa | aat | cca | gac | ata | gtc | atc | tat | 1008 |
|---|---|---|---|---|---|---|---|---|---|---|---|---|---|---|---|---|
| Lys | Ile | Leu | Glu | Pro | Phe | Arg | Lys | Gln | Asn | Pro | Asp | Ile | Val | Ile | Tyr | |
| | | | 325 | | | | 330 | | | | 335 | | | | | |

| caa | tac | atg | gat | gat | ttg | tat | gta | gga | tct | gac | tta | gaa | ata | ggg | cag | 1056 |
|---|---|---|---|---|---|---|---|---|---|---|---|---|---|---|---|---|
| Gln | Tyr | Met | Asp | Asp | Leu | Tyr | Val | Gly | Ser | Asp | Leu | Glu | Ile | Gly | Gln | |
| | | 340 | | | | 345 | | | | 350 | | | | | | |

| cat | aga | aca | aaa | ata | gag | gaa | ctg | aga | caa | cat | ctg | ttg | agg | tgg | gga | 1104 |
|---|---|---|---|---|---|---|---|---|---|---|---|---|---|---|---|---|
| His | Arg | Thr | Lys | Ile | Glu | Glu | Leu | Arg | Gln | His | Leu | Leu | Arg | Trp | Gly | |
| | 355 | | | | 360 | | | | 365 | | | | | | | |

| ttt | acc | aca | cca | gac | aaa | aaa | cat | cag | aaa | gaa | cct | cca | ttc | ctt | tgg | 1152 |
|---|---|---|---|---|---|---|---|---|---|---|---|---|---|---|---|---|
| Phe | Thr | Thr | Pro | Asp | Lys | Lys | His | Gln | Lys | Glu | Pro | Pro | Phe | Leu | Trp | |
| 370 | | | | 375 | | | | 380 | | | | | | | | |

| atg | ggt | tat | gaa | ctc | cat | cct | gat | aaa | tgg | aca | gta | cag | cct | ata | gtg | 1200 |
|---|---|---|---|---|---|---|---|---|---|---|---|---|---|---|---|---|
| Met | Gly | Tyr | Glu | Leu | His | Pro | Asp | Lys | Trp | Thr | Val | Gln | Pro | Ile | Val | |
| 385 | | | | 390 | | | | 395 | | | | 400 | | | | |

| ctg | cca | gaa | aag | gac | agc | tgg | act | gtc | aat | gac | ata | cag | aaa | tta | gtg | 1248 |
|---|---|---|---|---|---|---|---|---|---|---|---|---|---|---|---|---|
| Leu | Pro | Glu | Lys | Asp | Ser | Trp | Thr | Val | Asn | Asp | Ile | Gln | Lys | Leu | Val | |
| | | | 405 | | | | 410 | | | | 415 | | | | | |

| gga | aaa | ttg | aat | tgg | gca | agt | cag | att | tat | gca | ggg | att | aaa | gta | agg | 1296 |
|---|---|---|---|---|---|---|---|---|---|---|---|---|---|---|---|---|
| Gly | Lys | Leu | Asn | Trp | Ala | Ser | Gln | Ile | Tyr | Ala | Gly | Ile | Lys | Val | Arg | |
| | | | 420 | | | | 425 | | | | 430 | | | | | |

| caa | tta | tgt | aaa | ctt | ctt | agg | gga | acc | aaa | gca | cta | aca | gaa | gta | gta | 1344 |
|---|---|---|---|---|---|---|---|---|---|---|---|---|---|---|---|---|
| Gln | Leu | Cys | Lys | Leu | Leu | Arg | Gly | Thr | Lys | Ala | Leu | Thr | Glu | Val | Val | |
| | | | 435 | | | | 440 | | | | 445 | | | | | |

| cca | cta | aca | gaa | gaa | gca | gag | cta | gaa | ctg | gca | gaa | aac | agg | gag | att | 1392 |
|---|---|---|---|---|---|---|---|---|---|---|---|---|---|---|---|---|
| Pro | Leu | Thr | Glu | Glu | Ala | Glu | Leu | Glu | Leu | Ala | Glu | Asn | Arg | Glu | Ile | |
| | 450 | | | | 455 | | | | 460 | | | | | | | |

| cta | aaa | gaa | ccg | gta | cat | gga | gtg | tat | tat | gac | cca | tca | aaa | gac | tta | 1440 |
|---|---|---|---|---|---|---|---|---|---|---|---|---|---|---|---|---|
| Leu | Lys | Glu | Pro | Val | His | Gly | Val | Tyr | Tyr | Asp | Pro | Ser | Lys | Asp | Leu | |
| 465 | | | | 470 | | | | 475 | | | | 480 | | | | |

| ata | gca | gaa | ata | cag | aag | cag | ggg | caa | ggc | caa | tgg | aca | tat | caa | att | 1488 |
|---|---|---|---|---|---|---|---|---|---|---|---|---|---|---|---|---|
| Ile | Ala | Glu | Ile | Gln | Lys | Gln | Gly | Gln | Gly | Gln | Trp | Thr | Tyr | Gln | Ile | |
| | | | 485 | | | | 490 | | | | 495 | | | | | |

| tat | caa | gag | cca | ttt | aaa | aat | ctg | aaa | aca | gga | aaa | tat | gca | aga | atg | 1536 |
|---|---|---|---|---|---|---|---|---|---|---|---|---|---|---|---|---|
| Tyr | Gln | Glu | Pro | Phe | Lys | Asn | Leu | Lys | Thr | Gly | Lys | Tyr | Ala | Arg | Met | |
| | | | 500 | | | | 505 | | | | 510 | | | | | |

| aag | ggt | gcc | cac | act | aat | gat | gtg | aaa | caa | tta | aca | gag | gca | gta | caa | 1584 |
|---|---|---|---|---|---|---|---|---|---|---|---|---|---|---|---|---|
| Lys | Gly | Ala | His | Thr | Asn | Asp | Val | Lys | Gln | Leu | Thr | Glu | Ala | Val | Gln | |
| | | 515 | | | | 520 | | | | 525 | | | | | | |

| aaa | ata | gcc | aca | gaa | agc | ata | gta | ata | tgg | gga | aag | act | cct | aaa | ttt | 1632 |
|---|---|---|---|---|---|---|---|---|---|---|---|---|---|---|---|---|
| Lys | Ile | Ala | Thr | Glu | Ser | Ile | Val | Ile | Trp | Gly | Lys | Thr | Pro | Lys | Phe | |
| | 530 | | | | 535 | | | | 540 | | | | | | | |

-continued

| | | |
|---|---|---|
| aaa tta ccc ata caa aag gaa aca tgg gaa gca tgg tgg aca gag tat<br>Lys Leu Pro Ile Gln Lys Glu Thr Trp Glu Ala Trp Trp Thr Glu Tyr<br>545                         550                       555                   560 | | 1680 |
| tgg caa gcc acc tgg att cct gag tgg gag ttt gtc aat acc cct ccc<br>Trp Gln Ala Thr Trp Ile Pro Glu Trp Glu Phe Val Asn Thr Pro Pro<br>                565                       570                       575 | | 1728 |
| tta gtg aag tta tgg tac cag tta gag aaa gaa ccc ata ata gga gca<br>Leu Val Lys Leu Trp Tyr Gln Leu Glu Lys Glu Pro Ile Ile Gly Ala<br>           580                       585                     590 | | 1776 |
| gaa act ttc tat gta gat ggg gca gcc aat agg gaa act aaa tta gga<br>Glu Thr Phe Tyr Val Asp Gly Ala Ala Asn Arg Glu Thr Lys Leu Gly<br>         595                       600                     605 | | 1824 |
| aaa gca gga tat gta act gac aga gga aga caa aaa gtt gtc ccc cta<br>Lys Ala Gly Tyr Val Thr Asp Arg Gly Arg Gln Lys Val Val Pro Leu<br>610                         615                       620 | | 1872 |
| acg gac aca aca aat cag aag act gag tta caa gca att cat cta gct<br>Thr Asp Thr Thr Asn Gln Lys Thr Glu Leu Gln Ala Ile His Leu Ala<br>625                         630                       635                   640 | | 1920 |
| ttg cag gat tcg gga tta gaa gta aac ata gtg aca gac tca caa tat<br>Leu Gln Asp Ser Gly Leu Glu Val Asn Ile Val Thr Asp Ser Gln Tyr<br>                645                       650                     655 | | 1968 |
| gca ttg gga atc att caa gca caa cca gat aag agt gaa tca gag tta<br>Ala Leu Gly Ile Ile Gln Ala Gln Pro Asp Lys Ser Glu Ser Glu Leu<br>           660                       665                     670 | | 2016 |
| gtc agt caa ata ata gag cag tta ata aaa aag gaa aaa gtc tac ctg<br>Val Ser Gln Ile Ile Glu Gln Leu Ile Lys Lys Glu Lys Val Tyr Leu<br>        675                       680                     685 | | 2064 |
| gca tgg gta cca gca cac aaa gga att gga gga aat gaa caa gta gat<br>Ala Trp Val Pro Ala His Lys Gly Ile Gly Gly Asn Glu Gln Val Asp<br>690                         695                       700 | | 2112 |
| aag ttg gtc agt gct gga atc agg aaa gta cta ttt tta gat gga ata<br>Lys Leu Val Ser Ala Gly Ile Arg Lys Val Leu Phe Leu Asp Gly Ile<br>705                         710                       715                   720 | | 2160 |
| gat aag gcc caa gaa gaa cat gag aaa tat cac agt aat tgg aga gca<br>Asp Lys Ala Gln Glu Glu His Glu Lys Tyr His Ser Asn Trp Arg Ala<br>                725                       730                     735 | | 2208 |
| atg gct agt gat ttt aac cta cca cct gta gta gca aaa gaa ata gta<br>Met Ala Ser Asp Phe Asn Leu Pro Pro Val Val Ala Lys Glu Ile Val<br>           740                       745                     750 | | 2256 |
| gcc agc tgt gat aaa tgt cag cta aaa ggg gaa gcc atg cat gga caa<br>Ala Ser Cys Asp Lys Cys Gln Leu Lys Gly Glu Ala Met His Gly Gln<br>        755                       760                     765 | | 2304 |
| gta gac tgt agc cca gga ata tgg cag cta gat tgt aca cat tta gaa<br>Val Asp Cys Ser Pro Gly Ile Trp Gln Leu Asp Cys Thr His Leu Glu<br>770                         775                       780 | | 2352 |
| gga aaa gtt atc ttg gta gca gtt cat gta gcc agt gga tat ata gaa<br>Gly Lys Val Ile Leu Val Ala Val His Val Ala Ser Gly Tyr Ile Glu<br>785                         790                       795                   800 | | 2400 |
| gca gaa gta att cca gca gag aca ggg caa gaa aca gca tac ttc ctc<br>Ala Glu Val Ile Pro Ala Glu Thr Gly Gln Glu Thr Ala Tyr Phe Leu<br>                805                       810                     815 | | 2448 |
| tta aaa tta gca gga aga tgg cca gta aaa aca gta cat aca gac aat<br>Leu Lys Leu Ala Gly Arg Trp Pro Val Lys Thr Val His Thr Asp Asn<br>           820                       825                     830 | | 2496 |
| ggc agc aat ttc acc agt act aca gtt aag gcc gcc tgt tgg tgg gcg<br>Gly Ser Asn Phe Thr Ser Thr Thr Val Lys Ala Ala Cys Trp Trp Ala<br>        835                       840                     845 | | 2544 |
| ggg atc aag cag gaa ttt ggc att ccc tac aat ccc caa agt caa gga<br>Gly Ile Lys Gln Glu Phe Gly Ile Pro Tyr Asn Pro Gln Ser Gln Gly<br>850                         855                       860 | | 2592 |

-continued

```
gta ata gaa tct atg aat aaa gaa tta aag aaa att ata gga cag gta      2640
Val Ile Glu Ser Met Asn Lys Glu Leu Lys Lys Ile Ile Gly Gln Val
865             870                 875                 880 aga gat cag gct gaa cat ctt aag aca gca gta caa atg gca gta ttc      2688
Arg Asp Gln Ala Glu His Leu Lys Thr Ala Val Gln Met Ala Val Phe
            885                 890                 895 atc cac aat ttt aaa aga aaa ggg ggg att ggg ggg tac agt gca ggg      2736
Ile His Asn Phe Lys Arg Lys Gly Gly Ile Gly Gly Tyr Ser Ala Gly
        900                 905                 910 gaa aga ata gta gac ata ata gca aca gac ata caa act aaa gaa tta      2784
Glu Arg Ile Val Asp Ile Ile Ala Thr Asp Ile Gln Thr Lys Glu Leu
    915                 920                 925 caa aaa caa att aca aaa att caa aat ttt cgg gtt tat tac agg gac      2832
Gln Lys Gln Ile Thr Lys Ile Gln Asn Phe Arg Val Tyr Tyr Arg Asp
930                 935                 940 agc aga gat cca gtt tgg aaa gga cca gca aag ctc ctc tgg aaa ggt      2880
Ser Arg Asp Pro Val Trp Lys Gly Pro Ala Lys Leu Leu Trp Lys Gly
945                 950                 955                 960 gaa ggg gca gta gta ata caa gat aat agt gac ata aaa gta gtg cca      2928
Glu Gly Ala Val Val Ile Gln Asp Asn Ser Asp Ile Lys Val Val Pro
                965                 970                 975 aga aga aaa gca aag atc atc agg gat tat gga aaa cag atg gca ggt      2976
Arg Arg Lys Ala Lys Ile Ile Arg Asp Tyr Gly Lys Gln Met Ala Gly
            980                 985                 990 gat gat tgt gtg gca agt aga cag gat gag gat taa                      3012
Asp Asp Cys Val Ala Ser Arg Gln Asp Glu Asp
        995                 1000
```

<210> SEQ ID NO 9
<211> LENGTH: 1003
<212> TYPE: PRT
<213> ORGANISM: Homo sapien

<400> SEQUENCE: 9

```
Phe Phe Arg Glu Asp Leu Ala Phe Pro Gln Gly Lys Ala Arg Glu Phe
1               5                   10                  15

Ser Ser Glu Gln Thr Arg Ala Asn Ser Pro Thr Arg Arg Glu Leu Gln
            20                  25                  30

Val Trp Gly Arg Asp Asn Asn Ser Leu Ser Glu Ala Gly Ala Asp Arg
        35                  40                  45

Gln Gly Thr Val Ser Phe Ser Phe Pro Gln Ile Thr Leu Trp Gln Arg
    50                  55                  60

Pro Leu Val Thr Ile Lys Ile Gly Gly Gln Leu Lys Glu Ala Leu Leu
65                  70                  75                  80

Asp Thr Gly Ala Asp Asp Thr Val Leu Glu Glu Met Asn Leu Pro Gly
                85                  90                  95

Arg Trp Lys Pro Lys Met Ile Gly Gly Ile Gly Gly Phe Ile Lys Val
            100                 105                 110

Arg Gln Tyr Asp Gln Ile Leu Ile Glu Ile Cys Gly His Lys Ala Ile
        115                 120                 125

Gly Thr Val Leu Val Gly Pro Thr Pro Val Asn Ile Ile Gly Arg Asn
    130                 135                 140

Leu Leu Thr Gln Ile Gly Cys Thr Leu Asn Phe Pro Ile Ser Pro Ile
145                 150                 155                 160

Glu Thr Val Pro Val Lys Leu Lys Pro Gly Met Asp Gly Pro Lys Val
                165                 170                 175

Lys Gln Trp Pro Leu Thr Glu Glu Lys Ile Lys Ala Leu Val Glu Ile
```

-continued

```
              180                 185                 190
Cys Thr Glu Met Glu Lys Glu Gly Lys Ile Ser Lys Ile Gly Pro Glu
            195                 200                 205
Asn Pro Tyr Asn Thr Pro Val Phe Ala Ile Lys Lys Asp Ser Thr
        210                 215                 220
Lys Trp Arg Lys Leu Val Asp Phe Arg Glu Leu Asn Lys Arg Thr Gln
225                 230                 235                 240
Asp Phe Trp Glu Val Gln Leu Gly Ile Pro His Pro Ala Gly Leu Lys
                245                 250                 255
Gln Lys Lys Ser Val Thr Val Leu Asp Val Gly Asp Ala Tyr Phe Ser
            260                 265                 270
Val Pro Leu Asp Lys Asp Phe Arg Lys Tyr Thr Ala Phe Thr Ile Pro
        275                 280                 285
Ser Ile Asn Asn Glu Thr Pro Gly Ile Arg Tyr Gln Tyr Asn Val Leu
    290                 295                 300
Pro Gln Gly Trp Lys Gly Ser Pro Ala Ile Phe Gln Cys Ser Met Thr
305                 310                 315                 320
Lys Ile Leu Glu Pro Phe Arg Lys Gln Asn Pro Asp Ile Val Ile Tyr
                325                 330                 335
Gln Tyr Met Asp Asp Leu Tyr Val Gly Ser Asp Leu Glu Ile Gly Gln
            340                 345                 350
His Arg Thr Lys Ile Glu Glu Leu Arg Gln His Leu Leu Arg Trp Gly
        355                 360                 365
Phe Thr Thr Pro Asp Lys Lys His Gln Lys Glu Pro Pro Phe Leu Trp
370                 375                 380
Met Gly Tyr Glu Leu His Pro Asp Lys Trp Thr Val Gln Pro Ile Val
385                 390                 395                 400
Leu Pro Glu Lys Asp Ser Trp Thr Val Asn Asp Ile Gln Lys Leu Val
                405                 410                 415
Gly Lys Leu Asn Trp Ala Ser Gln Ile Tyr Ala Gly Ile Lys Val Arg
            420                 425                 430
Gln Leu Cys Lys Leu Leu Arg Gly Thr Lys Ala Leu Thr Glu Val Val
        435                 440                 445
Pro Leu Thr Glu Glu Ala Glu Leu Glu Leu Ala Glu Asn Arg Glu Ile
    450                 455                 460
Leu Lys Glu Pro Val His Gly Val Tyr Tyr Asp Pro Ser Lys Asp Leu
465                 470                 475                 480
Ile Ala Glu Ile Gln Lys Gln Gly Gln Gly Gln Trp Thr Tyr Gln Ile
                485                 490                 495
Tyr Gln Glu Pro Phe Lys Asn Leu Lys Thr Gly Lys Tyr Ala Arg Met
            500                 505                 510
Lys Gly Ala His Thr Asn Asp Val Lys Gln Leu Thr Glu Ala Val Gln
        515                 520                 525
Lys Ile Ala Thr Glu Ser Ile Val Ile Trp Gly Lys Thr Pro Lys Phe
    530                 535                 540
Lys Leu Pro Ile Gln Lys Glu Thr Trp Glu Ala Trp Trp Thr Glu Tyr
545                 550                 555                 560
Trp Gln Ala Thr Trp Ile Pro Glu Trp Glu Phe Val Asn Thr Pro Pro
                565                 570                 575
Leu Val Lys Leu Trp Tyr Gln Leu Glu Lys Glu Pro Ile Ile Gly Ala
            580                 585                 590
Glu Thr Phe Tyr Val Asp Gly Ala Ala Asn Arg Glu Thr Lys Leu Gly
        595                 600                 605
```

```
Lys Ala Gly Tyr Val Thr Asp Arg Gly Arg Gln Lys Val Pro Leu
    610                 615                 620

Thr Asp Thr Thr Asn Gln Lys Thr Glu Leu Gln Ala Ile His Leu Ala
625                 630                 635                 640

Leu Gln Asp Ser Gly Leu Glu Val Asn Ile Val Thr Asp Ser Gln Tyr
                645                 650                 655

Ala Leu Gly Ile Ile Gln Ala Gln Pro Asp Lys Ser Glu Ser Glu Leu
            660                 665                 670

Val Ser Gln Ile Ile Glu Gln Leu Ile Lys Lys Glu Lys Val Tyr Leu
        675                 680                 685

Ala Trp Val Pro Ala His Lys Gly Ile Gly Gly Asn Glu Gln Val Asp
    690                 695                 700

Lys Leu Val Ser Ala Gly Ile Arg Lys Val Leu Phe Leu Asp Gly Ile
705                 710                 715                 720

Asp Lys Ala Gln Glu Glu His Glu Lys Tyr His Ser Asn Trp Arg Ala
                725                 730                 735

Met Ala Ser Asp Phe Asn Leu Pro Pro Val Val Ala Lys Glu Ile Val
            740                 745                 750

Ala Ser Cys Asp Lys Cys Gln Leu Lys Gly Glu Ala Met His Gly Gln
        755                 760                 765

Val Asp Cys Ser Pro Gly Ile Trp Gln Leu Asp Cys Thr His Leu Glu
    770                 775                 780

Gly Lys Val Ile Leu Val Ala Val His Val Ala Ser Gly Tyr Ile Glu
785                 790                 795                 800

Ala Glu Val Ile Pro Ala Glu Thr Gly Gln Glu Thr Ala Tyr Phe Leu
                805                 810                 815

Leu Lys Leu Ala Gly Arg Trp Pro Val Lys Thr Val His Thr Asp Asn
            820                 825                 830

Gly Ser Asn Phe Thr Ser Thr Thr Val Lys Ala Ala Cys Trp Trp Ala
        835                 840                 845

Gly Ile Lys Gln Glu Phe Gly Ile Pro Tyr Asn Pro Gln Ser Gln Gly
    850                 855                 860

Val Ile Glu Ser Met Asn Lys Glu Leu Lys Lys Ile Ile Gly Gln Val
865                 870                 875                 880

Arg Asp Gln Ala Glu His Leu Lys Thr Ala Val Gln Met Ala Val Phe
                885                 890                 895

Ile His Asn Phe Lys Arg Lys Gly Gly Ile Gly Gly Tyr Ser Ala Gly
            900                 905                 910

Glu Arg Ile Val Asp Ile Ile Ala Thr Asp Ile Gln Thr Lys Glu Leu
        915                 920                 925

Gln Lys Gln Ile Thr Lys Ile Gln Asn Phe Arg Val Tyr Tyr Arg Asp
    930                 935                 940

Ser Arg Asp Pro Val Trp Lys Gly Pro Ala Lys Leu Leu Trp Lys Gly
945                 950                 955                 960

Glu Gly Ala Val Val Ile Gln Asp Asn Ser Asp Ile Lys Val Val Pro
                965                 970                 975

Arg Arg Lys Ala Lys Ile Ile Arg Asp Tyr Gly Lys Gln Met Ala Gly
            980                 985                 990

Asp Asp Cys Val Ala Ser Arg Gln Asp Glu Asp
            995                 1000
```

<210> SEQ ID NO 10
<211> LENGTH: 3012

<212> TYPE: DNA
<213> ORGANISM: Artificial Sequence
<220> FEATURE:
<223> OTHER INFORMATION: Codon optimized form of HIV pol coding region
<220> FEATURE:
<221> NAME/KEY: CDS
<222> LOCATION: (1)...(3012)

<400> SEQUENCE: 10

| | | | | | | | | | | | | | | | | |
|---|---|---|---|---|---|---|---|---|---|---|---|---|---|---|---|---|
| ttt | ttt | agg | gaa | gat | ctg | gcc | ttc | cca | caa | ggg | aag | gcc | agg | gaa | ttt | 48 |
| Phe | Phe | Arg | Glu | Asp | Leu | Ala | Phe | Pro | Gln | Gly | Lys | Ala | Arg | Glu | Phe | |
| 1 | | | | 5 | | | | | 10 | | | | | 15 | | |
| tct | tca | gag | cag | acc | aga | gcc | aac | agc | ccc | acc | aga | aga | gag | ctt | cag | 96 |
| Ser | Ser | Glu | Gln | Thr | Arg | Ala | Asn | Ser | Pro | Thr | Arg | Arg | Glu | Leu | Gln | |
| | | | 20 | | | | | 25 | | | | | 30 | | | |
| gtt | tgg | gga | aga | gac | aac | aac | tcc | ctc | tca | gaa | gca | gga | gcc | gat | aga | 144 |
| Val | Trp | Gly | Arg | Asp | Asn | Asn | Ser | Leu | Ser | Glu | Ala | Gly | Ala | Asp | Arg | |
| | | 35 | | | | | 40 | | | | | 45 | | | | |
| caa | gga | act | gta | tcc | ttt | agc | ttc | cct | cag | atc | act | ctt | tgg | cag | cga | 192 |
| Gln | Gly | Thr | Val | Ser | Phe | Ser | Phe | Pro | Gln | Ile | Thr | Leu | Trp | Gln | Arg | |
| | 50 | | | | | 55 | | | | | 60 | | | | | |
| ccc | ctc | gtc | aca | ata | aag | atc | ggt | ggc | cag | ctg | aag | gag | gcc | ctg | ctg | 240 |
| Pro | Leu | Val | Thr | Ile | Lys | Ile | Gly | Gly | Gln | Leu | Lys | Glu | Ala | Leu | Leu | |
| 65 | | | | | 70 | | | | | 75 | | | | | 80 | |
| gac | acc | ggc | gcc | gac | gac | acc | gtg | ctg | gag | gag | atg | aac | ctg | ccc | ggc | 288 |
| Asp | Thr | Gly | Ala | Asp | Asp | Thr | Val | Leu | Glu | Glu | Met | Asn | Leu | Pro | Gly | |
| | | | | 85 | | | | | 90 | | | | | 95 | | |
| cgc | tgg | aag | ccc | aag | atg | atc | ggc | ggc | atc | ggc | ggc | ttc | atc | aaa | gtc | 336 |
| Arg | Trp | Lys | Pro | Lys | Met | Ile | Gly | Gly | Ile | Gly | Gly | Phe | Ile | Lys | Val | |
| | | | 100 | | | | | 105 | | | | | 110 | | | |
| cgc | cag | tac | gac | cag | atc | ctg | atc | gag | atc | tgc | ggc | cac | aag | gcc | atc | 384 |
| Arg | Gln | Tyr | Asp | Gln | Ile | Leu | Ile | Glu | Ile | Cys | Gly | His | Lys | Ala | Ile | |
| | | 115 | | | | | 120 | | | | | 125 | | | | |
| ggc | acc | gtg | ctg | gtg | ggc | ccc | acc | ccc | gtg | aac | atc | atc | ggc | cgc | aac | 432 |
| Gly | Thr | Val | Leu | Val | Gly | Pro | Thr | Pro | Val | Asn | Ile | Ile | Gly | Arg | Asn | |
| | 130 | | | | | 135 | | | | | 140 | | | | | |
| ctg | ctg | acc | cag | atc | ggc | tgc | acc | ctg | aac | ttc | ccc | atc | tcc | ccc | atc | 480 |
| Leu | Leu | Thr | Gln | Ile | Gly | Cys | Thr | Leu | Asn | Phe | Pro | Ile | Ser | Pro | Ile | |
| 145 | | | | | 150 | | | | | 155 | | | | | 160 | |
| gag | acc | gtg | ccc | gtg | aag | ctg | aag | ccc | ggc | atg | gac | ggc | ccc | aaa | gtc | 528 |
| Glu | Thr | Val | Pro | Val | Lys | Leu | Lys | Pro | Gly | Met | Asp | Gly | Pro | Lys | Val | |
| | | | | 165 | | | | | 170 | | | | | 175 | | |
| aag | cag | tgg | ccc | ctg | acc | gag | gag | aag | atc | aag | gcc | ctg | gtg | gag | atc | 576 |
| Lys | Gln | Trp | Pro | Leu | Thr | Glu | Glu | Lys | Ile | Lys | Ala | Leu | Val | Glu | Ile | |
| | | | 180 | | | | | 185 | | | | | 190 | | | |
| tgc | acc | gag | atg | gag | aag | gag | ggc | aag | atc | tcc | aag | atc | ggc | ccc | gag | 624 |
| Cys | Thr | Glu | Met | Glu | Lys | Glu | Gly | Lys | Ile | Ser | Lys | Ile | Gly | Pro | Glu | |
| | | 195 | | | | | 200 | | | | | 205 | | | | |
| aac | ccc | tac | aac | acc | ccc | gtg | ttc | gcc | atc | aag | aag | aag | gac | tcc | acc | 672 |
| Asn | Pro | Tyr | Asn | Thr | Pro | Val | Phe | Ala | Ile | Lys | Lys | Lys | Asp | Ser | Thr | |
| | 210 | | | | | 215 | | | | | 220 | | | | | |
| aag | tgg | cgc | aag | ctg | gtg | gac | ttc | cgc | gag | ctg | aac | aag | cgc | acc | cag | 720 |
| Lys | Trp | Arg | Lys | Leu | Val | Asp | Phe | Arg | Glu | Leu | Asn | Lys | Arg | Thr | Gln | |
| 225 | | | | | 230 | | | | | 235 | | | | | 240 | |
| gac | ttc | tgg | gag | gtg | cag | ctg | ggc | atc | ccc | cac | ccc | gcc | ggc | ctg | aag | 768 |
| Asp | Phe | Trp | Glu | Val | Gln | Leu | Gly | Ile | Pro | His | Pro | Ala | Gly | Leu | Lys | |
| | | | | 245 | | | | | 250 | | | | | 255 | | |
| cag | aag | aag | tcc | gtg | acc | gtg | ctg | gac | gtg | ggc | gac | gcc | tac | ttc | tcc | 816 |
| Gln | Lys | Lys | Ser | Val | Thr | Val | Leu | Asp | Val | Gly | Asp | Ala | Tyr | Phe | Ser | |
| | | | 260 | | | | | 265 | | | | | 270 | | | |
| gtg | ccc | ctg | gac | aag | gac | ttc | cgc | aag | tac | acc | gcc | ttc | acc | atc | ccc | 864 |

```
                Val Pro Leu Asp Lys Asp Phe Arg Lys Tyr Thr Ala Phe Thr Ile Pro
                    275                 280                 285 tcc atc aac aac gag acc ccc ggc atc cgc tac cag tac aac gtg ctg        912
Ser Ile Asn Asn Glu Thr Pro Gly Ile Arg Tyr Gln Tyr Asn Val Leu
290                 295                 300 ccc cag ggc tgg aag ggc tcc ccc gcc atc ttc cag tgc tcc atg acc        960
Pro Gln Gly Trp Lys Gly Ser Pro Ala Ile Phe Gln Cys Ser Met Thr
305                 310                 315                 320 aag atc ctg gag ccc ttc cgc aag cag aac ccc gac atc gtg atc tac       1008
Lys Ile Leu Glu Pro Phe Arg Lys Gln Asn Pro Asp Ile Val Ile Tyr
                325                 330                 335 cag tac atg gac gac ctg tac gtg ggc tcc gac ctg gag atc ggc cag       1056
Gln Tyr Met Asp Asp Leu Tyr Val Gly Ser Asp Leu Glu Ile Gly Gln
                340                 345                 350 cac cgc acc aag atc gag gag ctg cgc cag cac ctg ctg cgc tgg ggc       1104
His Arg Thr Lys Ile Glu Glu Leu Arg Gln His Leu Leu Arg Trp Gly
                355                 360                 365 ttc acc acc ccc gac aag aag cac cag aag gag ccc ccc ttc ctg tgg       1152
Phe Thr Thr Pro Asp Lys Lys His Gln Lys Glu Pro Pro Phe Leu Trp
            370                 375                 380 atg ggc tac gag ctg cac ccc gac aag tgg acc gtg cag ccc atc gtg       1200
Met Gly Tyr Glu Leu His Pro Asp Lys Trp Thr Val Gln Pro Ile Val
385                 390                 395                 400 ctg ccc gag aag gac tcc tgg acc gtg aac gac atc cag aag ctg gtg       1248
Leu Pro Glu Lys Asp Ser Trp Thr Val Asn Asp Ile Gln Lys Leu Val
                405                 410                 415 ggc aag ctg aac tgg gcc tcc cag atc tac gcc ggc atc aaa gtc cgc       1296
Gly Lys Leu Asn Trp Ala Ser Gln Ile Tyr Ala Gly Ile Lys Val Arg
                420                 425                 430 cag ctg tgc aag ctg ctg cgc ggc acc aag gcc ctg acc gag gtg gtg       1344
Gln Leu Cys Lys Leu Leu Arg Gly Thr Lys Ala Leu Thr Glu Val Val
                435                 440                 445 ccc ctg acc gag gag gcc gag ctg gag ctg gcc gag aac cgc gag atc       1392
Pro Leu Thr Glu Glu Ala Glu Leu Glu Leu Ala Glu Asn Arg Glu Ile
450                 455                 460 ctg aag gag ccc gtg cac ggc gtg tac tac gac ccc tcc aag gac ctg       1440
Leu Lys Glu Pro Val His Gly Val Tyr Tyr Asp Pro Ser Lys Asp Leu
465                 470                 475                 480 atc gcc gag atc cag aag cag ggc cag ggc cag tgg acc tac cag atc       1488
Ile Ala Glu Ile Gln Lys Gln Gly Gln Gly Gln Trp Thr Tyr Gln Ile
                485                 490                 495 tac cag gag ccc ttc aag aac ctg aag acc ggc aaa tac gcc cgc atg       1536
Tyr Gln Glu Pro Phe Lys Asn Leu Lys Thr Gly Lys Tyr Ala Arg Met
                500                 505                 510 aag ggc gcc cac acc aac gac gtg aag cag ctg acc gag gcc gtg cag       1584
Lys Gly Ala His Thr Asn Asp Val Lys Gln Leu Thr Glu Ala Val Gln
                515                 520                 525 aag atc gcc acc gag tcc atc gtg atc tgg ggc aag act ccc aag ttc       1632
Lys Ile Ala Thr Glu Ser Ile Val Ile Trp Gly Lys Thr Pro Lys Phe
                530                 535                 540 aag ctg ccc atc cag aag gag acc tgg gag gcc tgg tgg acc gag tac       1680
Lys Leu Pro Ile Gln Lys Glu Thr Trp Glu Ala Trp Trp Thr Glu Tyr
545                 550                 555                 560 tgg cag gcc acc tgg atc ccc gag tgg gag ttc gtg aac acc ccc ccc       1728
Trp Gln Ala Thr Trp Ile Pro Glu Trp Glu Phe Val Asn Thr Pro Pro
                565                 570                 575 ctg gtg aag ctg tgg tac cag ctg gag aag gag ccc atc atc ggc gcc       1776
Leu Val Lys Leu Trp Tyr Gln Leu Glu Lys Glu Pro Ile Ile Gly Ala
                580                 585                 590
```

-continued

```
gag acc ttc tac gtg gac ggc gcc gcc aac cgc gag acc aag ctg ggc    1824
Glu Thr Phe Tyr Val Asp Gly Ala Ala Asn Arg Glu Thr Lys Leu Gly
        595                 600                 605 aag gcc ggc tac gtg acc gac cgc ggc cgc cag aag gtg gtg ccc ctg    1872
Lys Ala Gly Tyr Val Thr Asp Arg Gly Arg Gln Lys Val Val Pro Leu
610                 615                 620 acc gac acc acc aac cag aag acc gag ctg cag gcc atc cac ctg gcc    1920
Thr Asp Thr Thr Asn Gln Lys Thr Glu Leu Gln Ala Ile His Leu Ala
625                 630                 635                 640 ctg caa gac tcc ggc ctg gag gtg aac atc gtg acc gac tcc cag tat    1968
Leu Gln Asp Ser Gly Leu Glu Val Asn Ile Val Thr Asp Ser Gln Tyr
                645                 650                 655 gca ttg ggc atc atc cag gcc cag ccc gac aag tcc gag tcc gag ctg    2016
Ala Leu Gly Ile Ile Gln Ala Gln Pro Asp Lys Ser Glu Ser Glu Leu
            660                 665                 670 gtg tcc cag atc atc gag cag ctg atc aag aag gag aag gtg tac ctg    2064
Val Ser Gln Ile Ile Glu Gln Leu Ile Lys Lys Glu Lys Val Tyr Leu
        675                 680                 685 gcc tgg gtg ccc gcc cac aag ggc atc ggc ggc aac gag cag gtg gac    2112
Ala Trp Val Pro Ala His Lys Gly Ile Gly Gly Asn Glu Gln Val Asp
690                 695                 700 aag ctg gtg tcc gcc ggc atc cgc aag gtg ctg ttc ctg gac ggc atc    2160
Lys Leu Val Ser Ala Gly Ile Arg Lys Val Leu Phe Leu Asp Gly Ile
705                 710                 715                 720 gac aag gcc cag gag gag cac gag aag tac cac tcc aac tgg cgc gcc    2208
Asp Lys Ala Gln Glu Glu His Glu Lys Tyr His Ser Asn Trp Arg Ala
                725                 730                 735 atg gcc tcc gac ttc aac ctg ccc ccc gtg gtg gcc aag gag atc gtg    2256
Met Ala Ser Asp Phe Asn Leu Pro Pro Val Val Ala Lys Glu Ile Val
            740                 745                 750 gcc tcc tgc gac aag tgc cag ctg aag ggc gag gcc atg cac ggc cag    2304
Ala Ser Cys Asp Lys Cys Gln Leu Lys Gly Glu Ala Met His Gly Gln
        755                 760                 765 gtg gac tgc tcc ccc ggc atc tgg cag ctg gac tgc acc cac ctg gag    2352
Val Asp Cys Ser Pro Gly Ile Trp Gln Leu Asp Cys Thr His Leu Glu
770                 775                 780 ggc aag gtg atc ctg gtg gcc gtg cac gtg gcc tcc ggc tac atc gag    2400
Gly Lys Val Ile Leu Val Ala Val His Val Ala Ser Gly Tyr Ile Glu
785                 790                 795                 800 gcc gag gtg atc ccc gcc gag acc ggc cag gag acc gcc tac ttc ctg    2448
Ala Glu Val Ile Pro Ala Glu Thr Gly Gln Glu Thr Ala Tyr Phe Leu
                805                 810                 815 ctg aag ctg gcc ggc cgc tgg ccc gtg aag acc gtg cac acc gac aac    2496
Leu Lys Leu Ala Gly Arg Trp Pro Val Lys Thr Val His Thr Asp Asn
            820                 825                 830 ggc tcc aac ttc acc tcc acc acc gtg aag gcc gcc tgc tgg tgg gcc    2544
Gly Ser Asn Phe Thr Ser Thr Thr Val Lys Ala Ala Cys Trp Trp Ala
        835                 840                 845 ggc atc aag cag gag ttc ggc atc ccc tac aac ccc cag tcc cag ggc    2592
Gly Ile Lys Gln Glu Phe Gly Ile Pro Tyr Asn Pro Gln Ser Gln Gly
850                 855                 860 gtg atc gag tcc atg aac aag gag ctg aag aag atc atc ggc caa gtc    2640
Val Ile Glu Ser Met Asn Lys Glu Leu Lys Lys Ile Ile Gly Gln Val
865                 870                 875                 880 cgc gac cag gcc gag cac ctg aag acc gcc gtg cag atg gcc gtg ttc    2688
Arg Asp Gln Ala Glu His Leu Lys Thr Ala Val Gln Met Ala Val Phe
                885                 890                 895 atc cac aac ttc aag cgc aag ggc ggc atc ggc ggc tac tcc gcc ggc    2736
Ile His Asn Phe Lys Arg Lys Gly Gly Ile Gly Gly Tyr Ser Ala Gly
            900                 905                 910
```

```
gag cgc atc gtg gac atc atc gcc acc gac atc cag acc aag gag ctg    2784
Glu Arg Ile Val Asp Ile Ile Ala Thr Asp Ile Gln Thr Lys Glu Leu
        915                 920                 925 cag aag cag atc acc aag atc cag aac ttc cgc gtg tac tac cgc gac    2832
Gln Lys Gln Ile Thr Lys Ile Gln Asn Phe Arg Val Tyr Tyr Arg Asp
    930                 935                 940 tcc cgc gac ccc gtg tgg aag ggc ccc gcc aag ctg ctg tgg aag ggc    2880
Ser Arg Asp Pro Val Trp Lys Gly Pro Ala Lys Leu Leu Trp Lys Gly
945                 950                 955                 960 gag ggc gcc gtg gtg atc cag gac aac tcc gac atc aag gtg gtg ccc    2928
Glu Gly Ala Val Val Ile Gln Asp Asn Ser Asp Ile Lys Val Val Pro
                965                 970                 975 cgc cgc aag gcc aag atc atc cgc gac tac ggc aag cag atg gcc ggc    2976
Arg Arg Lys Ala Lys Ile Ile Arg Asp Tyr Gly Lys Gln Met Ala Gly
            980                 985                 990 gac gac tgc gtg gcc tcc cgc cag gac gag gac taa                    3012
Asp Asp Cys Val Ala Ser Arg Gln Asp Glu Asp
                995                 1000

<210> SEQ ID NO 11
<211> LENGTH: 1003
<212> TYPE: PRT
<213> ORGANISM: Artificial Sequence
<220> FEATURE:
<223> OTHER INFORMATION: Codon optimized form of HIV pol coding region

<400> SEQUENCE: 11

Phe Phe Arg Glu Asp Leu Ala Phe Pro Gln Gly Lys Ala Arg Glu Phe
1               5                   10                  15

Ser Ser Glu Gln Thr Arg Ala Asn Ser Pro Thr Arg Arg Glu Leu Gln
            20                  25                  30

Val Trp Gly Arg Asp Asn Asn Ser Leu Ser Glu Ala Gly Ala Asp Arg
        35                  40                  45

Gln Gly Thr Val Ser Phe Ser Phe Pro Gln Ile Thr Leu Trp Gln Arg
    50                  55                  60

Pro Leu Val Thr Ile Lys Ile Gly Gly Gln Leu Lys Glu Ala Leu Leu
65                  70                  75                  80

Asp Thr Gly Ala Asp Asp Thr Val Leu Glu Glu Met Asn Leu Pro Gly
                85                  90                  95

Arg Trp Lys Pro Lys Met Ile Gly Gly Ile Gly Gly Phe Ile Lys Val
            100                 105                 110

Arg Gln Tyr Asp Gln Ile Leu Ile Glu Ile Cys Gly His Lys Ala Ile
        115                 120                 125

Gly Thr Val Leu Val Gly Pro Thr Pro Val Asn Ile Ile Gly Arg Asn
    130                 135                 140

Leu Leu Thr Gln Ile Gly Cys Thr Leu Asn Phe Pro Ile Ser Pro Ile
145                 150                 155                 160

Glu Thr Val Pro Val Lys Leu Lys Pro Gly Met Asp Gly Pro Lys Val
                165                 170                 175

Lys Gln Trp Pro Leu Thr Glu Glu Lys Ile Lys Ala Leu Val Glu Ile
            180                 185                 190

Cys Thr Glu Met Glu Lys Glu Gly Lys Ile Ser Lys Ile Gly Pro Glu
        195                 200                 205

Asn Pro Tyr Asn Thr Pro Val Phe Ala Ile Lys Lys Lys Asp Ser Thr
    210                 215                 220

Lys Trp Arg Lys Leu Val Asp Phe Arg Glu Leu Asn Lys Arg Thr Gln
225                 230                 235                 240
```

```
Asp Phe Trp Glu Val Gln Leu Gly Ile Pro His Pro Ala Gly Leu Lys
            245                 250                 255

Gln Lys Lys Ser Val Thr Val Leu Asp Val Gly Asp Ala Tyr Phe Ser
            260                 265                 270

Val Pro Leu Asp Lys Asp Phe Arg Lys Tyr Thr Ala Phe Thr Ile Pro
            275                 280                 285

Ser Ile Asn Asn Glu Thr Pro Gly Ile Arg Tyr Gln Tyr Asn Val Leu
            290                 295                 300

Pro Gln Gly Trp Lys Gly Ser Pro Ala Ile Phe Gln Cys Ser Met Thr
305                 310                 315                 320

Lys Ile Leu Glu Pro Phe Arg Lys Gln Asn Pro Asp Ile Val Ile Tyr
            325                 330                 335

Gln Tyr Met Asp Asp Leu Tyr Val Gly Ser Asp Leu Glu Ile Gly Gln
            340                 345                 350

His Arg Thr Lys Ile Glu Glu Leu Arg Gln His Leu Leu Arg Trp Gly
            355                 360                 365

Phe Thr Thr Pro Asp Lys Lys His Gln Lys Glu Pro Pro Phe Leu Trp
370                 375                 380

Met Gly Tyr Glu Leu His Pro Asp Lys Trp Thr Val Gln Pro Ile Val
385                 390                 395                 400

Leu Pro Glu Lys Asp Ser Trp Thr Val Asn Asp Ile Gln Lys Leu Val
            405                 410                 415

Gly Lys Leu Asn Trp Ala Ser Gln Ile Tyr Ala Gly Ile Lys Val Arg
            420                 425                 430

Gln Leu Cys Lys Leu Leu Arg Gly Thr Lys Ala Leu Thr Glu Val Val
            435                 440                 445

Pro Leu Thr Glu Glu Ala Glu Leu Glu Leu Ala Glu Asn Arg Glu Ile
            450                 455                 460

Leu Lys Glu Pro Val His Gly Val Tyr Tyr Asp Pro Ser Lys Asp Leu
465                 470                 475                 480

Ile Ala Glu Ile Gln Lys Gln Gly Gln Gly Gln Trp Thr Tyr Gln Ile
            485                 490                 495

Tyr Gln Glu Pro Phe Lys Asn Leu Lys Thr Gly Lys Tyr Ala Arg Met
            500                 505                 510

Lys Gly Ala His Thr Asn Asp Val Lys Gln Leu Thr Glu Ala Val Gln
            515                 520                 525

Lys Ile Ala Thr Glu Ser Ile Val Ile Trp Gly Lys Thr Pro Lys Phe
            530                 535                 540

Lys Leu Pro Ile Gln Lys Glu Thr Trp Glu Ala Trp Trp Thr Glu Tyr
545                 550                 555                 560

Trp Gln Ala Thr Trp Ile Pro Glu Trp Glu Phe Val Asn Thr Pro Pro
            565                 570                 575

Leu Val Lys Leu Trp Tyr Gln Leu Glu Lys Glu Pro Ile Ile Gly Ala
            580                 585                 590

Glu Thr Phe Tyr Val Asp Gly Ala Ala Asn Arg Glu Thr Lys Leu Gly
            595                 600                 605

Lys Ala Gly Tyr Val Thr Asp Arg Gly Arg Gln Lys Val Val Pro Leu
            610                 615                 620

Thr Asp Thr Thr Asn Gln Lys Thr Glu Leu Gln Ala Ile His Leu Ala
625                 630                 635                 640

Leu Gln Asp Ser Gly Leu Glu Val Asn Ile Val Thr Asp Ser Gln Tyr
            645                 650                 655
```

```
Ala Leu Gly Ile Ile Gln Ala Gln Pro Asp Lys Ser Glu Ser Glu Leu
            660                 665                 670

Val Ser Gln Ile Ile Glu Gln Leu Ile Lys Lys Glu Lys Val Tyr Leu
        675                 680                 685

Ala Trp Val Pro Ala His Lys Gly Ile Gly Gly Asn Glu Gln Val Asp
690                 695                 700

Lys Leu Val Ser Ala Gly Ile Arg Lys Val Leu Phe Leu Asp Gly Ile
705                 710                 715                 720

Asp Lys Ala Gln Glu Glu His Glu Lys Tyr His Ser Asn Trp Arg Ala
                725                 730                 735

Met Ala Ser Asp Phe Asn Leu Pro Pro Val Val Ala Lys Glu Ile Val
            740                 745                 750

Ala Ser Cys Asp Lys Cys Gln Leu Lys Gly Glu Ala Met His Gly Gln
        755                 760                 765

Val Asp Cys Ser Pro Gly Ile Trp Gln Leu Asp Cys Thr His Leu Glu
770                 775                 780

Gly Lys Val Ile Leu Val Ala Val His Val Ala Ser Gly Tyr Ile Glu
785                 790                 795                 800

Ala Glu Val Ile Pro Ala Glu Thr Gly Gln Glu Thr Ala Tyr Phe Leu
                805                 810                 815

Leu Lys Leu Ala Gly Arg Trp Pro Val Lys Thr Val His Thr Asp Asn
            820                 825                 830

Gly Ser Asn Phe Thr Ser Thr Thr Val Lys Ala Ala Cys Trp Trp Ala
        835                 840                 845

Gly Ile Lys Gln Glu Phe Gly Ile Pro Tyr Asn Pro Gln Ser Gln Gly
850                 855                 860

Val Ile Glu Ser Met Asn Lys Glu Leu Lys Lys Ile Ile Gly Gln Val
865                 870                 875                 880

Arg Asp Gln Ala Glu His Leu Lys Thr Ala Val Gln Met Ala Val Phe
                885                 890                 895

Ile His Asn Phe Lys Arg Lys Gly Gly Ile Gly Gly Tyr Ser Ala Gly
            900                 905                 910

Glu Arg Ile Val Asp Ile Ile Ala Thr Asp Ile Gln Thr Lys Glu Leu
        915                 920                 925

Gln Lys Gln Ile Thr Lys Ile Gln Asn Phe Arg Val Tyr Tyr Arg Asp
930                 935                 940

Ser Arg Asp Pro Val Trp Lys Gly Pro Ala Lys Leu Leu Trp Lys Gly
945                 950                 955                 960

Glu Gly Ala Val Val Ile Gln Asp Asn Ser Asp Ile Lys Val Val Pro
                965                 970                 975

Arg Arg Lys Ala Lys Ile Ile Arg Asp Tyr Gly Lys Gln Met Ala Gly
            980                 985                 990

Asp Asp Cys Val Ala Ser Arg Gln Asp Glu Asp
        995                 1000

<210> SEQ ID NO 12
<211> LENGTH: 8908
<212> TYPE: DNA
<213> ORGANISM: Artificial Sequence
<220> FEATURE:
<223> OTHER INFORMATION: Packaging construct pHDmHgpm2 comprising a
      codon optimized form of HIV gag pol region

<400> SEQUENCE: 12
agcttggccc attgcatacg ttgtatccat atcataatat gtacatttat attggctcat    60
```

-continued

| | |
|---|---|
| gtccaacatt accgccatgt tgacattgat tattgactag ttattaatag taatcaatta | 120 |
| cggggtcatt agttcatagc ccatatatgg agttccgcgt tacataactt acggtaaatg | 180 |
| gcccgcctgg ctgaccgccc aacgacccc gcccattgac gtcaataatg acgtatgttc | 240 |
| ccatagtaac gccaataggg actttccatt gacgtcaatg ggtggagtat ttacggtaaa | 300 |
| ctgcccactt ggcagtacat caagtgtatc atatgccaag tacgccccct attgacgtca | 360 |
| atgacggtaa atggcccgcc tggcattatg cccagtacat gaccttatgg gactttccta | 420 |
| cttggcagta catctacgta ttagtcatcg ctattaccat ggtgatgcgg ttttggcagt | 480 |
| acatcaatgg gcgtggatag cggtttgact cacggggatt tccaagtctc cacccccattg | 540 |
| acgtcaatgg gagtttgttt tggcaccaaa atcaacggga ctttccaaaa tgtcgtaaca | 600 |
| actccgcccc attgacgcaa atgggcggta ggcgtgtacg gtgggaggtc tatataagca | 660 |
| gagctcgttt agtgaaccgt cagatcgcct ggagacgcca tccacgctgt tttgacctcc | 720 |
| atagaagaca ccgggaccga tccagcctcc cctcgaagct gatcctgaga acttcagggt | 780 |
| gagtctatgg gacccttgat gttttctttc cccttctttt ctatggttaa gttcatgtca | 840 |
| taggaagggg agaagtaaca gggtacacat attgaccaaa tcagggtaat tttgcatttg | 900 |
| taatttaaa aaatgctttc ttcttttaat atactttttt gtttatctta tttctaatac | 960 |
| tttccctaat ctcttcttt cagggcaata atgatacaat gtatcatgcc tctttgcacc | 1020 |
| attctaaaga ataacagtga taatttctgg gttaaggcaa tagcaatatt tctgcatata | 1080 |
| aatatttctg catataaatt gtaactgatg taagaggttt catattgcta atagcagcta | 1140 |
| caatccagct accattctgc ttttatttta tggttgggat aaggctggat tattctgagt | 1200 |
| ccaagctagg ccctttgct aatcatgttc atacctctta tcttcctccc acagctcctg | 1260 |
| ggcaacgtgc tggtctgtgt gctggcccat cactttggca aagaattcta gactgccatg | 1320 |
| ggcgcccgcg cctccgtgct gtccggcggc gagctggaca agtgggagaa gatccgcctg | 1380 |
| cgccccggcg gcaagaagca gtacaagctg aagcacatcg tgtgggcctc ccgcgagctg | 1440 |
| gagcgcttcg ccgtgaaccc cggcctgctg gagacctccg agggctgccg ccagatcctg | 1500 |
| ggccagctgc agccctccct gcaaaccggc tccgaggagc tgcgctccct gtacaacacc | 1560 |
| atcgccgtgc tgtactgcgt gcaccagcgc atcgacgtga aggacaccaa ggaggccctg | 1620 |
| gacaagatcg aggaggagca gaacaagtcc aagaagaagg cccagcaggc cgccgccgac | 1680 |
| accggcaaca actcccaggt gtcccagaac taccccatcg tgcagaacct gcagggccag | 1740 |
| atggtgcacc aggccatctc ccccgcacc ctgaacgcct gggtgaaggt ggtggaggag | 1800 |
| aaggccttct cccccgaagt catccccatg ttctccgccc tgtccgaggg cgccaccccc | 1860 |
| caggacctga caccatgct gaacaccgtg gcggccacc aggccgccat gcagatgctg | 1920 |
| aaggagacca tcaacgagga ggccgccgag tgggaccgcc tgcaccccgt gcacgccggc | 1980 |
| cccatcgccc ccgccagat gcgcgagccc gcggctccg acatcgccgg caccacctcc | 2040 |
| accctgcaag agcagatcgg ctggatgacc acaaccccc ccatcccgt gggcgagatc | 2100 |
| tacaagcgct ggatcatcct gggcctgaac aagatcgtgc gcatgtactc ccccacctcc | 2160 |
| atcctggaca tccgccaggg ccccaaggag cccttccgcg actacgtgga ccgcttctac | 2220 |
| aagaccctgc gcgccgagca ggcctcccag gaggtaaaga actggatgac cgagaccctg | 2280 |
| ctggtgcaga acgccaaccc cgactgcaag accatcctga aggcctggg ccccggcgcc | 2340 |
| accctggagg agatgatgac cgcctgccag ggcgtgggcg gccccggcca aaggccgc | 2400 |
| gtgctggccg aggccatgtc ccaagtcacc aaccccgcca ccatcatgat ccagaagggc | 2460 |

-continued

```
aacttccgca accagcgcaa gaccgtgaag tgcttcaact gcggcaagga gggccacatc    2520
gccaagaact gccgcgcccc ccgcaagaag ggctgctgga agtgcggcaa ggagggccac    2580
cagatgaaag attgtactga gagacaggct aatttttag ggaagatctg gccttcccac     2640
aagggaaggc cagggaattt tcttcagagc agaccagagc caacagcccc accagaagag    2700
agcttcaggt ttgggaaga gacaacaact ccctctcaga gcaggagcc gatagacaag      2760 gaactgtatc ctttagcttc cctcagatca ctctttggca gcgacccctc gtcacaataa    2820
agatcggtgg ccagctgaag gaggccctgc tggacaccgg cgccgacgac accgtgctgg    2880
aggagatgaa cctgcccggc cgctggaagc ccaagatgat cggcggcatc ggcggcttca    2940
tcaaagtccg ccagtacgac cagatcctga tcgagatctg cggccacaag gccatcggca    3000
ccgtgctggt gggccccacc cccgtgaaca tcatcggccg caacctgctg acccagatcg    3060
gctgcaccct gaacttcccc atctccccca tcgagaccgt gcccgtgaag ctgaagcccg    3120
gcatggacgg ccccaaagtc aagcagtggc ccctgaccga ggagaagatc aaggccctgg    3180
tggagatctg caccgagatg gagaaggagg gcaagatctc caagatcggc ccgagaacc     3240 cctacaacac ccccgtgttc gccatcaaga agaaggactc caccaagtgg cgcaagctgg    3300
tggacttccg cgagctgaac aagcgcaccc aggacttctg ggaggtgcag ctgggcatcc    3360
cccaccccgc cggcctgaag cagaagaagt ccgtgaccgt gctggacgtg ggcgacgcct    3420
acttctccgt gcccctggac aaggacttcc gcaagtacac cgccttcacc atcccctcca    3480
tcaacaacga gaccccggc atccgctacc agtacaacgt gctgccccag ggctggaagg     3540 gctccccgc catcttccag tgctccatga ccaagatcct ggagcccttc cgcaagcaga    3600
accccgacat cgtgatctac cagtacatgg acgacctgta cgtgggctcc gacctggaga    3660
tcggccagca ccgcaccaag atcgaggagc tgcgccagca cctgctgcgc tggggcttca    3720 ccaccccga caagaagcac cagaaggagc ccccttcct gtggatgggc tacgagctgc      3780
accccgacaa gtggaccgtg cagcccatcg tgctgcccga aaggactcc tggaccgtga     3840 acgacatcca gaagctggtg ggcaagctga actgggcctc ccagatctac gccggcatca    3900
aagtccgcca gctgtgcaag ctgctgcgcg gcaccaaggc cctgaccgag gtggtgcccc    3960
tgaccgagga ggccgagctg gagctggccg agaaccgcga gatcctgaag gagcccgtgc    4020
acggcgtgta ctacgacccc tccaaggacc tgatcgccga gatccagaag cagggccagg    4080
gccagtggac ctaccagatc taccaggagc ccttcaagaa cctgaagacc ggcaaatacg    4140
cccgcatgaa gggcgcccac accaacgacg tgaagcagct gaccgaggcc gtgcagaaga    4200
tcgccaccga gtccatcgtg atctggggca agactcccaa gttcaagctg cccatccaga    4260
aggagacctg ggaggcctgg tggaccgagt actggcaggc cacctggatc cccgagtggg    4320
agttcgtgaa cacccccccc ctggtgaagc tgtggtacca gctggagaag gagcccatca    4380
tcggcgccga gaccttctac gtggacggcg ccgccaaccg cgagaccaag ctgggcaagg    4440
ccggctacgt gaccgaccgc ggcgccagaa aggtggtgcc cctgaccgac accaccaacc    4500
agaagaccga gctgcaggcc atccacctgg ccctgcaaga ctccggcctg gaggtgaaca    4560
tcgtgaccga ctcccagtat gcattgggca tcatccaggc ccagcccgac aagtccgagt    4620
ccgagctggt gtcccagatc atcgagcagc tgatcaagaa ggagaaggtg tacctggcct    4680
gggtgcccgc ccacaagggc atcggcggca acgagcaggt ggacaagctg gtgtccgccg    4740
gcatccgcaa ggtgctgttc ctggacggca tcgacaaggc ccaggaggag cacgagaagt    4800
```

```
accactccaa ctggcgcgcc atggcctccg acttcaacct gcccccgtg gtggccaagg    4860 agatcgtggc ctcctgcgac aagtgccagc tgaagggcga ggccatgcac ggccaggtgg    4920
actgctcccc cggcatctgg cagctggact gcacccacct ggagggcaag gtgatcctgg    4980
tggccgtgca cgtggcctcc ggctacatcg aggccgaggt gatccccgcc gagaccggcc    5040
aggagaccgc ctacttcctg ctgaagctgg ccggccgctg gccgtgaag accgtgcaca    5100 ccgacaacgg ctccaacttc acctccacca ccgtgaaggc cgcctgctgg tgggccggca    5160
tcaagcagga gttcggcatc ccctacaacc ccagtccca gggcgtgatc gagtccatga    5220
acaaggagct gaagaagatc atcggccaag tccgcgacca ggccgagcac ctgaagaccg    5280
ccgtgcagat ggccgtgttc atccacaact tcaagcgcaa gggcggcatc ggcggctact    5340
ccgccggcga gcgcatcgtg gacatcatcg ccaccgacat ccagaccaag gagctgcaga    5400
agcagatcac caagatccag aacttccgcg tgtactaccg cgactcccgc gaccccgtgt    5460
ggaagggccc cgccaagctg ctgtggaagg gcgagggcgc cgtggtgatc caggacaact    5520
ccgacatcaa ggtggtgccc cgccgcaagg ccaagatcat ccgcgactac ggcaagcaga    5580
tggccggcga cgactgcgtg gcctcccgcc aggacgagga ctaacacatg gaaaagatta    5640
gtaaaacacc ataggccgct ctagaggatc caagcttatc gataccgtcg acctcgaggg    5700
cccagatcta attcaccca ccagtgcagg ctgcctatca gaaagtggtg gctggtgtgg    5760
ctaatgccct ggcccacaag tatcactaag ctcgctttct tgctgtccaa tttctattaa    5820
aggttccttt gttccctaag tccaactact aaactggggg atattatgaa gggccttgag    5880
catctggatt ctgcctaata aaaacatttt atttttcattg caatgatgta tttaaattat    5940
ttctgaatat tttactaaaa agggaatgtg gaggtcagt gcatttaaaa cataaagaaa    6000
tgaagagcta gttcaaacct tgggaaaata cactatatct taaactccat gaaagaaggt    6060
gaggctgcaa acagctaatg cacattggca acagcccctg atgcctatgc cttattcatc    6120
cctcagaaaa ggattcaagt agaggcttga tttggaggtt aaagttttgc tatgctgtat    6180
tttacattac ttattgtttt agctgtcctc atgaatgtct tttcactacc catttgctta    6240
tcctgcatct ctcagccttg actccactca gttctcttgc ttagagatac cacctttccc    6300
ctgaagtgtt ccttccatgt tttacggcga gatggtttct cctcgcctgg ccactcagcc    6360
ttagttgtct ctgttgtctt atagaggtct acttgaagaa ggaaaaacag ggggcatggt    6420
ttgactgtcc tgtgagccct tcttccctgc ctccccact cacagtgacc cggaatccct    6480
cgacatggca gtctagatca ttcttgaaga cgaaagggcc tcgtgatacg cctatttta    6540 taggttaatg tcatgataat aatgttttct tagacgtcag gtggcacttt tcggggaaat    6600
gtgcgcggaa cccctatttg tttatttttc taaatacatt caaatatgta tccgctcatg    6660
agacaataac cctgataaat gcttcaataa tattgaaaaa ggaagagtat gagtattcaa    6720
catttccgtg tcgcccttat tccctttttt gcggcatttt gccttcctgt ttttgctcac    6780
ccagaaacgc tggtgaaagt aaaagatgct gaagatcagt tgggtgcacg agtgggttac    6840
atcgaactgg atctcaacag cggtaagatc cttgagagtt ttcgccccga agaacgtttt    6900
ccaatgatga gcacttttaa agttctgcta tgtggcgcgg tattatcccg tattgacgcc    6960
gggcaagagc aactcggtcg ccgcatacac tattctcaga atgacttggt tgagtactca    7020
ccagtcacag aaaagcatct tacggatggc atgacagtaa gagaattatg cagtgctgcc    7080
ataaccatga gtgataacac tgcggccaac ttacttctga caacgatcgg aggaccgaag    7140
gagctaaccg ctttttttgca caacatgggg gatcatgtaa ctcgccttga tcgttgggaa    7200
```

-continued

```
ccggagctga atgaagccat accaaacgac gagcgtgaca ccacgatgcc tgtagcaatg    7260
gcaacaacgt tgcgcaaact attaactggc gaactactta ctctagcttc ccggcaacaa    7320
ttaatagact ggatggaggc ggataaagtt gcaggaccac ttctgcgctc ggcccttccg    7380
gctggctggt ttattgctga taaatctgga gccggtgagc gtgggtctcg cggtatcatt    7440
gcagcactgg ggccagatgg taagccctcc cgtatcgtag ttatctacac gacggggagt    7500
caggcaacta tggatgaacg aaatagacag atcgctgaga taggtgcctc actgattaag    7560
cattggtaac tgtcagacca gtttactca tatatacttt agattgattt aaaacttcat    7620
ttttaattta aaaggatcta ggtgaagatc ctttttgata atctcatgac caaaatccct    7680
taacgtgagt tttcgttcca ctgagcgtca gaccccgtag aaaagatcaa aggatcttct    7740
tgagatcctt ttttctgcg cgtaatctgc tgcttgcaaa caaaaaaacc accgctacca    7800
gcggtggttt gtttgccgga tcaagagcta ccaactcttt ttccgaaggt aactggcttc    7860
agcagagcgc agataccaaa tactgttctt ctagtgtagc cgtagttagg ccaccacttc    7920
aagaactctg tagcaccgcc tacatacctc gctctgctaa tcctgttacc agtggctgct    7980
gccagtggcg ataagtcgtg tcttaccggg ttggactcaa gacgatagtt accggataag    8040
gcgcagcggt cgggctgaac ggggggttcg tgcacacagc ccagcttgga gcgaacgacc    8100
tacaccgaac tgagatacct acagcgtgag ctatgagaaa gcgccacgct tcccgaaggg    8160
agaaaggcgg acaggtatcc ggtaagcggc agggtcggaa caggagagcg cacgagggag    8220
cttccagggg gaaacgcctg gtatctttat agtcctgtcg ggtttcgcca cctctgactt    8280
gagcgtcgat ttttgtgatg ctcgtcaggg gggcggagcc tatggaaaaa cgccagcaac    8340
ggatgcgccg cgtgcggctg ctggagatgg cggacgcgat ggatatgttc tgccaagggt    8400
tggtttgcgc attcacagtt ctccgcaaga attgattggc tccaattctt ggagtggtga    8460
atccgttagc gaggtgccgc cggcttccat tcaggtcgag gtggcccggc tccatgcacc    8520
gcgacgcaac gcggggaggc agacaaggta tagggcggcg cctacaatcc atgccaaccc    8580
gttccatgtg ctcgccgagg cggcataaat ccccgtgacg atcagcggtc caatgatcga    8640
agttaggctg gtaagagccg cgagcgatcc ttgaagctgt ccctgatggt cgtcatctac    8700
ctgcctggac agcatggcct gcaacgcggg catcccgatg ccgccggaag cgagaagaat    8760
cataatgggg aaggccatcc agcctcgcgt cggggagctt tttgcaaaag cctaggcctc    8820 caaaaagcc tcctcactac ttctggaata gctcagaggc cgaggcggcc tcggcctctg    8880
cataaataaa aaaattagt cagccatg                                        8908
```

What is claimed is:

1. A packaging cell line comprising:
   a) a mammalian cell;
   b) a first retroviral nucleotide sequence in the cell which comprises a codon optimized coding sequence for a HIV gagpol and lacks coding sequences for HIV accessory proteins, Rev response element and constitutive transport elements;
   c) a second retroviral nucleotide sequence in the cell which comprises the coding sequence for a heterologous envelope protein; and
   d) a third retroviral nucleotide sequence in the cell which comprises a DNA sequence of interest and HIV cis-acting sequences required for packaging, reverse transcription and integration, wherein said packaging cell line produces a HIV-derived retroviral vector particle.

2. A packaging cell line of claim 1 wherein the heterologous envelope protein is the G glycoprotein of vesicular stomatitis virus (VSV G).

3. A packaging cell line of claim 1 wherein the heterologous envelope protein is the amphotropic envelope of the Moloney leukemia virus.

4. A packaging cell line comprising:
   a) a mammalian cell;
   b) a first retroviral nucleotide sequence in the cell which comprises a codon optimized coding sequence for a HIV gagpol and lacks coding sequences for HIV accessory proteins, Rev response element and constitutive transport elements; and
   a second retroviral nucleotide sequence in the cell which comprises a DNA sequence of interest and HIV cis-acting sequences required for packaging, reverse transcription and integration.

5. A packaging cell line comprising:
a) a mammalian cell;
b) a first retroviral nucleotide sequence in the cell which comprises a codon optimized coding sequence for a HIV gagpol and lacks coding sequences for HIV accessory proteins, Rev response element and constitutive transport elements; and
c) a second retroviral nucleotide sequence in the cell which comprises the coding sequence for a heterologous envelope protein.

6. A method of producing a packaging cell line which produces a HIV-derived retroviral vector particle, comprising co-transfecting mammalian host cells with:
a) a first plasmid comprising a codon optimized DNA sequence which encodes HIV gagpol proteins and lacks DNA sequences encoding HIV accessory proteins, Rev response element and constitutive transport elements;
b) a second plasmid comprising a DNA sequence which encodes a heterologous envelope protein; and
c) a third plasmid comprising a DNA sequence of interest and HIV cis-acting sequences required for packaging, reverse transcription and integration, thereby producing a packaging cell line which produces a HIV-derived retroviral vector particle.

7. A method of claim 6 wherein the heterologous envelope protein is the G glycoprotein of vesicular stomatitis virus (VSV G).

8. A method of claim 6 wherein the heterologous envelope protein is the amphotropic envelope protien of the Moloney leukemia virus.

9. A method of producing a HIV-derived retroviral vector particle comprising the steps of:
a) co-transfecting mammalian host cells with:
i) a first plasmid comprising a codon optimized DNA sequence which encodes HIV gagpol proteins and lacks DNA sequences encoding HIV accessory proteins, Rev response element and constitutive transport elements;
ii) a second plasmid comprising a DNA sequence which encodes a heterologous envelope protein; and
iii) a third plasmid comprising a DNA sequence of interest and HIV cis-acting sequences required for packaging, reverse transcription and integration,
b) maintaining the transfected cells under conditions suitable for virus particle production; and
c) recovering virus particle produced in step b).

10. A method of claim 9 wherein the heterologous envelope protein is the G glycoprotein of vesicular stomatitis virus (VSV G).

11. A method of claim 9 wherein the heterologous envelope protein is the amphotropic envelope of the Moloney leukemia virus.

12. A packaging cell line comprising:
a) a mammalian cell;
b) a first retroviral nucleotide sequence in the cell which comprises a codon optimized coding sequence for a lentivirus gagpol and lacks coding sequences for lentivirus accessory proteins, Rev response element and constitutive transport elements;
c) a second retroviral nucleotide sequence in the cell which comprises the coding sequence for a heterologous envelope protein; and
d) a third retroviral nucleotide sequence in the cell which comprises a DNA sequence of interest and lentivirus cis-acting sequences required for packaging, reverse transcription and integration,
wherein said packaging cell line produces a lentivirus-derived retroviral vector particle.

13. A packaging cell line of claim 12 wherein the heterologous envelope protein is the G glycoprotein of vesicular stomatitis virus (VSV G).

14. A packaging cell line of claim 12 wherein the heterologous envelope protein is the amphotropic envelope of the Moloney leukemia virus.

15. A packaging cell line comprising:
a) a mammalian cell;
b) a first retroviral nucleotide sequence in the cell which comprises a codon optimized coding sequence for lentivirus gagpol and lacks coding sequences for lentivirus accessory proteins, Rev response element and constitutive transport elements; and
c) a second retroviral nucleotide sequence in the cell which comprises a DNA sequence of interest and lentivirus cis-acting sequences required for packaging, reverse transcription and integration.

16. A packaging cell line comprising:
a) a mammalian cell;
b) a first retroviral nucleotide sequence in the cell which comprises a codon optimized coding sequence for lentivirus gagpol and lacks coding sequences for lentivirus accessory proteins, Rev response element and constitutive transport elements; and
c) a second retroviral nucleotide sequence in the cell which comprises the coding sequence for a heterologous envelope protein.

17. A method of producing a packaging cell line which produces a lentivirus-derived retroviral vector particle, comprising co-transfecting mammalian host cells with:
a) a first plasmid comprising a codon optimized DNA sequence which encodes lentivirus gagpol proteins and lacks DNA sequences encoding lentivirus accessory proteins, Rev response element and constitutive transport elements;
b) a second plasmid comprising a DNA sequence which encodes a heterologous envelope protein; and
c) a third plasmid comprising a DNA sequence of interest and lentivirus cis-acting sequences required for packaging, reverse transcription and integration, thereby producing a packaging cell line which produces a lentivirus-derived retroviral vector particle.

18. A method of claim 17 wherein the heterologous envelope protein is the G glycoprotein of vesicular stomatitis virus (VSV G).

19. A method of claim 17 wherein the heterologous envelope protein is the amphotropic envelope of the Moloney leukemia virus.

20. A method of producing a lentivirus-derived retroviral vector particle comprising the steps of:
a) co-transfecting mammalian host cells with:
i) a first plasmid comprising a codon optimized DNA sequence which encodes lentivirus gagpol proteins and lacks DNA sequences encoding lentivirus accessory proteins, Rev response element and constitutive transport elements;
ii) a second plasmid comprising a DNA sequence which encodes a heterologous envelope protein; and iii) a third plasmid comprising a DNA sequence of interest and lentivirus cis-acting sequences required for packaging, reverse transcription and integration, b) maintaining the transfected cells under conditions suitable for virus particle production; and c) recovering virus particle produced in step b).

21. A method of claim 20 wherein the heterologous envelope protein is the G glycoprotein of vesicular stomatitis virus (VSV G).

22. A method of claim 20 wherein the heterologous envelope protein is the amphotropic envelope of the Moloney leukemia virus.

* * * * *

Adverse Decision in Interference

Patent No. 6,958,226, John T. Gray, Richard Milligan, and Jeng Shin Lee, PACKAGING CELLS COMPRISING CODON-OPTIMIZED GAGPOL SEQUENCES AND LACKING LENTIVIRAL ACCESSORY PROTEINS, Interference No. 105,672, final judgment adverse to the patentees rendered June 8, 2009, as to claims 1-22.

(*Official Gazette, January 12, 2010*)